(12) United States Patent
Paik et al.

(10) Patent No.: US 9,757,342 B2
(45) Date of Patent: Sep. 12, 2017

(54) METHOD FOR PREPARING PROTEIN CAGE, AND IN SITU METHOD FOR PREPARING HYDROPHOBIC ADDITIVE-SUPPORTED CORE-SHELL STRUCTURED POLYMER-PROTEIN PARTICLES

(71) Applicants: PUSAN NATIONAL UNIVERSITY INDUSTRY—UNIVERSITY COOPERATION FOUNDATION, Busan (KR); KOREA RESEARCH INSTITUTE OF CHEMICAL TECHNOLOGY, Daejeon (KR); GACHON UNIVERSITY OF INDUSTRY—ACADEMIC COOPERATION FOUNDATION, Gyeonngi-do (KR)

(72) Inventors: Hyun Jong Paik, Busan (KR); Jae Kwang Song, Daejeon (KR); Seong Soo An, Seoul (KR); Chae Yeon Lee, Chungcheongbuk-do (KR); Jong Hwa Jeong, Busan (KR); Mohammad Abdul Kadir, Busan (KR); Tae Heon Lee, Busan (KR)

(73) Assignees: Pusan National University Industry-University Cooperation Foundation, Busan (KR); Korea Research Institute of Chemical Technology, Daejeon (KR); Gachon University of Industry-Academic Cooperation Foundation, Gyeonggi-do (KR)

( * ) Notice: Subject to any disclaimer, the term of this patent is extended or adjusted under 35 U.S.C. 154(b) by 15 days.

(21) Appl. No.: 14/778,906

(22) PCT Filed: Oct. 11, 2013

(86) PCT No.: PCT/KR2013/009120
§ 371 (c)(1),
(2) Date: Jan. 13, 2016

(87) PCT Pub. No.: WO2014/148713
PCT Pub. Date: Sep. 25, 2014

(65) Prior Publication Data
US 2016/0120814 A1 May 5, 2016

(30) Foreign Application Priority Data
Mar. 22, 2013 (KR) .................. 10-2013-0031128

(51) Int. Cl.
*A61K 9/48* (2006.01)
*C08H 1/00* (2006.01)
(Continued)

(52) U.S. Cl.
CPC .......... *A61K 9/4825* (2013.01); *A61K 8/0204* (2013.01); *A61K 8/64* (2013.01); *A61K 8/66* (2013.01); *A61K 9/5138* (2013.01); *A61K 47/48238* (2013.01); *A61K 49/0056* (2013.01); *A61Q 19/00* (2013.01); *C07K 14/43504* (2013.01); *C07K 14/75* (2013.01); *C08H 1/00* (2013.01); *C08J 3/246* (2013.01); *A61K 39/00* (2013.01); *A61K 2800/10* (2013.01); *C07K 2319/21* (2013.01); *C08J 2300/10* (2013.01); *C08J 2389/00* (2013.01)

(58) Field of Classification Search
None
See application file for complete search history.

(56) References Cited

U.S. PATENT DOCUMENTS

| | | | |
|---|---|---|---|
| 2002/0115747 A1* | 8/2002 | Feldheim | B01J 13/14 523/201 |
| 2002/0187197 A1 | 12/2002 | Caruso et al. | 424/490 |

(Continued)

FOREIGN PATENT DOCUMENTS

| | | | | |
|---|---|---|---|---|
| KR | 10-2007-0099767 | | 10/2007 | |
| KR | 10-2008-0030555 | | 4/2008 | |
| WO | WO 91/12823 | * | 9/1991 | A61K 49/00 |

OTHER PUBLICATIONS

Wu el al (High resolution TEM imaging and analysis of the core-shell assembly of ferritin- poly 4-vinyl pyridine (P4VP). Microsc Microanal 15(Suppl 2), p. 96-97, (2009)).*
Lee et al (Ni/NiO Core/Shell Nanoparticles for Selective Binding and Magnetic Separation of Histidine-Tagged Proteins.J. Am. Chem. Soc., 2006, 128 (33), pp. 10658-10659).*

(Continued)

*Primary Examiner* — Jake Vu
(74) *Attorney, Agent, or Firm* — Norton Rose Fulbright US LLP

(57) ABSTRACT

The present invention relates to a method for preparing a protein cage which comprises: a $1^{st}$ step of preparing an amphiphilic polymer comprising a $1^{st}$ hydrophobic polymer and a $1^{st}$ hydrophilic functional group; a $2^{nd}$ step of preparing a hydrophilic protein comprising a $2^{nd}$ functional group binding to the $1^{st}$ functional group; a $3^{rd}$ step of forming an amphiphilic polymer-protein hybrid by the binding of the $1^{st}$ functional group and the $2^{nd}$ functional group, and forming core-shell structured particles comprising a protein shell and an amphiphilic polymer core by the self-assembly of the amphiphilic polymer in a hydrophilic solvent; and a fourth step of removing some or all of the hydrophobic polymer of the core part from the core-shell structured particles.

8 Claims, 36 Drawing Sheets

(51) Int. Cl.
*A61K 47/48* (2006.01)
*A61K 8/64* (2006.01)
*A61Q 19/00* (2006.01)
*A61K 8/02* (2006.01)
*C08J 3/24* (2006.01)
*A61K 8/66* (2006.01)
*A61K 49/00* (2006.01)
*C07K 14/435* (2006.01)
*C07K 14/75* (2006.01)
*A61K 9/51* (2006.01)
*A61K 39/00* (2006.01)

(56) References Cited

U.S. PATENT DOCUMENTS

| 2011/0020236 A1* | 1/2011 | Bohmer | A61K 9/5153 424/9.3 |
| 2012/0141591 A1 | 6/2012 | Petrenko | 424/490 |
| 2012/0219600 A1 | 8/2012 | Perumal et al. | 424/400 |

OTHER PUBLICATIONS

International Search Report and Written Opinion issued in PCT/KR2013/009120, mailed on Nov. 27, 2013.

* cited by examiner

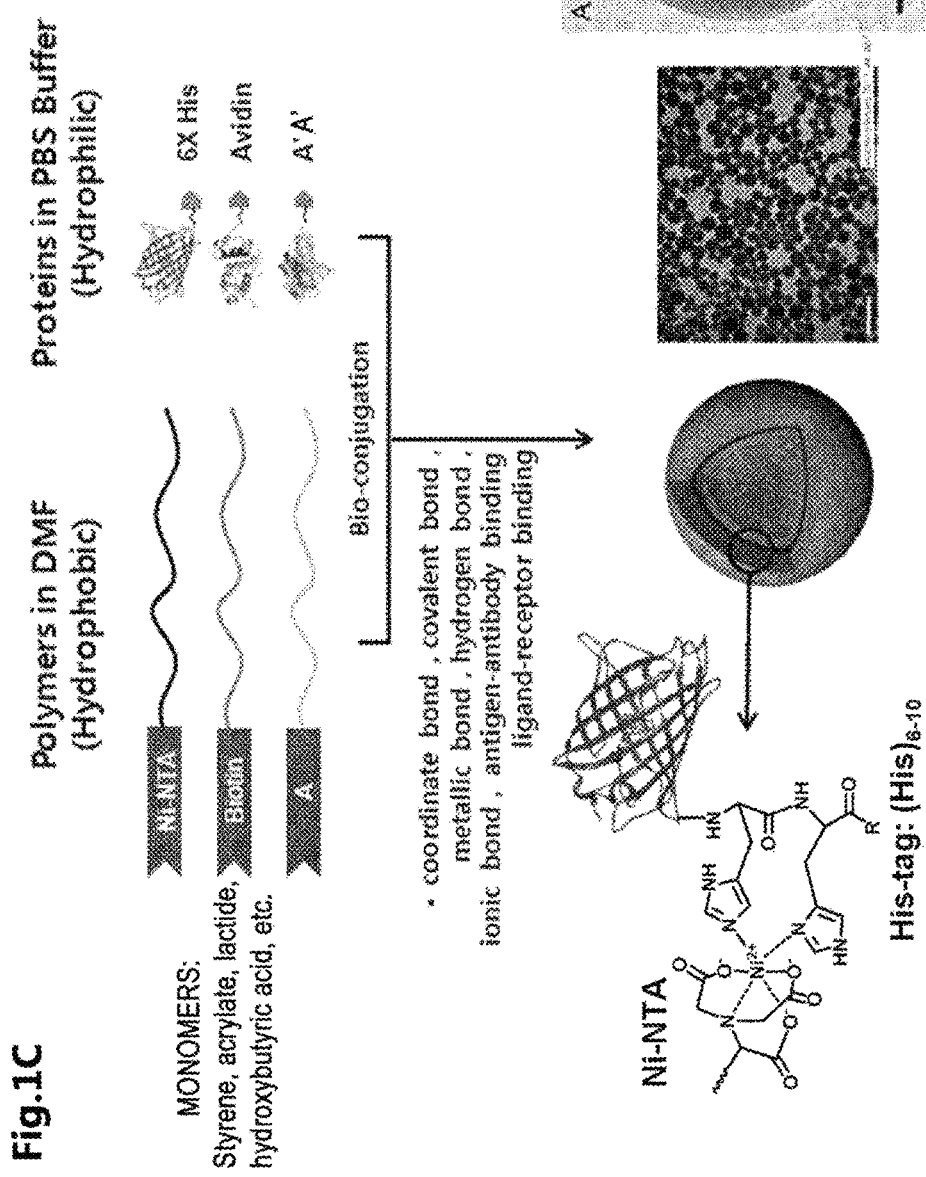

Fig.3

Self-assembled influenza nanoparticles

1. High concentration labeling of various antigens is possible
2. Size control of influenza nanoparticles is possible
3. Immune enhancer can be loaded in particles Hydrophobic & biodegradable polymer having a functional group for biological binding at one end functional group for biological binding at one end Hydrophobic & biodegradable polymer

+

H5N1 Antigen
HA
NA  Immune enhancer

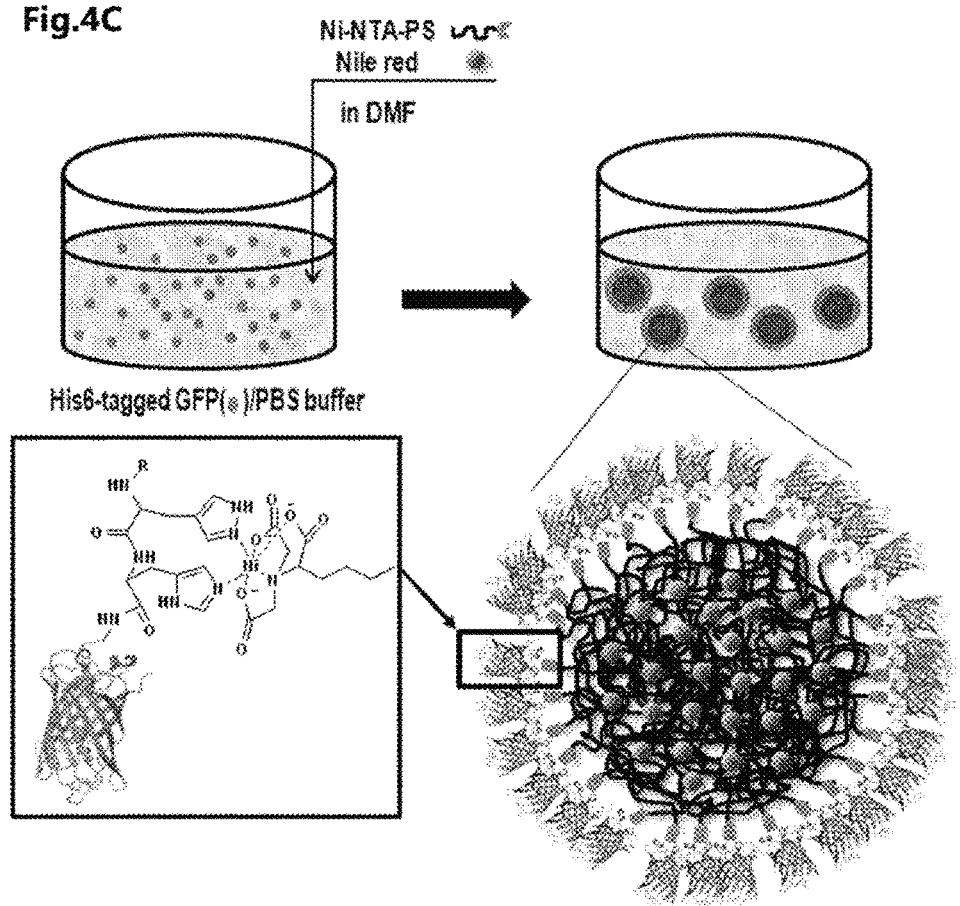

Fig.6
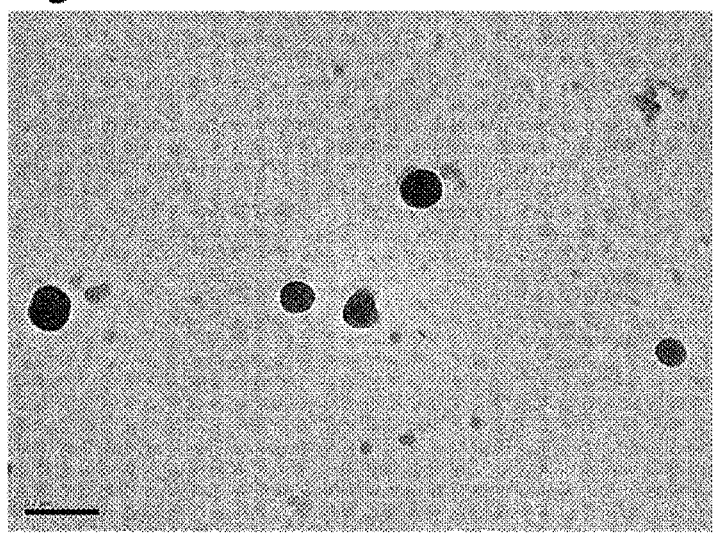
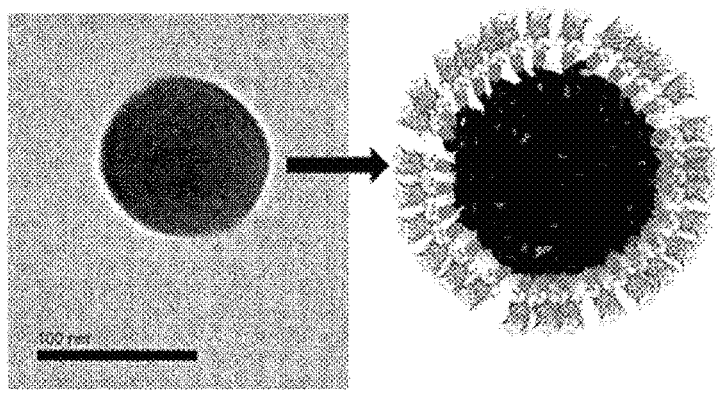
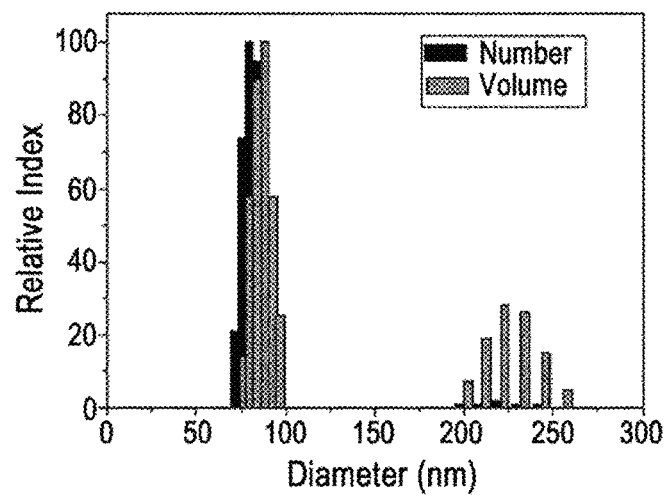

Fig. 8
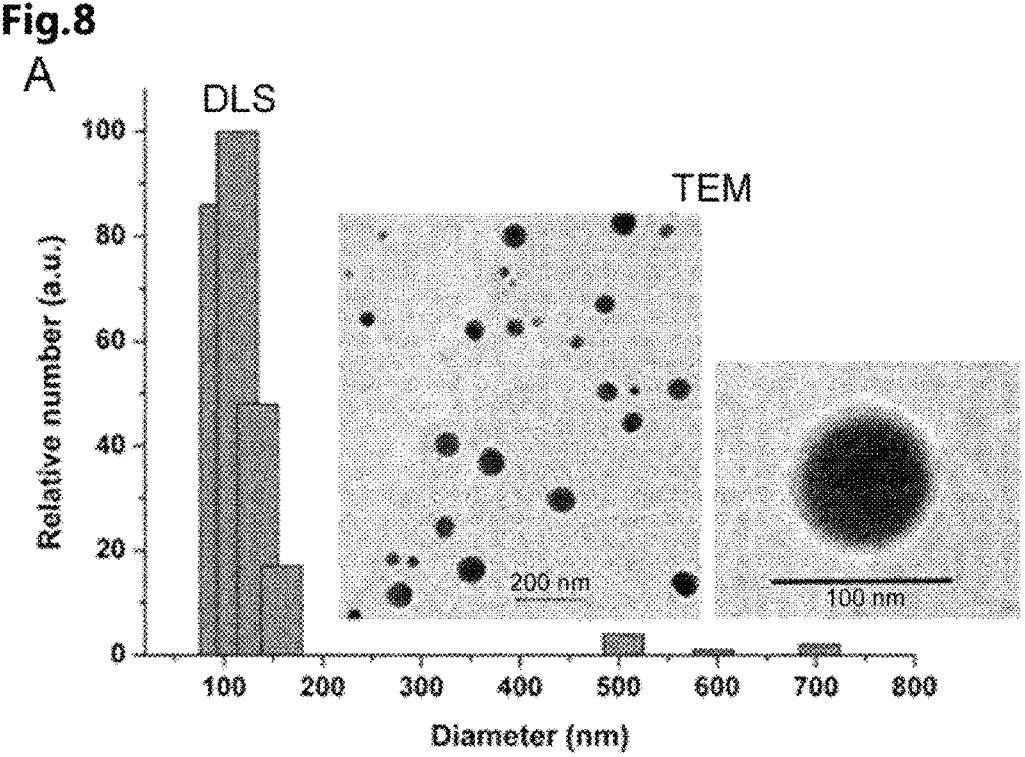
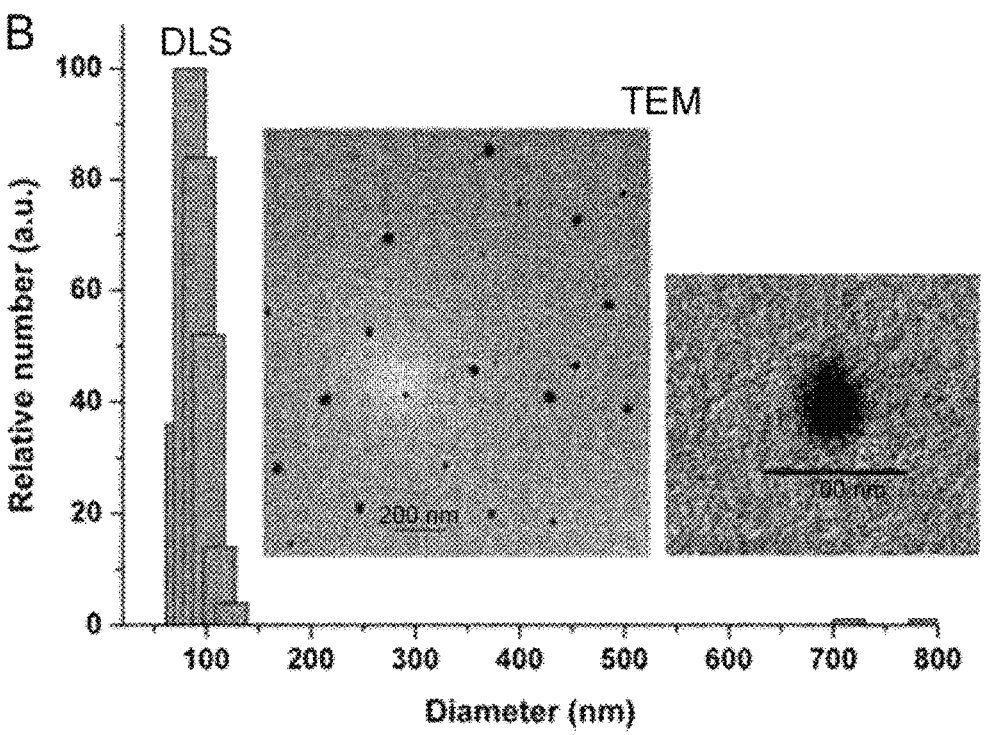

Fig.10
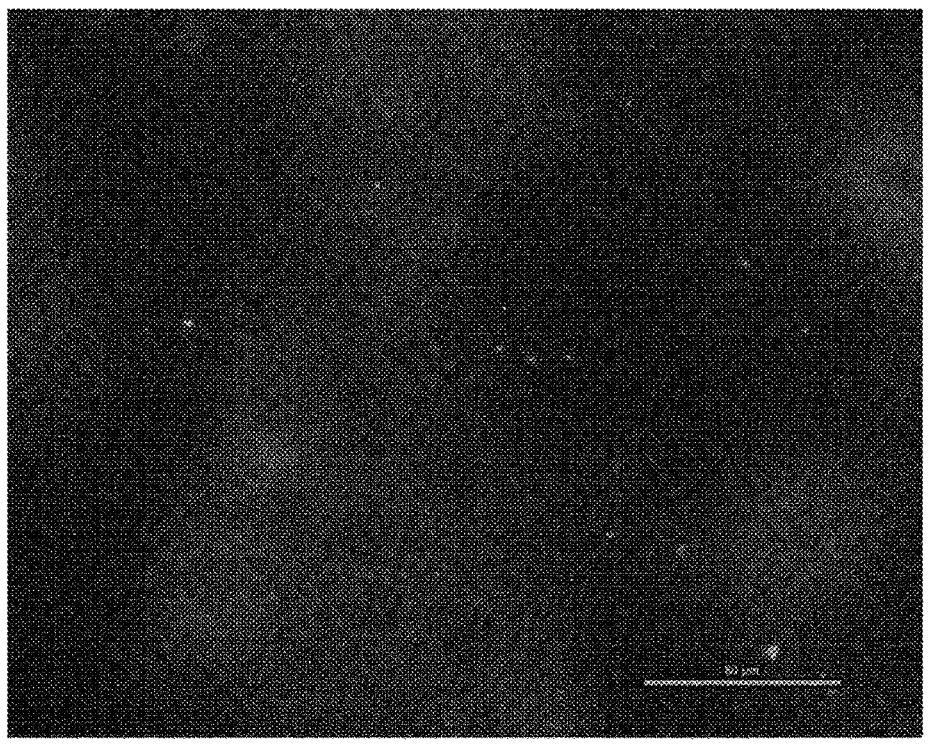
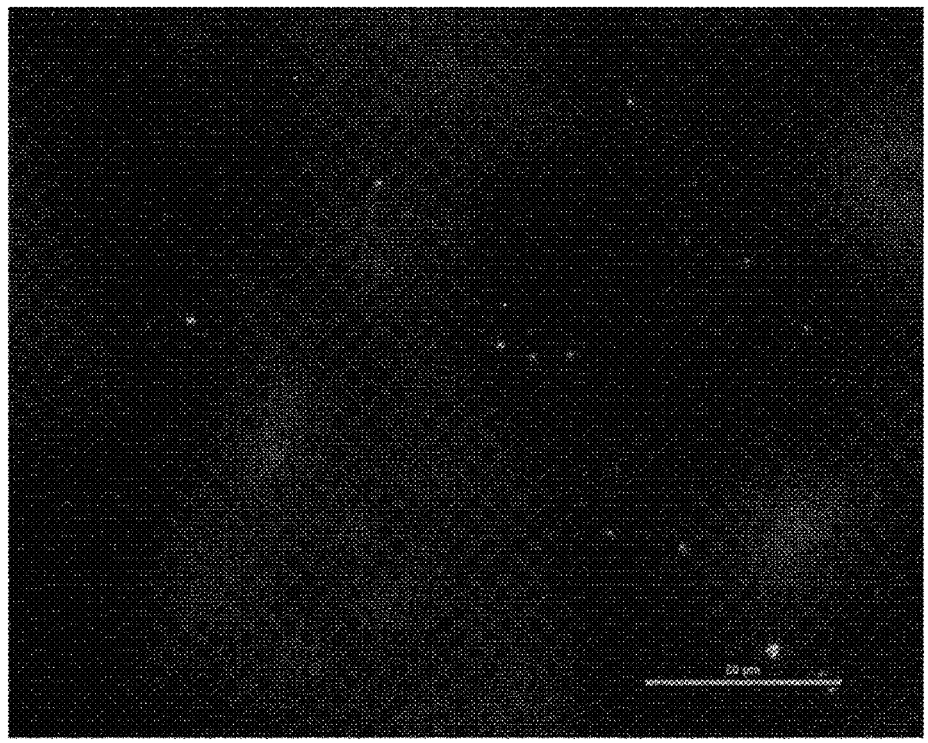

Fig.12
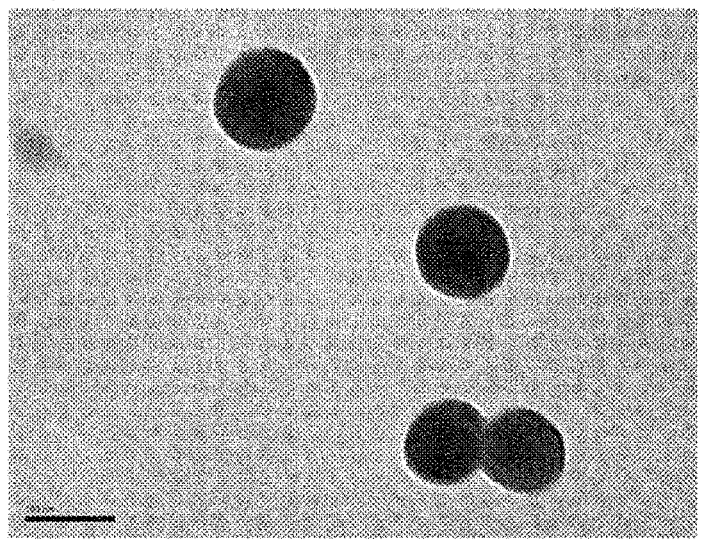
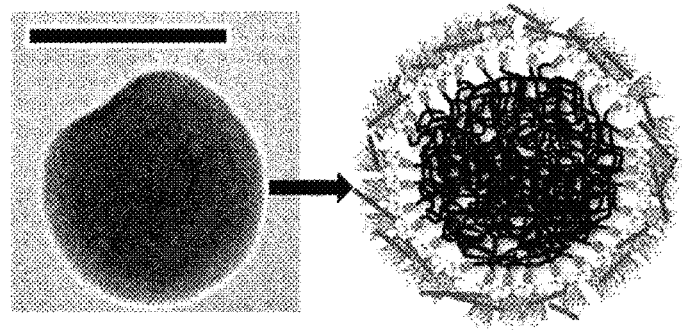
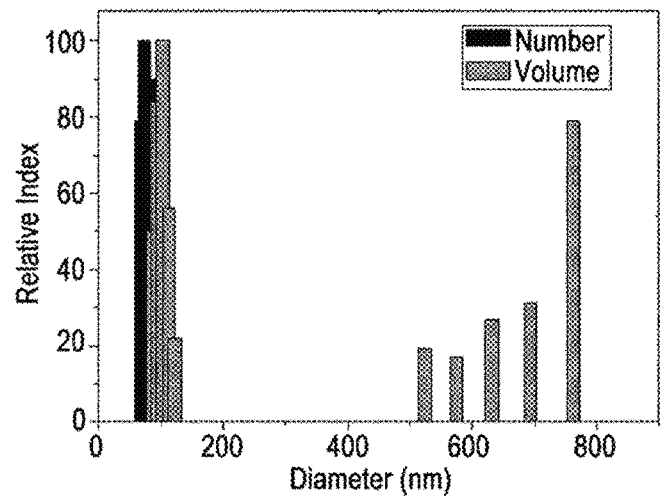

Fig.20
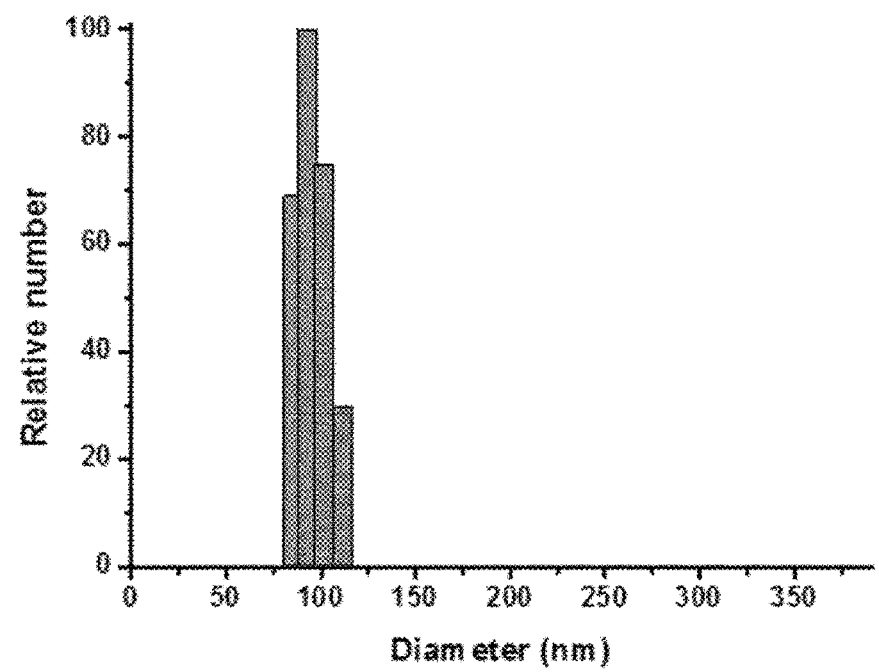
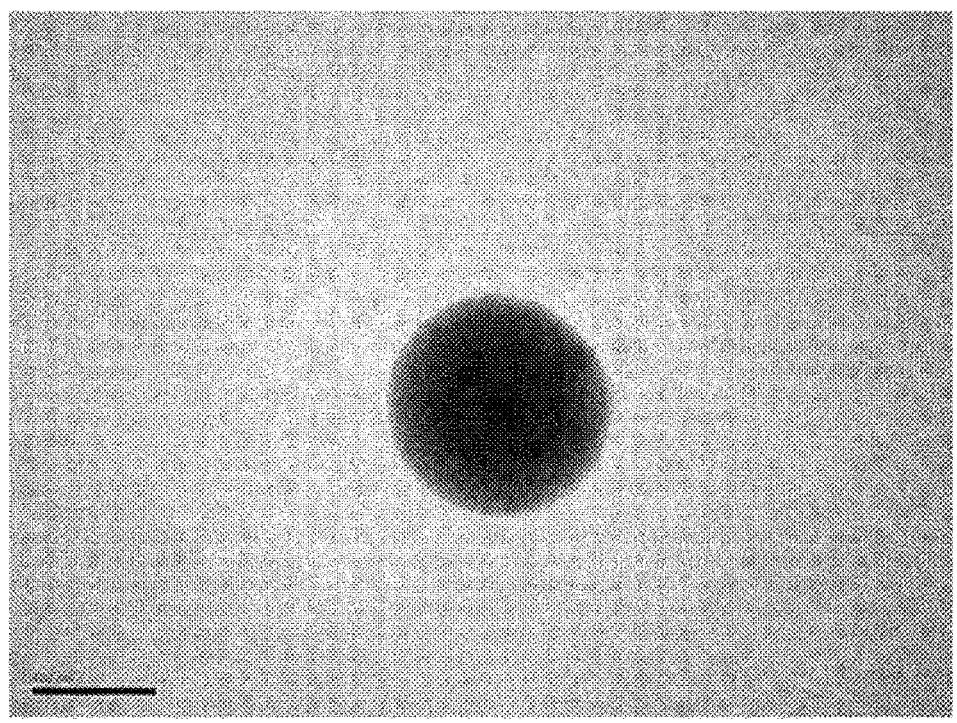

Fig.21
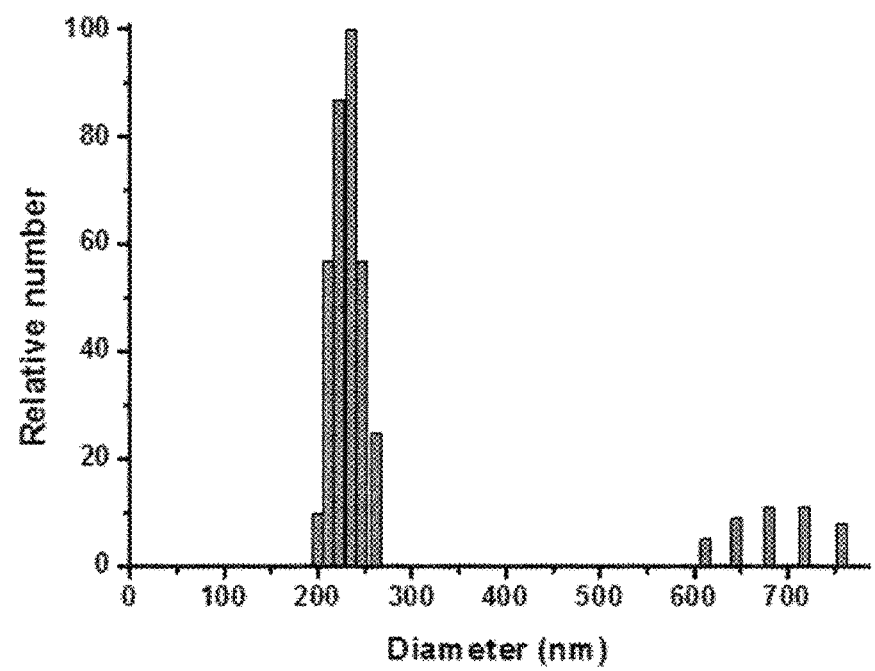
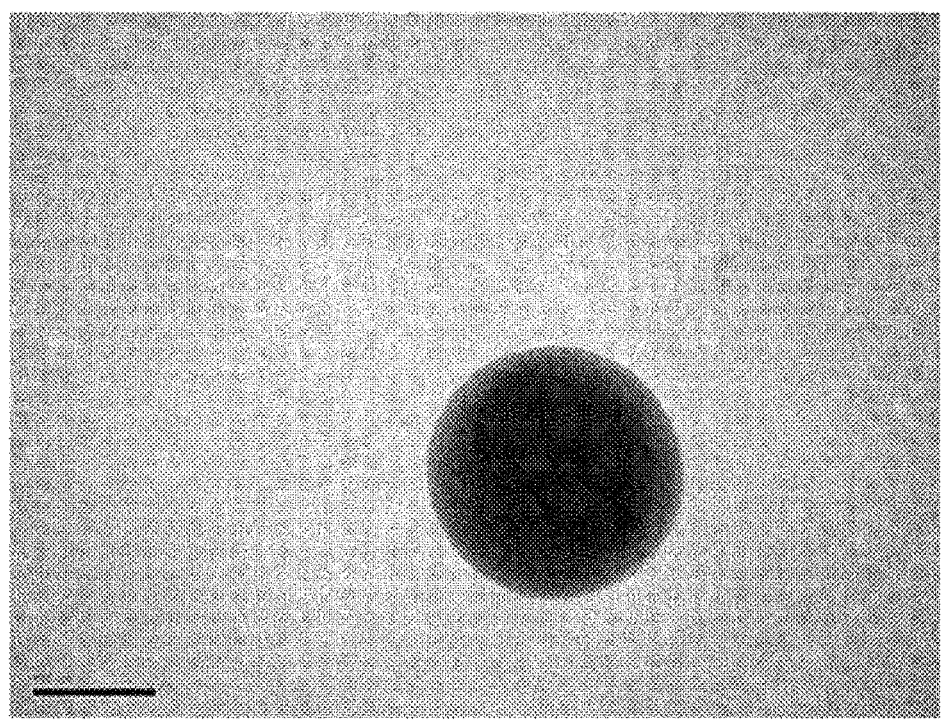

Fig.22
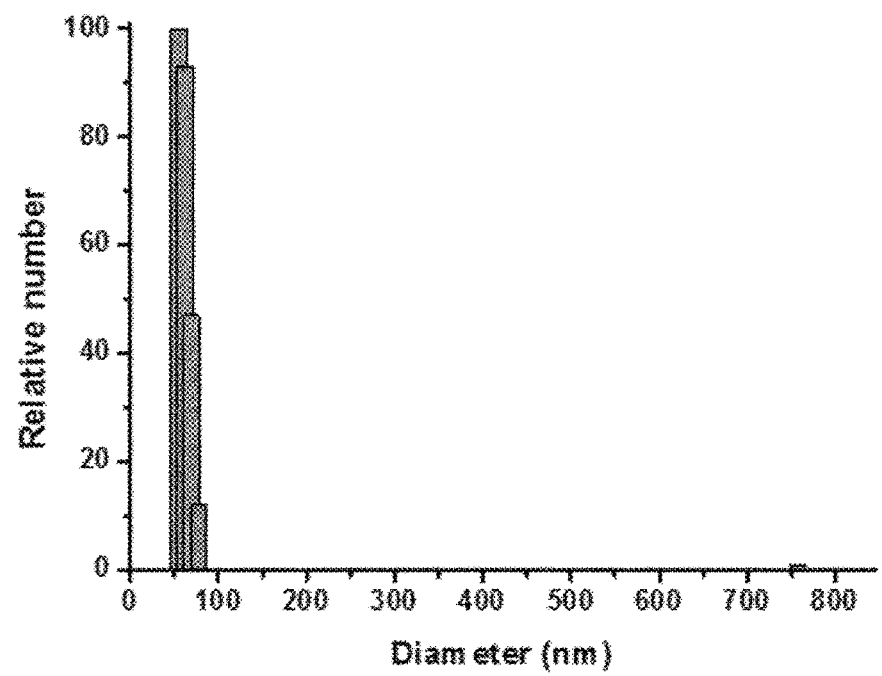
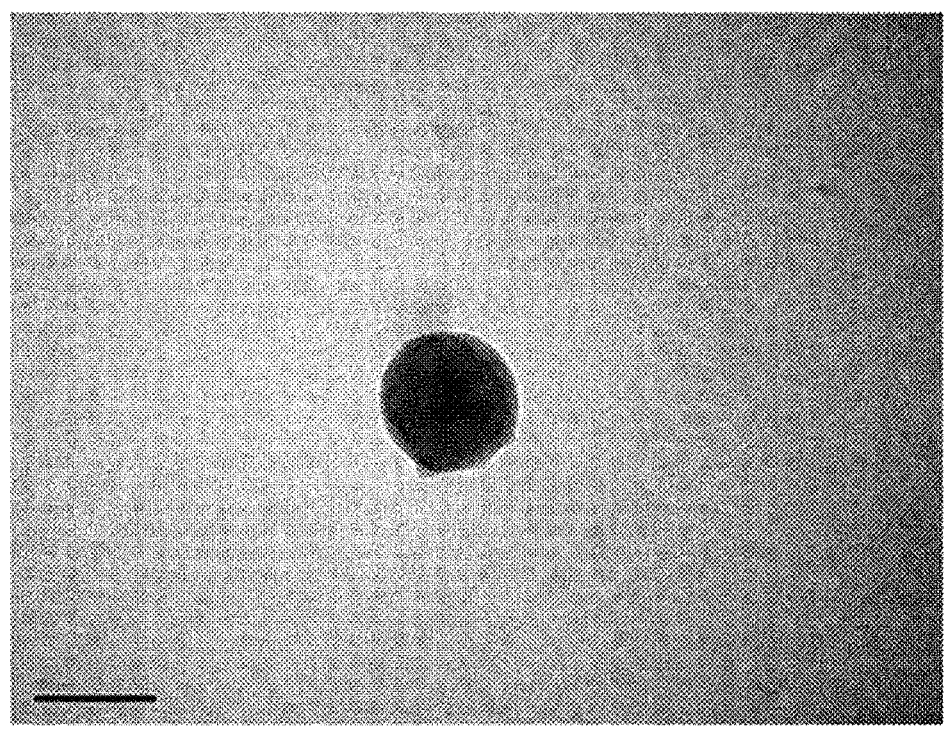

Fig.23
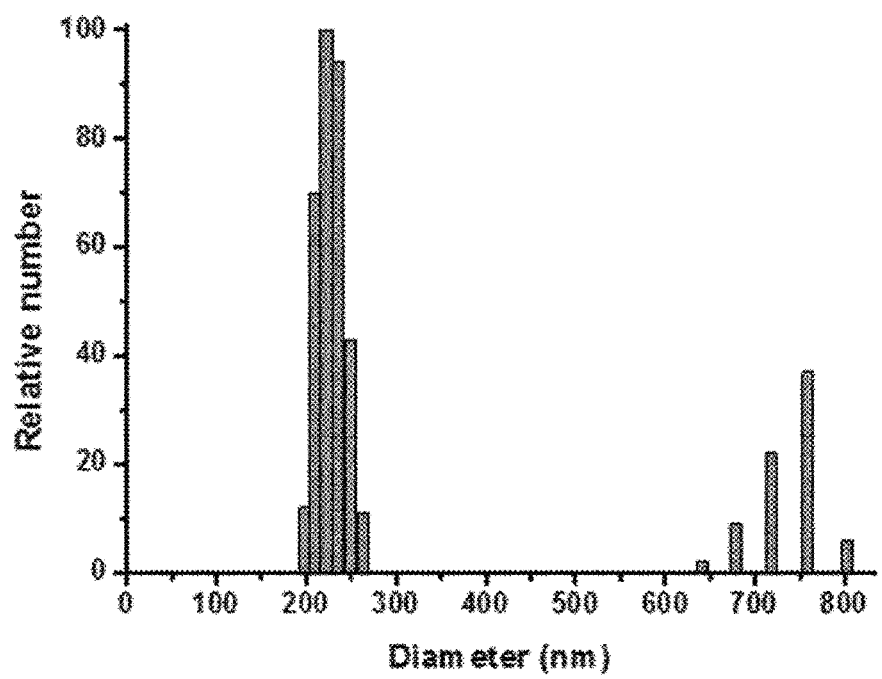
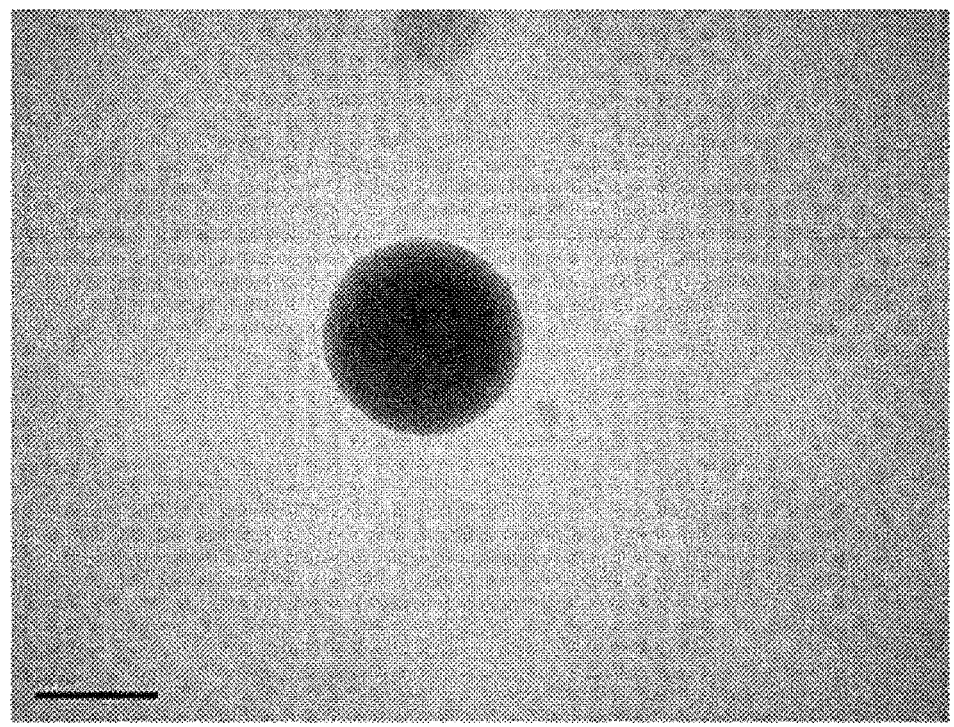

Fig.25
A
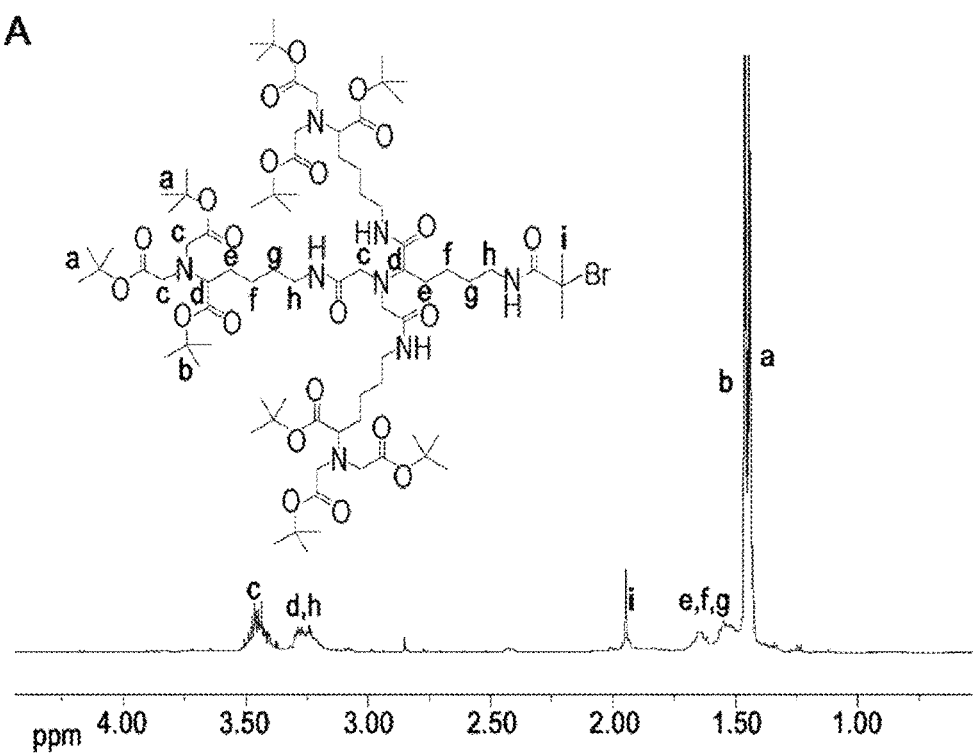
B
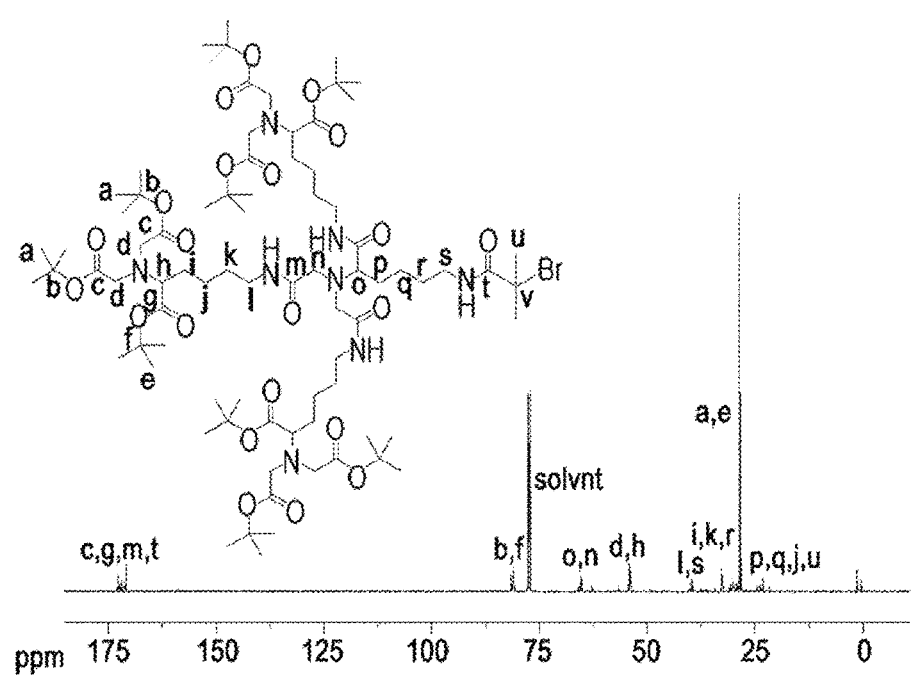

Fig. 28
A
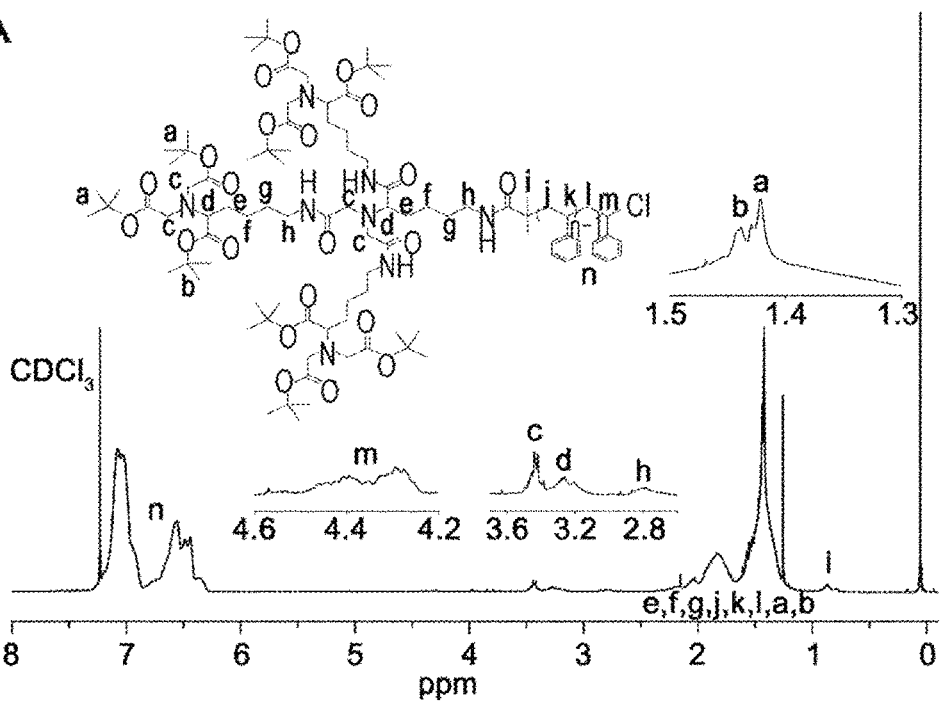
B
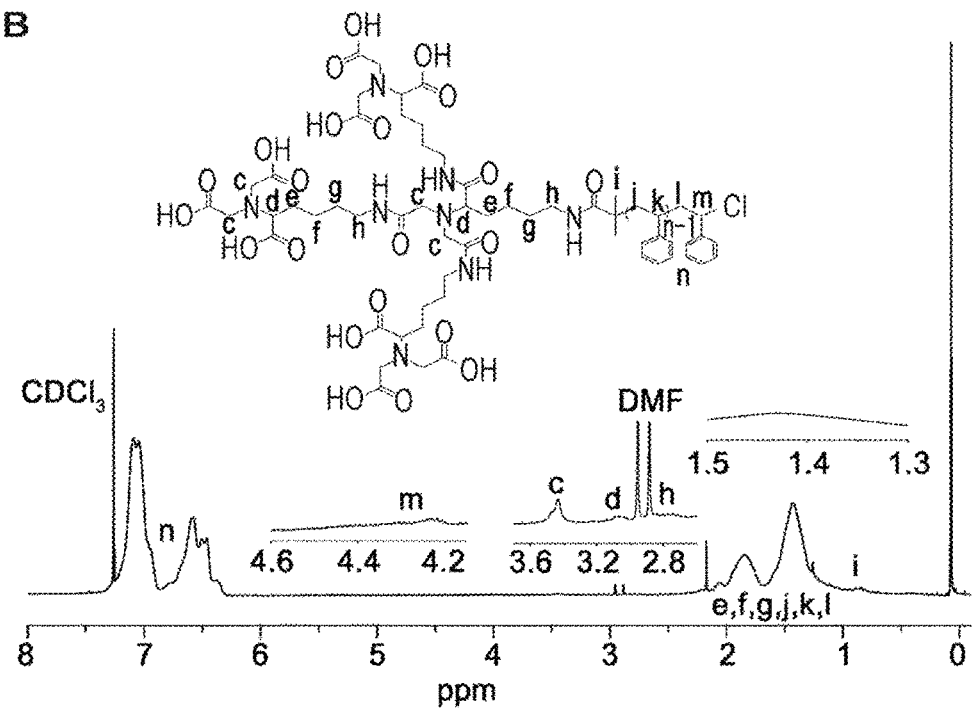

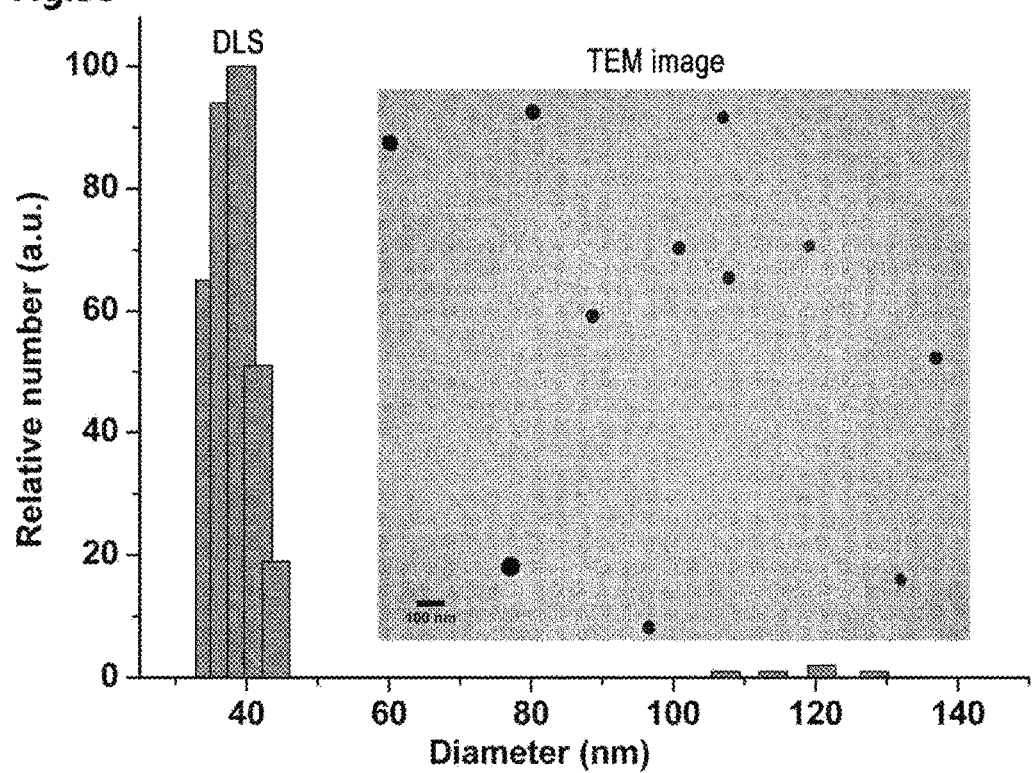

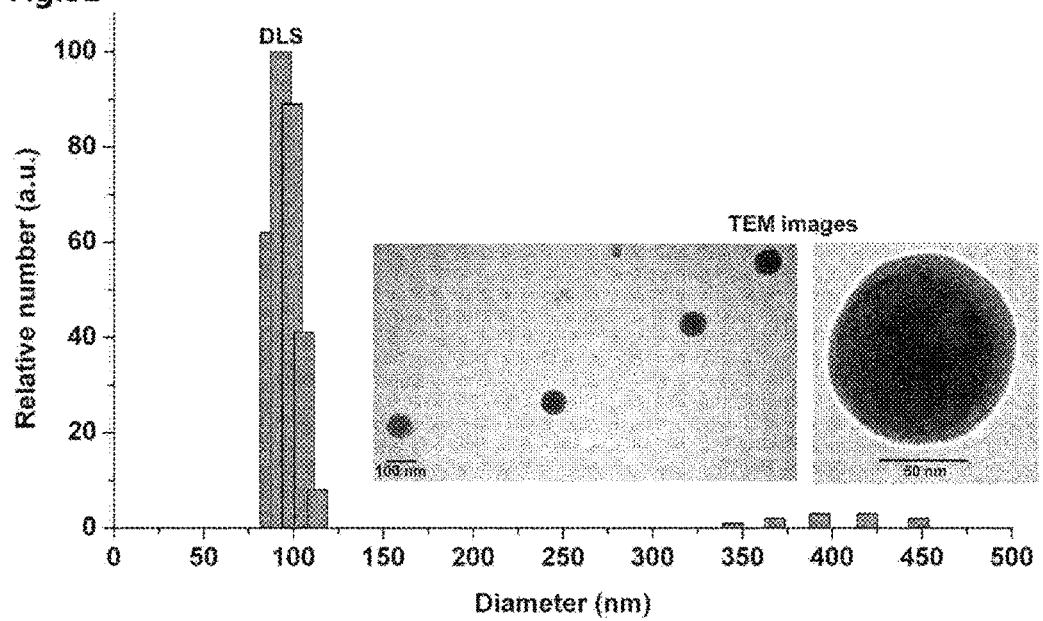

METHOD FOR PREPARING PROTEIN CAGE, AND IN SITU METHOD FOR PREPARING HYDROPHOBIC ADDITIVE-SUPPORTED CORE-SHELL STRUCTURED POLYMER-PROTEIN PARTICLES

CROSS-REFERENCE TO RELATED APPLICATIONS

This application is a national phase application under 35 U.S.C. §371 of International Application No. PCT/KR2013/009120 filed 11 Oct. 2013, which claims priority to Korean Patent Application No. 10-2013-0031128 filed 22 Mar. 2013. The entire contents of each of the above-referenced disclosures is specifically incorporated by reference herein without disclaimer.

TECHNICAL FIELD

The present invention relates to a method for preparing a protein cage, a protein cage prepared by the method, an in situ method for preparing hydrophobic additive-loaded core-shell structured polymer-protein particles, core-shell structured polymer-protein particles prepared by the method, and use thereof.

BACKGROUND ART

A drug delivery system (DDS) is a high-value key technology providing economic gains comparable to the development of new drugs and having a high potential of success, and it pursues an efficient medication, thereby improving the quality of patient treatment. The technique of solubilizing poorly soluble drugs, which belongs to a technique for promoting the absorption of a drug, one of the key techniques in the drug delivery system, is considered as the most reasonable way to reduce the development costs of new drug substances and at the same time increase the value of medicines currently on the market.

Meanwhile, nanocapsule technology can load the component of interest into a nano-sized capsule and then release it at a desired rate in a desired place. Capsule technology has been studied for a long time. Due to the limits in capsule size and material, technology development thereof has progressed slowly, but has recently been newly spotlighted through the development of nanocapsules integrated with nanotechnology. Such nanocapsule technology is applicable to a variety of fields including fine chemicals, medicaments, cosmetics, electronics, etc. depending on the development process of the capsule material and the type of substance to be loaded inside the capsule. In particular, in the fields of medicaments, cosmetics, etc., the nanocapsule has the potential to be variously utilized in targeted cancer therapy, drug delivery, transdermal absorption of cosmetics, imaging, etc. However, there are disadvantages in that the process of making a nanocapsule is complicated and a separate mold for forming the capsule is needed.

Affinity chromatography is a protein separation method using the affinity between a protein and a ligand (chemicals, amines, amino acids, peptides, proteins) by immobilizing the ligand having a specific interaction with the protein to be separated on a carrier. It is a selective separation method utilizing the specificity of the target protein among a variety of proteins in biological systems and has been widely used for separation and purification of fusion proteins and antibodies. In particular, IMAC (immobilized-metal affinity chromatography) is a method for purifying a protein having an affinity for a transition metal such as $Ni^{2+}$, $Co^{2+}$, $Zn^{2+}$, etc., using a resin as a carrier, in which a ligand is coordinated to the transition metal. The metal ions such as $Ni^{2+}$, $Co^{2+}$, etc. have been reported to have a uniquely high affinity for the histidine tag, and a typical example of such a resin includes Ni-NTA. Nitrilotriacetic acid (NTA) is a metal chelator that forms a complex with a metal ion, and Ni-NTA forms a coordinate bond with the imidazole ring of histidine.

DISCLOSURE OF THE INVENTION

Technical Problem

While researching a nanoencapsulation method, the present inventors have prepared polymer nanoparticles directly coated with a protein without a separate template, in view of the affinity chromatography used for protein purification. The inventors have also confirmed that it is possible to prepare a protein cage by removing some or all of the polymer from the protein-coated polymer nanoparticle. Furthermore, the inventors have confirmed that a hydrophobic additive can be loaded inside the protein-coated polymer nanoparticles simultaneously with the formation of the nanoparticles by a one-pot encapsulation method, and thus completed the present invention.

Technical Solution

An object of the present invention is to provide a new protein cage; a method of preparing the same; an in situ method for preparing hydrophobic additive-loaded core-shell structured polymer-protein particles; hydrophobic additive-loaded core-shell structured polymer-protein particles prepared by the method; and drug delivery systems, cosmetic compositions, compositions for imaging, artificial vaccines, and biosensors using the same.

Advantageous Effects

In the protein cage according to the present invention, the hydrophobic polymer used for forming a core is not particularly limited, and it is possible to introduce a variety of coating proteins since the protein coating shell can be formed through a binding between the $1^{st}$ and the $2^{nd}$ functional groups.

Also, using a one-pot reaction without a separate mold, an amphiphilic polymer-protein hybrid is formed through the binding between the $1^{st}$ and the $2^{nd}$ functional groups, and the hybrid can be self-assembled in a hydrophilic solvent to form the core-shell structured particles. And then, some or all of the hydrophobic polymer in the core part can be removed from the core-shell structured particle to form the protein cage, and this protein cage may be utilized as a protein device in a wide variety of fields including cosmetics, medicines, food, healthcare, etc. since various additives such as pharmacologically active substances, cosmetic materials, contrast agents, etc. can be loaded inside the protein cage thus formed.

In addition, the manufacturing process is very simple, and it is easy to control the size of core-shell particles, and thus the process can be effectively utilized in a variety of applications.

Furthermore, the protein cage according to the present invention may be synthesized in a well-defined structure by a simple process, and the existence of few constraints on the selection and introduction of proteins makes the cage available in various ways.

BRIEF DESCRIPTION OF THE DRAWINGS

FIG. 3 is a diagram illustrating an artificial vaccine which can be prepared according to one embodiment of the present invention.

FIG. 4C is a schematic diagram illustrating the formation of Nile red-loaded protein-coated polymer nanoparticles according to one embodiment of the present invention.

FIG. 6 shows TEM analysis results (A, B) and DLS data (C) of the protein-coated polymer nanoparticles prepared in Example 1.

FIG. 8 is DLS data and TEM images showing the size and shape of the polymer-protein (enzyme) particles prepared in Example 4.

FIG. 10 shows the fluorescence microscope observation results according to the cell test of the protein-coated polymer nanoparticles prepared in Example 5.

FIG. 12 shows TEM analysis results (top) and DLS data (bottom right) after a cross-linking agent (glutaraldehyde) is added to a solution comprising the polymer particles formed in Example 6.

FIG. 20 shows the size and shape of the core-shell polystyrene-GFP particles formed by the covalent bond between the NHS functional group and the histidine tag as prepared in Example 10. The left side shows the size distribution of particles measured by dynamic light scattering (DLS), and the right side shows the shape of particles observed by TEM.

FIG. 21 shows the size and shape of the core-shell polystyrene-RFP particles formed by the covalent bond between the NHS functional group and the histidine tag as prepared in Example 10. The left side shows the size distribution of particles measured by dynamic light scattering (DLS), and the right side shows the shape of particles observed by TEM.

FIG. 22 shows the size and shape of the core-shell polystyrene-YFP particles formed by the covalent bond between the NHS functional group and the histidine tag as prepared in Example 10. The left side shows the size distribution of the particles measured by dynamic light scattering (DLS), and the right side shows the shape of the particles observed by TEM.

FIG. 23 shows the size and shape of the core-shell polystyrene-fibrinogen particles formed by the covalent bond between the NHS functional group and the histidine tag as prepared in Example 10. The left side shows the size distribution of the particles measured by dynamic light scattering (DLS), and the right side shows the shape of the particles observed by TEM.

FIG. 25 shows $^1$H NMR (A) and $^{13}$C NMR (B) spectra of a p-tri-NTA initiator (6').

FIG. 28 shows $^1$H NMR (300 MHz) spectra of (A) p-tri-NTA-PS (Mn, GPC=6,400 g/mol, Đ=1.15; 7') and (B) tri-NTA-PS (Mn, GPC=5,400 g/mol, Đ=1.17; 8').

FIG. 30 shows the DLS data and TEM image of the spherical particles which are self-assembled from tri-NTA-PS in water/THF.

FIG. 31 shows the DLS data and TEM image of the polymer-protein core-shell hybrid particles self-assembled from nickel-complexed tri-NTA-PS (Ni-tri-NTA-PS) and His6-GFP through the NTA-Ni/His interaction in water/DMF (DMF 4 vol. %) according to Example 13.

BEST MODE FOR CARRYING OUT THE INVENTION

Figure 1A:
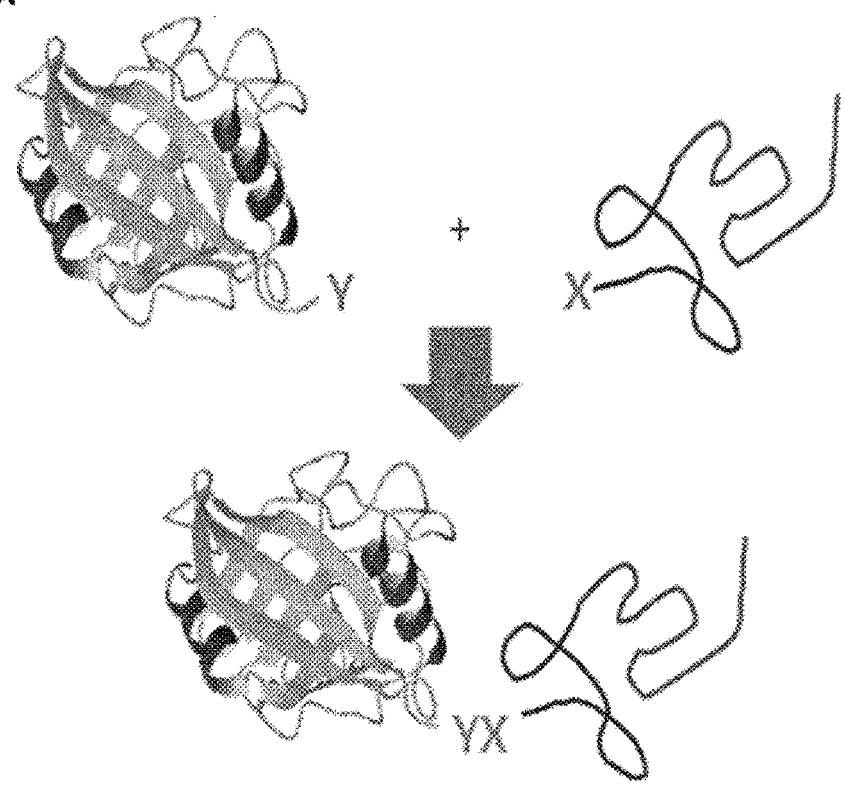
FIG. 1 is a schematic diagram according to one embodiment of the present invention showing (a) the formation of a polymer-protein hybrid through the binding of X and Y, both of which are functional groups specifically bound to each other, (b) the self-assembly of the polymer-protein hybrid, and (c) the formation of a polymer-protein hybrid through various bindings.

The first aspect of the present invention provides a method for preparing a protein cage which comprises: a $1^{st}$ step of preparing an amphiphilic polymer comprising a $1^{st}$ hydrophobic polymer and a $1^{st}$ hydrophilic functional group; a $2^{nd}$ step of preparing a hydrophilic protein comprising a $2^{nd}$ functional group binding to the $1^{st}$ functional group; a $3^{rd}$ step of forming an amphiphilic polymer-protein hybrid by the binding of the $1^{st}$ functional group and the $2^{nd}$ functional group, and forming core-shell structured particles comprising a protein shell and an amphiphilic polymer core by the self-assembly of the amphiphilic polymer in a hydrophilic solvent; and a $4^{th}$ step of removing some or all of the hydrophobic polymer of the core part from the core-shell structured particles.

The second aspect of the present invention provides the protein cage prepared by the method of the first aspect.

The third aspect of the present invention provides an in situ method for preparing hydrophobic additive-loaded core-shell structured polymer-protein particles which comprises: a $1^{st}$ step of preparing a $1^{st}$ solution comprising an amphiphilic polymer comprising a $1^{st}$ hydrophobic polymer and one or more $1^{st}$ hydrophilic functional groups and a hydrophobic additive in an organic solvent; a $2^{nd}$ step of preparing a $2^{nd}$ solution comprising a hydrophilic protein which carries a $2^{nd}$ functional group binding to the $1^{st}$ functional group while maintaining its tertiary structure in a hydrophilic solvent comprising water, and a $3^{rd}$ step of mixing the $1^{st}$ solution into the $2^{nd}$ solution, wherein, in a hydrophilic solvent, an amphiphilic polymer-protein hybrid is formed through the binding of the $1^{st}$ functional group and the $2^{nd}$ functional group, and at the same time the core-shell structured particles are formed by the self-assembly of the amphiphilic polymer to have the protein shell maintaining its tertiary structure and the core comprising the amphiphilic polymer and the hydrophobic additive.

The fourth aspect of the present invention provides the hydrophobic additive-loaded core-shell structured polymer-protein particles prepared by the method of the third aspect wherein the individual protein forming the shell maintains its tertiary structure.

The fifth aspect of the present invention provides a drug delivery system which comprises the protein cage described in the second aspect; and a drug enclosed inside the cage, interposed between the proteins, or bound onto the surface of the cage.

The sixth aspect of the present invention provides a cosmetic composition which comprises the protein cage described in the second aspect; and a cosmetic material enclosed inside the cage, interposed between the proteins, or bound onto the surface of the cage.

The seventh aspect of the present invention provides a composition for imaging which comprises the protein cage described in the second aspect; and a contrast agent enclosed inside the cage, interposed between the proteins, or bound onto the surface of the cage.

The eighth aspect of the present invention provides an artificial vaccine which comprises the protein cage described in the second aspect, wherein some or all of the proteins forming the protein cage are antigenic proteins.

The ninth aspect of the present invention provides a biosensor which comprises the protein cage described in the second aspect, wherein the protein comprises two or more types of proteins.

Below, the present invention will be explained in more detail.

The "protein cage" as used herein forms an outer surface of a specific structure through the gathering of two or more protein molecules, and it may be used interchangeably with the protein shell.

In addition, the explanation of the "protein cage" may be applied to the protein cage prepared in accordance with the first aspect of the present invention, as well as to the protein shell of the hydrophobic additive-loaded core-shell structured polymer-protein particles prepared in the third aspect.

A protein has a unique amino acid sequence. This sequence is called a primary structure and determines the structure and function of the protein. Through the interaction of amino acids, protein chains form a distinctive secondary structure, and in some cases a tertiary structure. The secondary structure is determined by the angle of peptide bonds linking amino acids to each other, and this bond angle is made by the hydrogen bond between the nitrogen atom of one amino acid and the oxygen atom of another amino acid. In general, these hydrogen bonds form the helical secondary structure. The tertiary structure is formed by folding and bending of the protein chain to form a more or less spherical protein. The tertiary structure is determined by the side chains of amino acids. There are side chains which are very bulky and thus destroy the normal secondary helical structure of the protein chain to cause bending or twisting. Also, the side chains form an ionic bond by attracting each other when they have different charge, and repel each other when they have the same charge. A water-insoluble hydrophobic side chain tends to gather inside the protein and to avoid the outer part which is exposed to water. A hydrophilic side chain easily makes a hydrogen bond with a water molecule and is located in the outer part. A disulfide bridge is a kind of covalent bond that is established between two cysteines, which are an amino acid containing sulfur (—S—). The disulfide bridge thus formed (—S—) stabilizes the loop structure of the protein chain.

The present invention utilizes the principle of manufacturing a hydrophobic polymer-hydrophilic protein hybrid core-shell structure by self-assembly in order to manufacture the protein cage artificially and to prepare the hydrophobic additive-loaded core-shell structured polymer-protein particles in situ in a one-pot reaction. The inventors have found that some or all of the polymers can be removed from the hydrophobic polymer-hydrophilic protein hybrid core-shell structure, during which the proteins constituting the shell maintain the shape of shell. They also have found that the polymer nanoparticles coated with protein are formed by the one-pot encapsulation method and at the same time the hydrophobic additive can be loaded by the hydrophobic polymer. Furthermore, they have found that, in a hydrophilic solvent (e.g., an environment appropriate for the physiological condition), the protein may be bound with the hydrophobic polymer while maintaining its tertiary structure, and formed the protein shell of the core-shell structure through self-assembly, and the hydrophobic additive may be collected in the core part simultaneously. The present invention is based on this discovery.

The method for preparing a protein cage according to the first aspect of the present invention comprises: a $1^{st}$ step of preparing an amphiphilic polymer comprising a $1^{st}$ hydrophobic polymer and a $1^{st}$ hydrophilic functional group; a $2^{nd}$ step of preparing a hydrophilic protein comprising a $2^{nd}$ functional group binding to the $1^{st}$ functional group; a $3^{rd}$ step of forming an amphiphilic polymer-protein hybrid by the binding of the $1^{st}$ functional group and the $2^{nd}$ functional group, and forming core-shell structured particles comprising a protein shell and an amphiphilic polymer core by the self-assembly of the amphiphilic polymer in a hydrophilic solvent; and a $4^{th}$ step of removing some or all of the hydrophobic polymer of the core part from the core-shell structured particles.

In addition, the in situ method according to the third aspect of the present invention for preparing hydrophobic additive-loaded core-shell structured polymer-protein particles comprises a $1^{st}$ step of preparing a $1^{st}$ solution comprising an amphiphilic polymer comprising a $1^{st}$ hydrophobic polymer and one or more $1^{st}$ hydrophilic functional groups and a hydrophobic additive in an organic solvent; a $2^{nd}$ step of preparing a $2^{nd}$ solution comprising a hydrophilic protein which carries a $2^{nd}$ functional group binding to the $1^{st}$ functional group while maintaining its tertiary structure in a hydrophilic solvent comprising water, and a $3^{rd}$ step of mixing the $1^{st}$ solution into the $2^{nd}$ solution.

The present invention is characterized in that the $1^{st}$ hydrophobic polymer carries the $1^{st}$ hydrophilic functional group to form the amphiphilic polymer, the hydrophilic protein carries the $2^{nd}$ functional group binding to the $1^{st}$ functional group, and the $1^{st}$ hydrophobic polymer is connected with the hydrophilic protein through the binding of the $1^{st}$ and the $2^{nd}$ functional groups to form the amphiphilic polymer-protein hybrid (FIG. 1A). The $1^{st}$ functional group must be hydrophilic to be able to guide the $1^{st}$ hydrophobic polymer to the interface of the hydrophilic solvent where the hydrophilic protein is included and to be easily bound to the $2^{nd}$ functional group of the hydrophilic protein in the hydrophilic solvent.

Figure 1B:
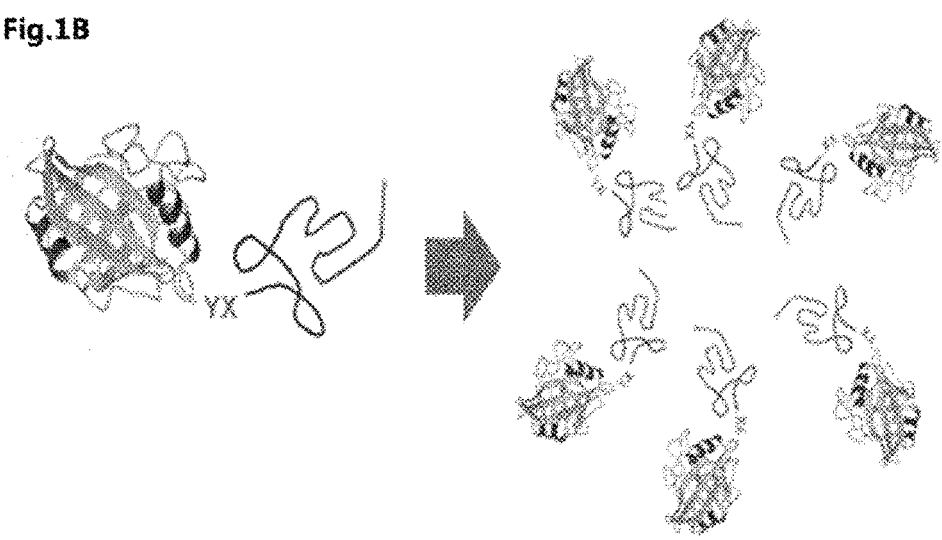

The present invention is also characterized in that the amphiphilic polymer-protein hybrid is formed through the binding of the $1^{st}$ and the $2^{nd}$ functional groups in the hydrophilic solvent, and at the same time the core-shell structured particles consisting of the protein shell and the core comprising the $1^{st}$ hydrophobic polymer are formed through the self-assembly of the amphiphilic polymer comprising the $1^{st}$ hydrophobic polymer part which tends to be aggregated in the hydrophilic solvent (FIG. 1B). Here, since the protein can maintain its own tertiary structure, it can still exhibit the activity of the protein itself.

In order to synthesize a well-defined core-shell structure, the amphiphilic polymer comprising a $1^{st}$ hydrophobic polymer and a $1^{st}$ hydrophilic functional group may comprise one or more $1^{st}$ hydrophilic functional groups, but it is preferable that the hydrophilic protein carries only one $2^{nd}$ functional group. This is because the orientation of hydrophilic protein in the protein cage or a protein shell can be controlled as desired when one $2^{nd}$ functional group is limitedly connected to a specific part of the protein.

In particular, in order to maintain the unique activity of protein in the protein cage or protein shell, it is better for the $2^{nd}$ functional group to be connected to a part that is not the protein active site, preferably to a three-dimensionally spaced part from the active site in order for the site not being sterically hindered. For example, the $2^{nd}$ functional group can be connected to the N- or C-terminal if the active site is not in the terminal.

With the preparation method according to the present invention, different proteins as well as the same proteins may co-exist and/or be concentrated in the protein shell part of the core-shell structure or in a certain space of a structure such as the protein cage. Thus, one type of protein may make up the protein cage or protein shell, but two or more types of proteins may be used in combination depending on the purpose.

If the self-assembled polymer-protein hybrid nanostructure is established according to the present invention, some biofunctionalities may be built into the nanostructure, and morphological architectures in various shapes may be formed. In particular, since the size and shape may be controlled during the formation of a polymer-protein hybrid nanostructure, this nanostructure may be applied to the field of a nanoreactor for a catalyst, as well as in the various biomedical science fields such as delivery of drugs, therapeutic agents, or diagnostic preparations.

A series of experiments have been performed by changing various parameters in order to control the size of polymer-protein hybrid aggregates and to understand the mechanism of the in situ method of preparing the polymer-protein hybrid aggregates for potential biomedical applications. For example, similar experiments have been performed by using His-tagged lipase instead of His6-GFP as a protein, using Ni-NTA-PS having a different molecular weight, changing the concentration of the polymer and/or protein solution, adjusting the rate of addition of the polymer solution, using a different solvent, or removing the organic solvent by dialysis.

As a result, the shape or size of the core-shell structured particles may be achieved by controlling the type/composition ratio, molecular weight, or concentration of the hydrophobic polymer; the type/composition ratio, molecular weight, or concentration of the protein; or the mixing ratio or mixing rate of the hydrophobic polymer and protein (Table 1). For example, as the ratio of the polymer and the protein changes, the rate of bond formation between the polymer and the protein and the rate of particle formation by self-assembly change, thereby determining the size of the finally generated core-shell structured polymer-protein particles. Here, the proteins have one $2^{nd}$ functional group which binds to the $1^{st}$ functional group for each molecule and are competitively bound. Therefore, when two or more proteins are used, it is possible to control the composition ratio of the protein that makes up the protein shell by adjusting mixing ratio thereof.

The core-shell structured polymer-protein particles formed according to the preparation method of the present invention may have an average diameter of 20 nm to 5 μm. In addition, the particles may be prepared in a spherical, oval, or rod shape, but the shape is not limited thereto.

In a case where a protein cage is prepared according to the present invention, it may be synthesized with a well-defined structure by a simple process, and few constraints on the selection and introduction of proteins make the cage available in various ways.

Furthermore, during the preparation of protein cage according to the present invention, the formation of particles coated by a protein and the encapsulation (loading) of the hydrophobic additive may be performed at the same time by a one-pot reaction. Thus, the process is very simple and can be effectively used in a variety of applications including delivery systems of drugs, cosmetic materials, etc. Also, few constraints on the selection of the substance to be loaded in the protein cage and the type of polymer used make it possible to select the substance from a wide range.

The $1^{st}$ functional group, the $2^{nd}$ functional group, or both may be connected directly or via a linker to the polymer and the protein, respectively.

Non-limiting examples of the binding between the $1^{st}$ functional group and the $2^{nd}$ functional group include a coordinate bond, a covalent bond, a metallic bond, a hydrogen bond, an ionic bond, an antigen-antibody binding, a ligand-receptor binding, etc. (FIG. 1C). The binding between the $1^{st}$ functional group and the $2^{nd}$ functional group is preferably specific.

Figure 4A:
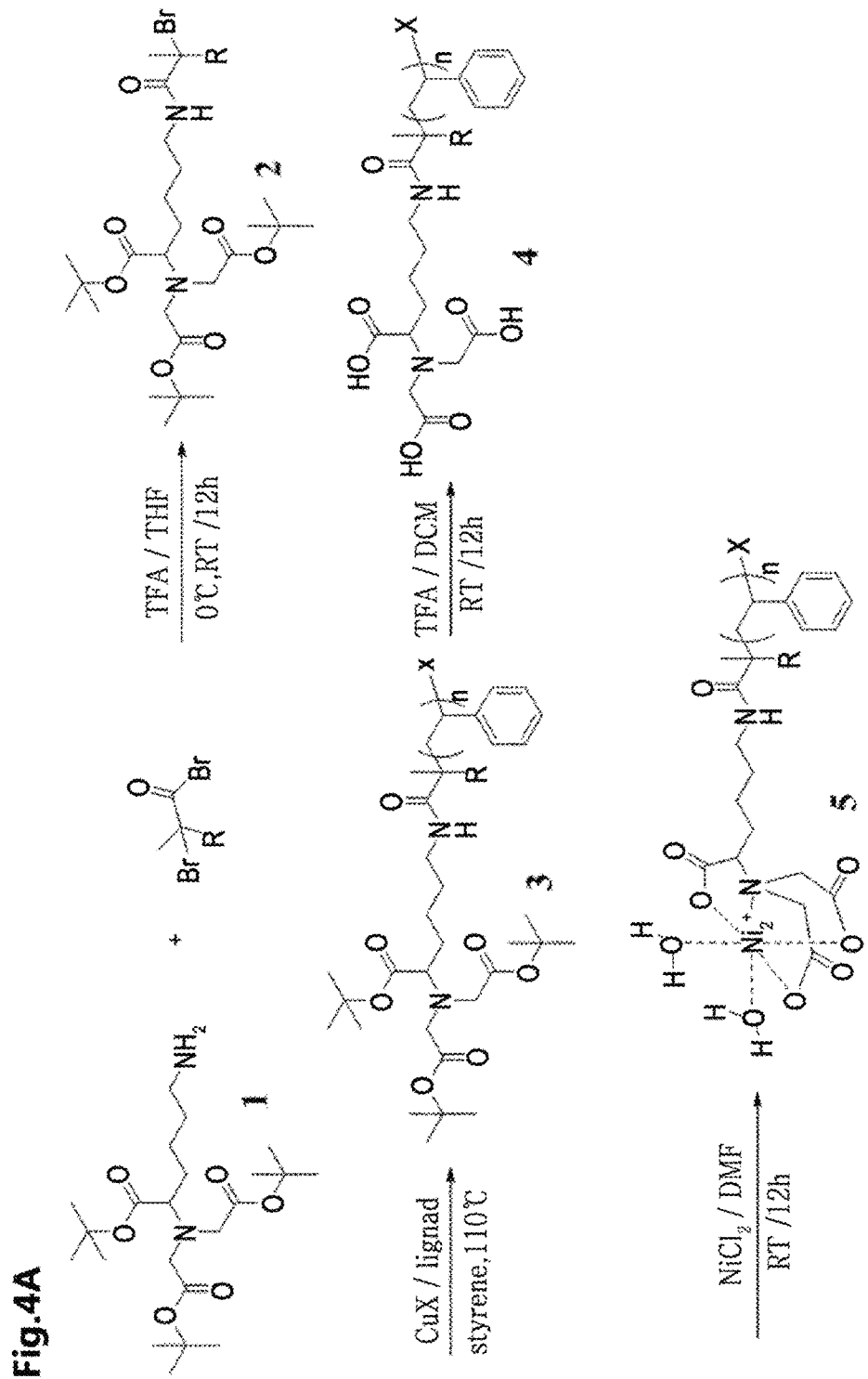
FIG. 4A illustrates the synthetic mechanism of the polymer wherein Ni-NTA is bound to its terminal according to Preparation Example 1.
Figure 4B:
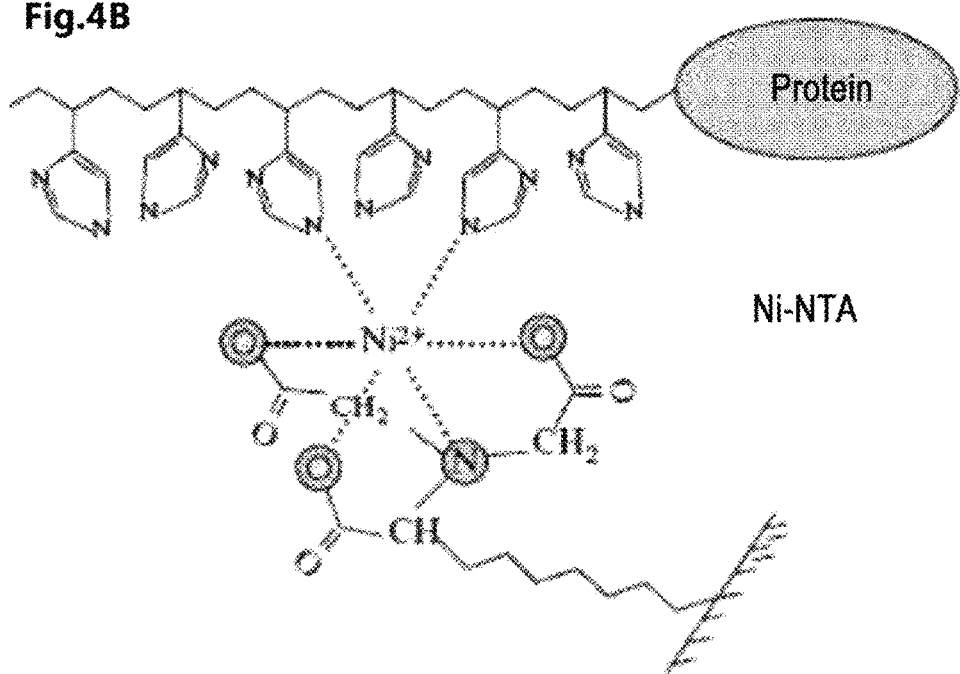
FIG. 4B is a schematic view illustrating a coordinate bond between the polymer comprising Ni-NTA at its terminal and the histidine-tagged protein according to one embodiment of the present invention.

A polymer having IMAL (immobilized-metal affinity ligand) at its terminal may be exemplified as the $1^{st}$ hydrophobic polymer having the $1^{st}$ functional group, and a protein to which the above IMAL-affinity tag is attached may be exemplified as the hydrophilic protein having the $2^{nd}$ functional group binding to the $1^{st}$ functional group. IMAL is a ligand containing a transition metal such as $Ni^{2+}$, $Co^{2+}$, $Zn^{2+}$, etc., preferably $Ni^{2+}$. As preferable examples thereof, Ni-NTA (nitrilotriacetic acid), Ni-IDA (iminodiacetic acid), Ni-TED (tris(carboxymethyl)ethylene diamine), etc. may be mentioned. Also, preferably, the IMAL-affinity tag may be a histidine tag having an imidazole ring, which is affinitive to the metal ion, at the side chain. The polymer-protein hybrid may be formed through a coordinate bond between the histidine tag and Ni-NTA (FIG. 4B).

Or, conversely, a polymer combined with histidine as the IMAL-affinity tag and a protein combined with IMAL may be used.

Other specific examples of the $1^{st}$ and the $2^{nd}$ functional groups that can be bound to each other include the covalent bond with NHS (N-hydroxysuccinimidyl 2-bromo-2-methyl propionate) and the ligand-receptor binding between biotin and avidin, etc. An NHS functional group may form a covalent bond with a primary amine. Thus, a polymer containing NHS may form a covalent bond via such amino acid residues as arginine, lysine, asparagine, glutamine, etc., each of which contains a primary amine in the side chain. Or, the protein modified to have the NHS functional group may form a covalent bond with a polymer containing a primary amine group. Meanwhile, the ligand-receptor binding between biotin and avidin may be achieved between a polymer modified with biotin and a protein containing avidin, or between a polymer and a protein conversely modified. Alternatively, since the avidin has a plurality of binding sites to biotin, it may be a form wherein the biotinylated polymer is bound to the protein through the avidin. The avidin includes avidin, streptavidin, and deglycosylated avidin (NeutrAvidin) without limitation.

In order to form the core-shell structured particle such as a micelle in a hydrophilic solvent through self-assembly, there is no limitation on types of the $1^{st}$ polymer and the protein in the present invention only if the $1^{st}$ polymer is hydrophobic enough to be aggregated in a hydrophilic solvent, the protein is hydrophilic enough to be dispersed or dissolved uniformly in the hydrophilic solvent, and the $1^{st}$ polymer and the protein have the $1^{st}$ functional group and the $2^{nd}$ functional group, respectively, that can be bound to each other.

The $1^{st}$ polymer is preferably a biocompatible and/or biodegradable polymer, and may be selected from polyglycolide (PGA), polylactide (PLA), polymethylmethacrylate (PMMA), polystyrene, poly(meth)acrylate (PMA), polycaprolactone (PCL), and derivatives thereof. Meanwhile, non-limiting examples of the monomer which forms the polymer include styrene, acrylate, lactide, hydroxybutyric acid, etc.

In the present invention, the protein includes a conjugated protein comprising a non-amino acid prosthetic group, as well as a simple protein consisting only of amino acids. As the prosthetic group, carbohydrates, lipids, nucleic acids, metals, pigments, etc. and some non-protein molecules, ions, etc. can be mentioned. Also, in the present invention, the protein includes structural proteins (e.g., collagen, keratin, etc.), biologically active proteins (enzymes, hormones, transport proteins of materials, immunoglobulins, etc.), and fragments of proteins (e.g., a variety of motifs such as enzyme active sites, binding sites, functional sites, etc.).

In addition, proteins, peptides, motifs, fusion proteins, peptide derivatives, proteins modified by PEG, etc., synthetic proteins, and natural proteins also belong to the category of the protein in the present invention. Even if the protein has a hydrophobic moiety within it, as long as the protein surface is hydrophilic and the protein can be uniformly dispersed in a hydrophilic solvent, it belongs to the category of the hydrophilic protein in the present invention. In particular, it is preferable that the hydrophilic protein has a hydrophilic property while maintaining its tertiary structure or the three-dimensional conformation in the hydrophilic solvent.

Non-limiting examples of the protein include human growth hormone, G-CSF (granulocyte colony stimulating factor), GM-CSF (granulocyte-macrophage colony-stimulating factor), erythropoietin, vaccines, antibodies, insulin, glucagon, calcitonin, ACTH (adrenocorticotropic hormone), somatostatin, somatotropin, somatomedin, parathyroid hormone, thyroid hormone, hypothalamus secrete substances, prolactin, endorphin, VEGF (vascular endothelial growth factor), enkephalin, vasopressin, nerve growth factor, non-naturally occurring opioid, interferon, asparaginase, alginase, superoxide dismutase, trypsin, chymotrypsin, pepsin, etc.

The hydrophilic solvent is not limited as long as the amphiphilic polymer-protein hybrid can form a core-shell structure through self-assembly. Non-limiting examples of the hydrophilic solvent include water or a solvent mixture thereof. However, it is preferable to use a solvent in which the tertiary structure of the protein, i.e., the activity of the protein can be maintained, more preferable to use a solvent having the pH and/or temperature range corresponding to the physiological conditions, and still more preferable to use a pH buffer (e.g., phosphate buffer solution) so that the shell-forming protein may form the protein shell under the circumstance where the protein can exert its own function.

The organic solvent is not limited as long as it can dissolve or disperse the amphiphilic polymer comprising the $1^{st}$ hydrophobic polymer and the $1^{st}$ functional group therein. Non-limiting examples of the organic solvent include a C1 to C6 alcohol, acetone, DMF (dimethylformamide), DMSO (dimethyl sulfoxide), THF (tetrahydrofuran), etc.

The organic solvent may be trapped in the core with the hydrophobic polymer during the formation of the core-shell particles. Thus, if a hydrophobic additive is dissolved or dispersed in the organic solvent, it may be trapped in the core with the organic solvent.

Based on the confirmation that the formation of (hydrophobic) polymer nanoparticles coated with a protein and the loading of a hydrophobic additive in the hydrophobic polymer can be simultaneously performed by a one-pot encapsulating method in a single step of mixing the $1^{st}$ and the $2^{nd}$ solutions, the third aspect of the present invention is characterized in that the hydrophobic additive to be loaded in the core part is further added to the $1^{st}$ solution having the amphiphilic polymer comprising the $1^{st}$ hydrophobic polymer and the $1^{st}$ hydrophilic functional group in an organic solvent in the in situ method for preparing the core-shell structured polymer-protein particles.

In addition, since the preparation method according to the third aspect of the present invention can manufacture the polymer-protein hybrid nanostructure by self-assembly in a hydrophilic solvent in an in situ one-pot reaction, the type, molecular weight, or concentration of the hydrophobic polymer; the type, molecular weight, or concentration of the protein; or the mixing ratio or mixing rate of the hydrophobic polymer and the protein may be controlled to adjust the shape and/or size of the particles formed. Thus, it is also another feature that the shape and/or size of the hydrophobic additive-loaded core-shell structured polymer-protein particles prepared by the in situ method according to the present invention can be adjusted.

Although the additive itself is hydrophilic, if the surface thereof is modified to be hydrophobic, it can be used as a hydrophobic additive.

The hydrophobic additive can be a drug, and thus particles loaded with the drug as a hydrophobic additive may be used as a drug delivery system. The earlier hydrophobic drugs are sparingly soluble and thus can hardly be administered. The present invention can address this problem by making the hydrophobic drug to be loaded in a particle having a surface coated with the hydrophilic protein. In particular, since the preparation method of the present invention proceeds in a single-step reaction wherein the hydrophobic drug is dissolved together with the polymer in an organic solvent and then mixed with a solution wherein the protein is dissolved in a hydrophilic solvent, it can provide a drug delivery system in the form of hydrophobic additive-loaded core-shell structured polymer-protein particles in a fast and convenient manner.

Non-limiting examples of the drug include anti-cancer agents such as paclitaxel, methotrexate, doxorubicin, 5-fluorouracil, mitomycin-C, styrene maleic acid neocarzinostatin, cisplatin, carboplatin, carmustine, dicarbazine, etoposide, daunomycin, etc.; anti-viral agents; steroidal anti-inflammatory drugs; antibiotics; antifungal agents; vitamins; prostacyclins; antimetabolic agents; cholinergic agents; adrenergic antagonists; anti-convulsants; anxiolytics; tranquilizers; antidepressants; anesthetics; pain relievers; anabolic steroids; immunosuppressive agents, immune enhancers, etc.

The hydrophobic additive may be a cosmetic material. The "cosmetic material" is defined as a material which is used for the human body to clean and beautify the body for the purpose of adding attractiveness, brightening the appearance, or maintaining or promoting the health of skin and hair, and has little action on the human body. Non-limiting examples of the cosmetic material include emollients, preservatives, fragrance substances, anti-acne agents, antifungal agents, antioxidants, deodorants, anhidrotic agents, anti-dandruff agents, decolorants, antiseborrheic agents, dyes, suntan lotions, UV light absorbers, enzymes, aroma substances, etc.

Likewise, the hydrophobic additive may be a contrast agent. The "contrast agent" is a substance that functions to provide a clear image for the sites that cannot be confirmed by simple imaging, thereby allowing early diagnosis and treatment of the disease occurring at those sites. Contrast agents for magnetic resonance imaging (MRI), computed tomography (CT), positron emission tomography (PET), ultrasonography, fluoroscopy, etc. may be used. Non-limiting examples of the contrast agent include those for magnetic resonance imaging (MRI) which are paramagnetic or superparamagnetic materials of transition metal ions such as gadolinium (Gd), manganese (Mn), copper (Cu), and chromium (Cr), hydrophobic complexes of the transition metal ions such as gadopentetate dimeglumine (Gd-DTPA) and gadoterate meglumine (Gd-DOTA), fluorine-containing compounds such as perfluorocarbons and perfluoropropane, iron oxide-, manganese-, copper-, and chromium-based nanoparticles, and nanoparticles whose surface is modified by hydrophobic substances; those for computed tomography (CT) which are iodinated hydrophobic material derived from iodinated poppy seed oil, nanoparticles consisting of a metal element comprising bismuth (Bi), gold (Au), silver (Ag), etc.; those for positron emission tomography (PET) which are radioactive isotopes comprising $^{99m}Tc$, $^{123}I$, $^{166}Ho$, $^{111}In$, $^{90}Y$, $^{153}Sm$, $^{186}Re$, $^{188}Re$, $^{68}Ga$, and $^{177}Lu$, and hydrophobic complexes of the radioactive isotopes prepared by using diethylene triamine pentaacetate (DTPA); those for ultrasonography which are hydrophobic compounds such as perfluoropropane, perfluorohexane, sulfur hexafluoride, perfluoropentane, decafluorobutane, etc.; and those for fluoroscopy which are fluorescein, rhodamine, Nile red, Cy-3, Cy-5, etc.

Ni-NTA is an example of the $1^{st}$ functional group in the $1^{st}$ hydrophobic polymer carrying the $1^{st}$ functional group. The synthesis mechanism of the polymer wherein Ni-NTA is bound to its terminal is schematically illustrated in FIG. 4A (Preparation Example 1). Meanwhile, FIG. 4C shows a schematic diagram of a process wherein the amphiphilic polymer-protein hybrid is formed through the binding of the $1^{st}$ and the $2^{nd}$ functional groups, and then the hydrophobic additive-loaded core-shell structured particles are formed by self-assembly of the hybrid in a hydrophilic solvent.

Referring to FIGS. 4A and 4C, an initiator of the R—X type having NTA is synthesized, a Ni-NTA-polymer is synthesized through ATRP living polymerization, and then a solution of the Ni-NTA-polymer and a hydrophobic material (Nile red) in DMF is added dropwise to a PBS buffer solution wherein the protein with a histidine tag is dissolved to form protein-coated polymer particles and concurrently to provide the hydrophobic material-loaded core. This action is caused by the interaction between the histidine tag and Ni-NTA as well as the aggregation of the polymer in water.

Figure 9:
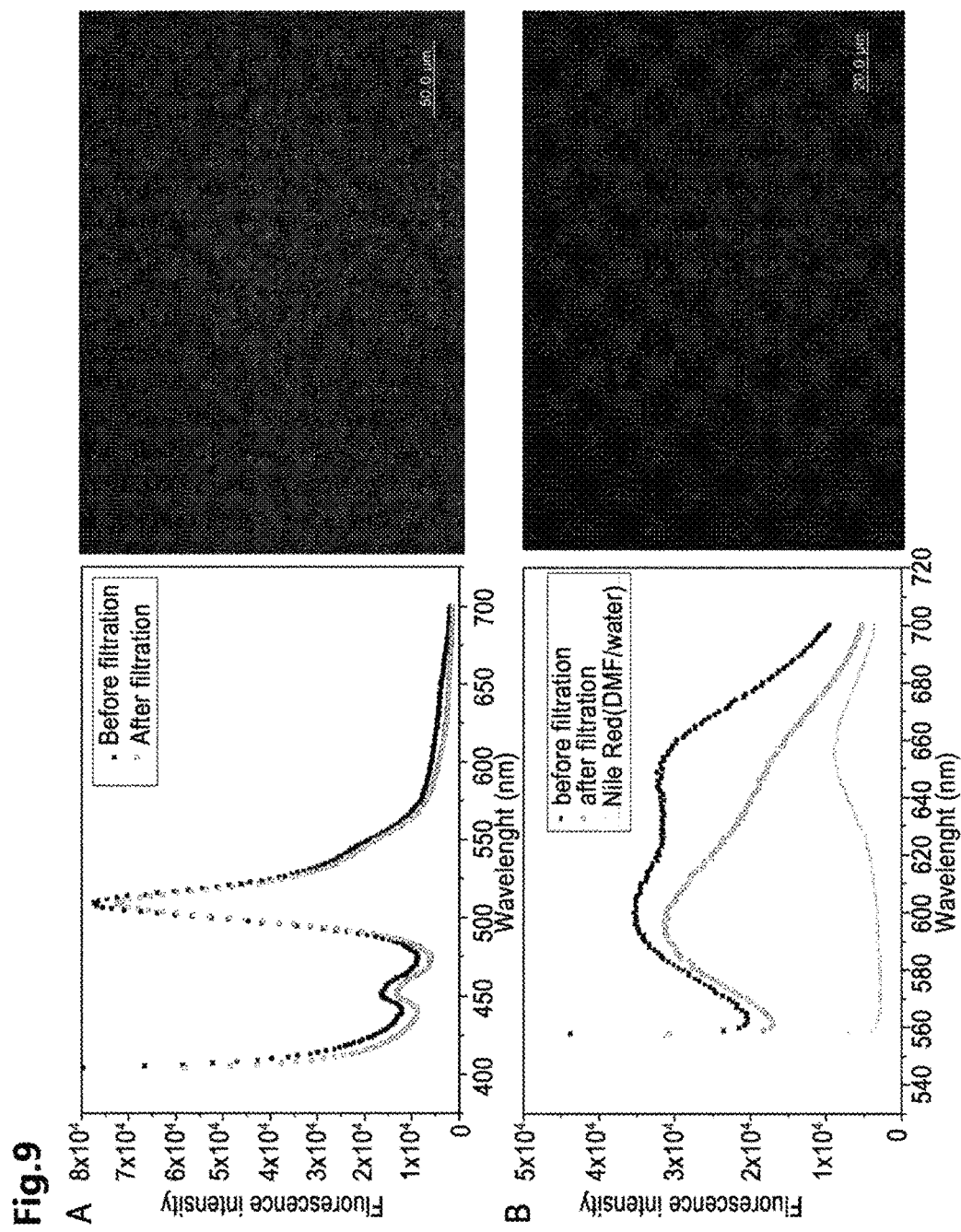
FIG. 9 shows the emission spectrum of the protein-coated polymer nanoparticles prepared in Example 5.

In an example of the present invention, the Nile red dye was used as a hydrophobic additive to confirm whether it is enclosed in the protein cage and the possibility of delivery into the inside of a cell (FIGS. 9 and 10).

In the present invention, a $2^{nd}$ hydrophobic polymer not having the $1^{st}$ functional group may be further added during the preparation of the core-shell structured polymer-protein particles. For this purpose, the $1^{st}$ solution used for the preparation of the core-shell structured polymer-protein particles according to the present invention may further comprise the $2^{nd}$ polymer not having the $1^{st}$ functional group.

The $2^{nd}$ hydrophobic polymer may be located together with the $1^{st}$ hydrophobic polymer in the core part of the core-shell structured particles to control the size of particles, and further it is not bound or less bound than the $1^{st}$ hydrophobic polymer to the amphiphilic polymer-protein hybrid, and can thereby be easily removed from the core-shell structured particles later. The $2^{nd}$ hydrophobic polymer may be the same as or different from the $1^{st}$ hydrophobic polymer. In short, the $2^{nd}$ hydrophobic polymer not having the $1^{st}$ functional group binding to the protein but having only the hydrophobic moiety of the $1^{st}$ polymer may be further added in preparing the core-shell structured polymer-protein particles in order to control the particle size and/or the number of proteins bound per single particle.

In addition, the preparation method according to the present invention may further comprise a step of forming bindings between shell-forming proteins by adding a cross-linking agent to the core-shell structured particles which are formed in the $3^{rd}$ step.

If a cross-linking agent is further added, cross-linking occurs between the proteins to further stabilize the core-shell particles and to make the encapsulation by the protein shell easier. As the cross-linking agent, glutaraldehyde, NHS ester, EDC, maleimide, pyridyl disulfide, hydrazide, alkoxy amines, etc. may be used.

The fourth aspect of the present invention is characterized in that it further comprises the $4^{th}$ step of removing some or all of the hydrophobic polymer of the core part from the core-shell structured particles in order to generate a protein cage.

Removal of some or all of the hydrophobic polymer of the core part from the core-shell structured particles may be performed by the introduction of (i) a competitor compound for the binding between the $1^{st}$ and the $2^{nd}$ functional groups, or (ii) a compound that hydrolyzes the polymer moiety in the amphiphilic polymer-protein hybrid.

Figure 11:
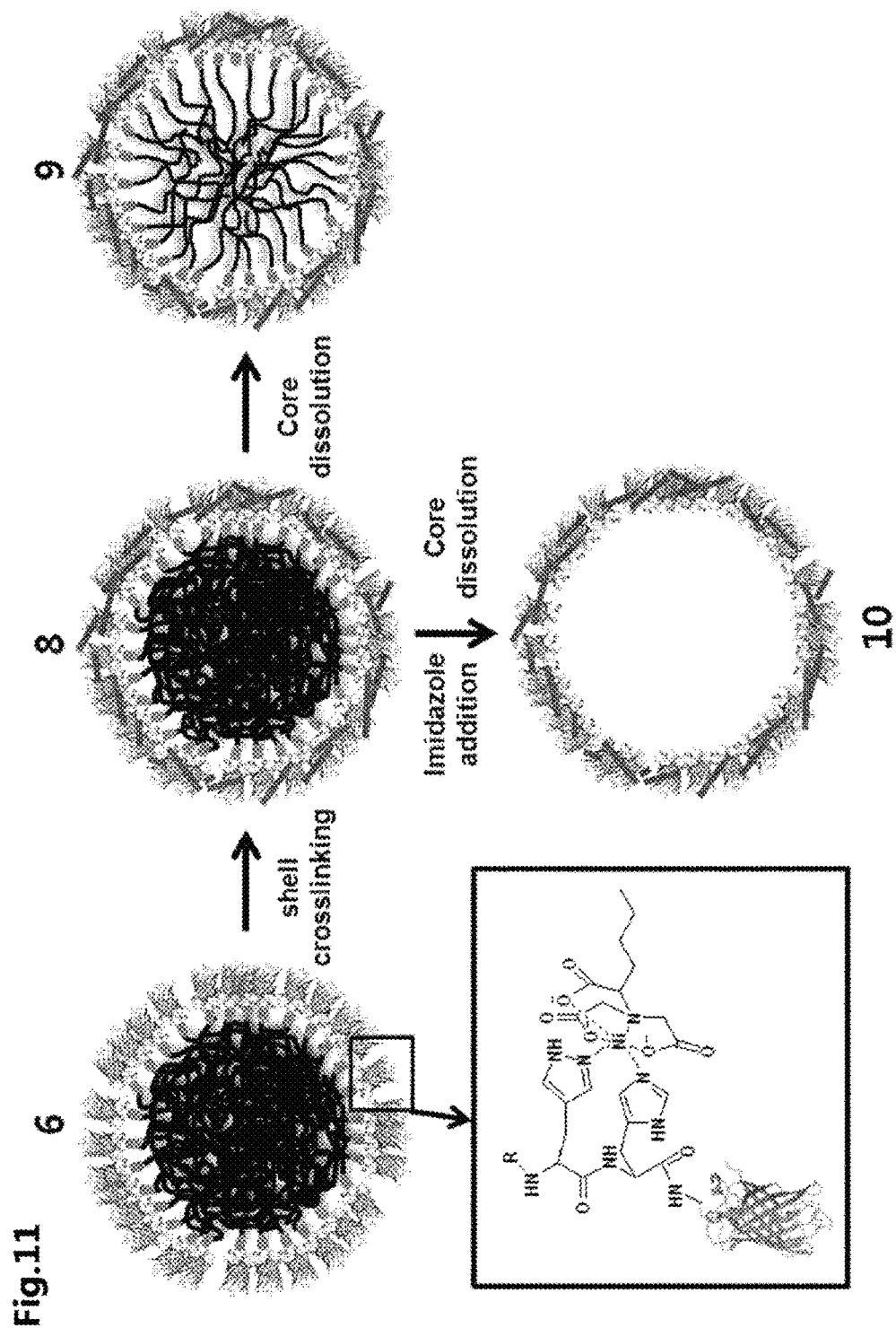
FIG. 11 is a schematic diagram showing the synthesis of the protein cage according to one embodiment of the present invention.

FIG. 11 shows a schematic diagram for the preparation of the protein cage according to one embodiment of the present invention. Protein-coated polymer particles are formed when a solution of the polymer with Ni-NTA at its terminal in DMF is added dropwise to a PBS buffer solution wherein the protein with a histidine tag is dissolved. The protein in the surface of the particles thus formed is cross-linked, and the particles are dissolved in an organic solvent to remove the inner polymer dissolved away to the outside of the particle. Here, a difference is observed depending on whether the binding between Ni-NTA and the histidine tag is dissociated or not. If an excess of imidazole is added to the solution and reacted, the excess imidazole is bound to IMAL competitively with the protein having an IMAL-affinity tag to replace the binding of polymer and protein, thereby eluting only the polymer from the core-shell particles.

As described above, in a case where the polymer and protein are connected by non-covalent binding in the amphiphilic polymer-protein hybrid, the binding may be easily dissociated by adding an excess of a material which can competitively replace the binding. Therefore, preferably, after the protein shell is cross-linked, the inner polymer is separated and removed by using the above competitive reagent to finally synthesize a protein cage.

Meanwhile, in a case where the polymer and protein are connected by a covalent bond in the amphiphilic polymer-protein hybrid, the polymer occupying the particle core may be removed by using a reagent, a solvent, or a solution containing it, each of which is capable of decomposing the polymer.

The protein cage which can be prepared according to the present invention may preferably have a diameter of 20 nm to 5 μm, but is not limited thereto. Also, the protein cage according to the present invention may have a spherical, oval, or rod shape.

Figure 2:
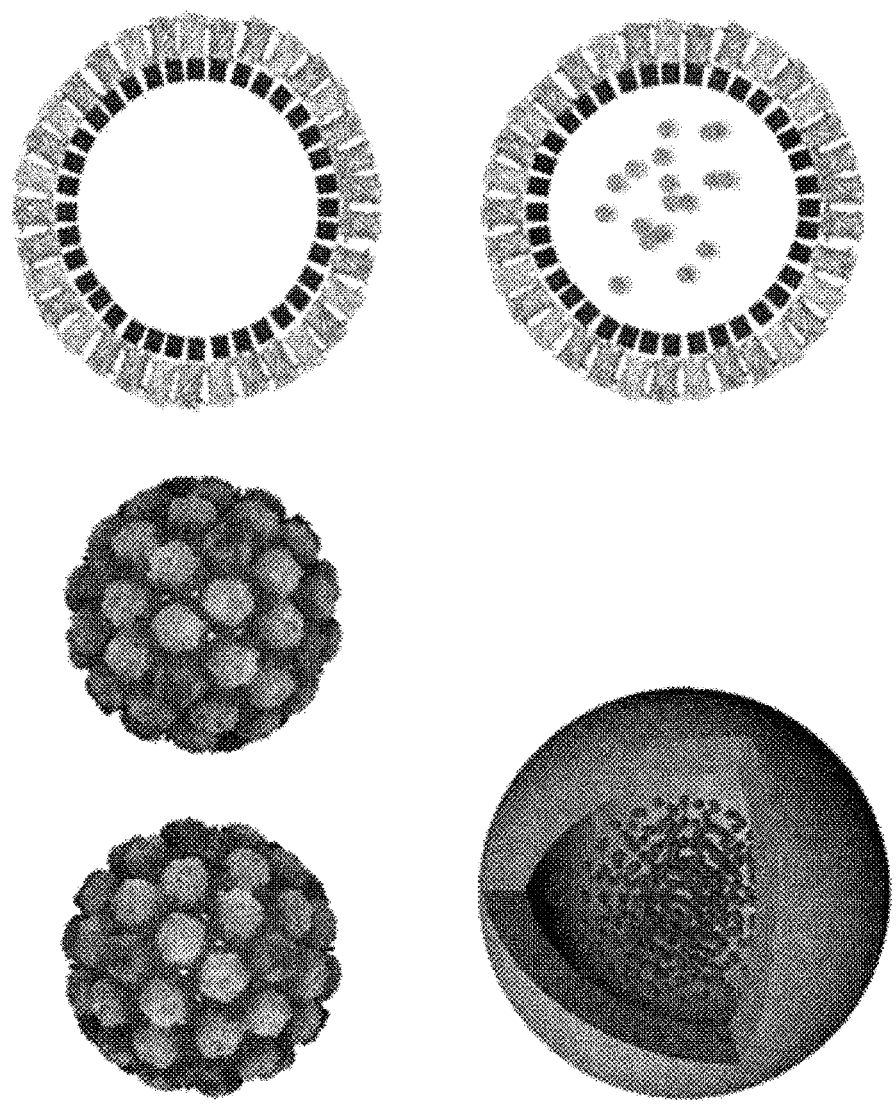
FIG. 2 is a schematic diagram of a protein cage which can be prepared according to one embodiment of the present invention.

The protein cage/protein shell prepared by the method of the first or the third aspect of the present invention can play a role as a nanostructure of a functional protein having a specific binding capacity, catalytic capacity, etc. For example, protein nanostructures having various functions may be provided depending on the selection of a structural protein of the cage (FIG. 2), and furthermore protein nanostructures that can be utilized in various applications such as a delivery system for an active component (physiologically active component, drug, etc.), a sensor, a catalyst, etc. may be provided depending on the function of the additive loaded (FIG. 3).

The protein cage according to the present invention can encapsulate a hydrophobic additive such as a sparingly soluble drug. The hydrophobic additive may be added in the $3^{rd}$ step to be loaded in the core part during the self-assembly, or may be injected into the protein cage formed in the $4^{th}$ step. When the additive is injected into the protein cage which is prepared according to the first aspect, it is not limited to the hydrophobic one, but a hydrophilic additive can be used.

Since the cage-forming protein can be a single protein or a multi-protein, it is possible to provide a cage having a monofunctional or multifunctional protein.

Non-limiting examples of the cage-forming protein include a sensor/reporter protein (sensor protein; e.g., green fluorescent protein), an enzyme (e.g., lipase, esterase, horseradish peroxidase), a target-oriented body protein (recognition protein), a vaccine protein (e.g., antigen, hemagglutinin), a skin-functional/permeable peptide, and derivatives thereof.

Thus, the protein cage according to the present invention can provide a vaccine superior to the virus-like particle (VLP) (fast responsiveness, reduced side effects), a biological target cell-oriented contrast agent, a protein carrier for a functional substance (drugs, functional substances for skin, healthcare compounds), or a target-oriented protein carrier for a functional protein (in the case of a multi-protein cage) by appropriately selecting the cage-forming structural protein.

The protein cage prepared by the method of the first aspect or the third aspect may be used for a drug delivery system which comprises a drug enclosed inside the cage, interposed between the proteins, or bound onto the surface of the cage; a cosmetic composition which comprises a cosmetic material enclosed inside the cage, interposed between the proteins, or bound onto the surface of the cage; or a composition for imaging which comprises a contrast agent enclosed inside the cage, interposed between the proteins, or bound onto the surface of the cage.

The drug is conventionally a substance showing a specific prevention or treatment effect against a specific disease, and it may show toxicity for normal cells other than the target tissue in some cases. Thus, delivering these drugs specifically to a site in need thereof is an important factor in minimizing side effects of the drug and maximizing a prevention or treatment effect thereof. Therefore, the protein making up the protein cage/protein shell may itself be a targetable protein, or may be a protein to which another antigen, antibody, ligand, or receptor being targetable is bound. In this case, targeting the drug contained therein to the desired site is possible. Also, when used as a composition for imaging, it is desirable that the protein making up the protein cage/protein shell is itself a protein being targetable or a protein to which another antigen, antibody, ligand, or receptor being targetable is bound, in order for it to be specifically moved to the tissue to be imaged, like a drug delivery system.

Meanwhile, it is preferable that the cosmetic material can be delivered inside the skin by passing through the epidermal layer in order to show the effect when applied to the skin. Thus, to effectively deliver the cosmetic material inside the skin, the protein making up the protein cage/protein shell is itself a protein having skin permeability or is a protein to which a skin-permeable peptide or compound is bound.

Skin-permeable peptides that can be used to promote skin permeation are exemplified in U.S. Pat. No. 7,659,252 (incorporated in the present specification). These peptides exhibit an excellent skin permeation rate, and further can be used as a carrier for the transdermal delivery of other drugs.

The protein cage prepared by the method of the first aspect or the third aspect can be used as an artificial vaccine when some or all of the proteins are an antigenic protein. Since the protein cage according to the present invention is much larger in size than the individual protein, it has an excellent immunity as a vaccine. In addition, the vaccine production time can be reduced, rapid development of the vaccine is possible, the particle size can be adjusted, and the potential to cause immune side effects may be reduced.

An example of the artificial vaccine that can be prepared according to the present invention is schematically depicted in FIG. 3. For example, if the self-assembled protein cage according to the present invention is prepared using the HA/NA antigenic protein as an influenza surface protein, it is possible to provide a highly efficient influenza preventive vaccine.

Also, the protein cage prepared by the method of the first aspect or the third aspect may include such proteins as enzymes, antigens, antibodies, ligands, or receptors which cause some physico-chemical changes in the substance to be detected or undergo some physico-chemical changes by the substance to be detected, and thus may be used as a biosensor. If appropriate, two or more types of proteins may be used as the protein. For example, the protein cage according to the present invention may provide a sensor in the form that the proteins for detection such as enzymes are fixed on the spherical support. Furthermore, a coenzyme or a material to be further required in a reaction may be loaded inside of the cage, thereby representing a relatively high concentration thereof in the cage and thus showing the effect of enhancing the local signal.

The glucose enzyme sensor is an example of a biosensor, and is based on the phenomenon that glucose is converted to glutamic acid by the glucose oxidase with consuming oxygen and generating hydrogen peroxide. Therefore, the biosensor works in the manner of measuring the increase in the amount of charge, the pH change, the reduced amount of oxygen, etc. generated by the secondary oxidation of hydrogen peroxide. Such reactions of consuming oxygen and generating hydrogen peroxide as a by-product are typical ones by a variety of oxidases (e.g., galactose oxidase, lactate oxidase, cholesterol oxidase, etc.) besides the glucose oxidase. Thus, the protein cage according to the present invention may be prepared to be used as a sensor, that is, it may be a component of a product utilized as the existing biosensor in such a manner that an enzyme is suspended in a solution or supported/fixed on a membrane or a support. As described above, since the protein cage prepared in this way can fix tens to thousands or more of enzymes in a particle, it may show the effect of enhancing the local signal and effectively detect even a small amount of sample.

An illustrative example of a sensor utilizing a protein cage containing a heterologous protein may be the case wherein a peroxidase using hydrogen peroxide generated from the oxidase reaction is further contained in addition to the oxidase. Since the peroxidase converts the substrate compound to a colored product, it is possible to determine the activity of the oxidase by measuring the color change. In this case, the substrate compound of peroxidase may be enclosed inside the protein cage for efficient detection.

Preferably, the biosensor may further have a detector. The detector may be an electrochemical signal detector, an optical detector, a pH detector, a gas detector, etc., each of which is known in the art, without limitation.

MODE FOR INVENTION

Hereinafter, the present invention will be explained in more detail by the following examples. These examples are intended to illustrate the present invention more specifically, but the scope of the present invention is not limited thereto.

PREPARATION EXAMPLE 1

Preparation of Polymer with NI-NTA at its Terminal

A polymer having Ni-NTA at its terminal was synthesized as depicted in FIG. 4(A).

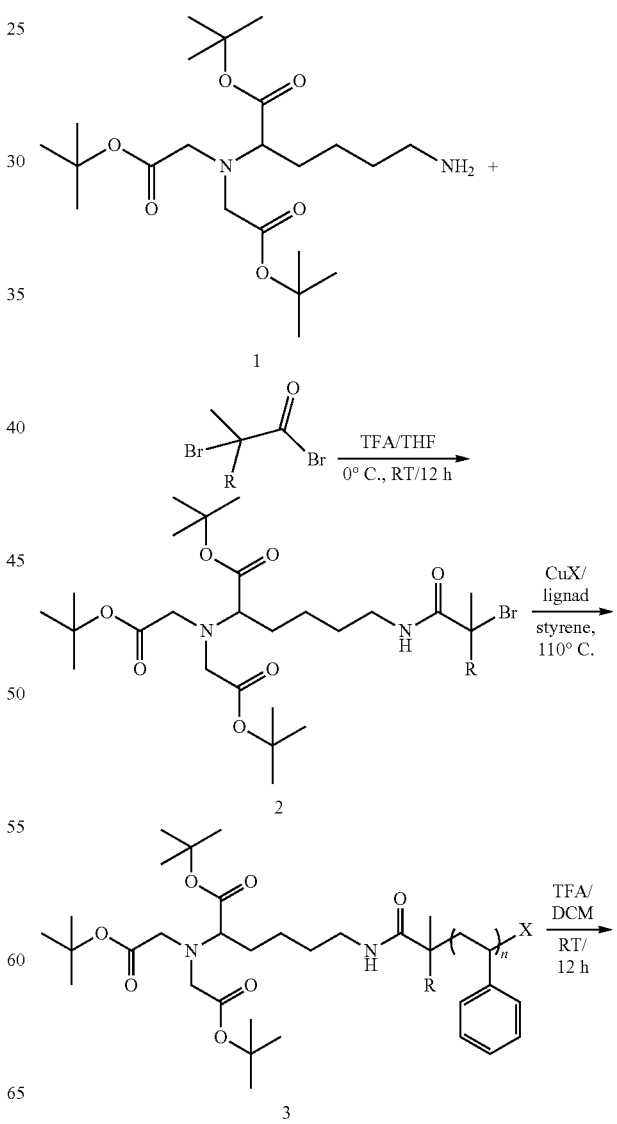

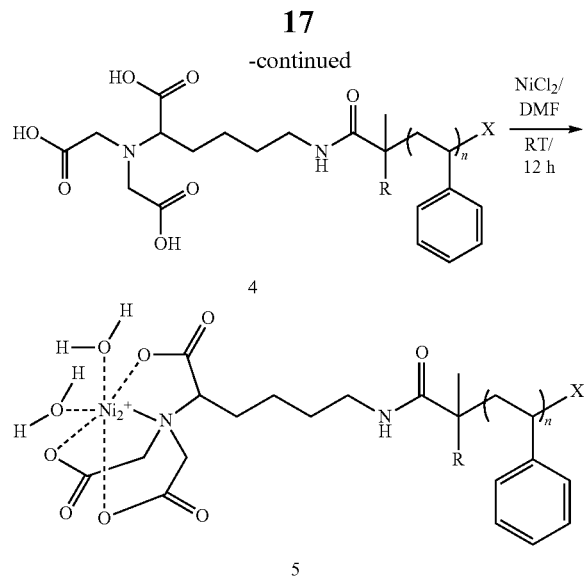

1.1. Synthesis of NTA Initiator (2)

2-Bromoisobutyryl bromide (0.09 mL, 0.85 mmol) was slowly introduced to a flask charged with Compound 1 (N-(5-amino-1-carboxypentyl)iminodiacetic acid tri-t-butyl ester, 342 mg, 0.77 mmol), triethylamine (0.32 mL, 2.3 mmol), and THF (50 mL) at 0° C. for 1 h. After introduction of the acid bromide was completed, the reaction mixture was reacted at room temperature for 12 h, THF was removed, and the reaction mixture was dissolved in 100 mL of methylene chloride and washed with distilled water (5×100 mL). The product was purified by column chromatography (hexane:ethyl acetate=4:1). The structure of the product was analyzed by $^1$H NMR.

$^1$H NMR (300 MHz, CDCl$_3$): δ 1.38 (s, 18H), 1.40 (s, 9H), 1.49 (m, 2H), 1.60 (m, 2H), 1.65 (m, 2H), 1.88 (s, 6H) 3.20 (t, 2H), 3.25 (t, 1H), 3.42 (dd, 4H).

1.2. Preparation of NTA-Functionalized Polystyrene (3)

Styrene (1.00 mL, 8.82 mmol, 104 g/mol) and anisole (1.00 mL) were introduced to a Schlenk flask charged with nitrogen, three cycles of a freeze-pump-thaw process were repeated, CuCl (36.4 mg, 0.368 mmol) and dNbpy (300.8 mg, 0.736 mmol) were added to the flask, and then two cycles of the freeze-pump-thaw process were further performed. The flask was placed in an oil bath at 110° C., and then the NTA initiator 2 (106.5 mg, 0.184 mmol) was added to the reaction mixture. After the polymerization was completed, Compound 3 was obtained by precipitation from methanol (Mn=6500 g/mol).

1.3. Removal of Protecting Group of (3) (4)

Compound 3 (300 mg, 0.06 mmol) and trifluoroacetic acid (0.14 mL, 1.86 mmol) were dissolved in 20 mL of methylene chloride and then reacted at room temperature for 12 h. After the solvent was removed, Compound 4 was obtained by precipitation from methanol.

1.4. Formation of Complex with Nickel (5)

Compound 4 (100 mg, 0.02 mmol) was dissolved in 50 mL of DMF, nickel chloride (54.4 mg, 0.42 mmol) was added thereto, and the reaction for forming a complex with nickel was performed at room temperature for 12 h. The reaction mixture was precipitated from methanol to give Product 5.

EXAMPLE 1

Preparation of Protein-Coated Polymer Nanoparticles (6) by Coordinate Bond and Determination of Size of Protein-Coated Polymer Nanoparticles The product (5) (0.1 mg, 1.5×10$^{-5}$ mmol) prepared in Preparation Example 1 was dissolved in 0.2 mL of DMF, and the solution was added dropwise to 5 mL of a phosphate buffer solution (10 mM, pH 7.5) containing His6-GFP (0.41 mg, 1.4×10$^{-5}$ mmol), using a syringe pump at a rate of 0.02 mL/h at room temperature. After addition over 10 h, the reaction mixture was stirred for 1 day.

Preparation of TEM Sample

Carbon-coated copper grid was soaked in the solution comprising the protein-coated polymer nanoparticles prepared in Example 1 to prepare the TEM sample. The excess solution was removed with the filter paper, and the grid was dried at room temperature for 6 h. The sample was not stained.

Preparation and Measurement of DLS Sample

A DLS test was performed for the protein-coated polymer nanoparticles prepared in Example 1 utilizing a laser operating at 660 nm and an optimized self-constructed setup. DLS samples were prepared by diluting each sample 10- or 20-fold with water-DMF (DMF 4 vol. %, pH 7.4). The above samples were loaded in spherical glass cuvettes before measurement. All measurements were performed at 25° C. at 900. Each measurement was the sum of 5 repetitions, and the single measurement time was 1 min. The size of acquired hybrid particles was presented as a number distribution.

FIG. 6 shows the TEM analysis results (A, B) and DLS data (C) to verify the formation of the protein-coated polymer nanoparticles according to Example 1. As shown in TEM photograph (A), nanoparticles of uniform shape were formed, and upon magnifying (B), it could be found that particles were formed with a uniform shape inside and outside of the particles, and the contrasts of the inside and outside of the particles were different. In addition, DLS data (C) showed that there were particles of uniform size with a narrow distribution.

Meanwhile, the stability of the polymer-protein hybrid aggregates is an important factor in potential applications thereof in the biological field. In order to study the stability of the hybrid aggregates acquired from Ni-NTA-PS (Mn of approx. 21,800) and His6-GFP, the solution containing the polymer-protein hybrid colloid was continuously stirred, and DLS measurements were performed at uniform time intervals up to 1 month. DLS and TEM studies showed that the aggregates appeared to be stable up to 15 days and degraded thereafter without phase separation (precipitation).

EXAMPLE 2

Figure 5:
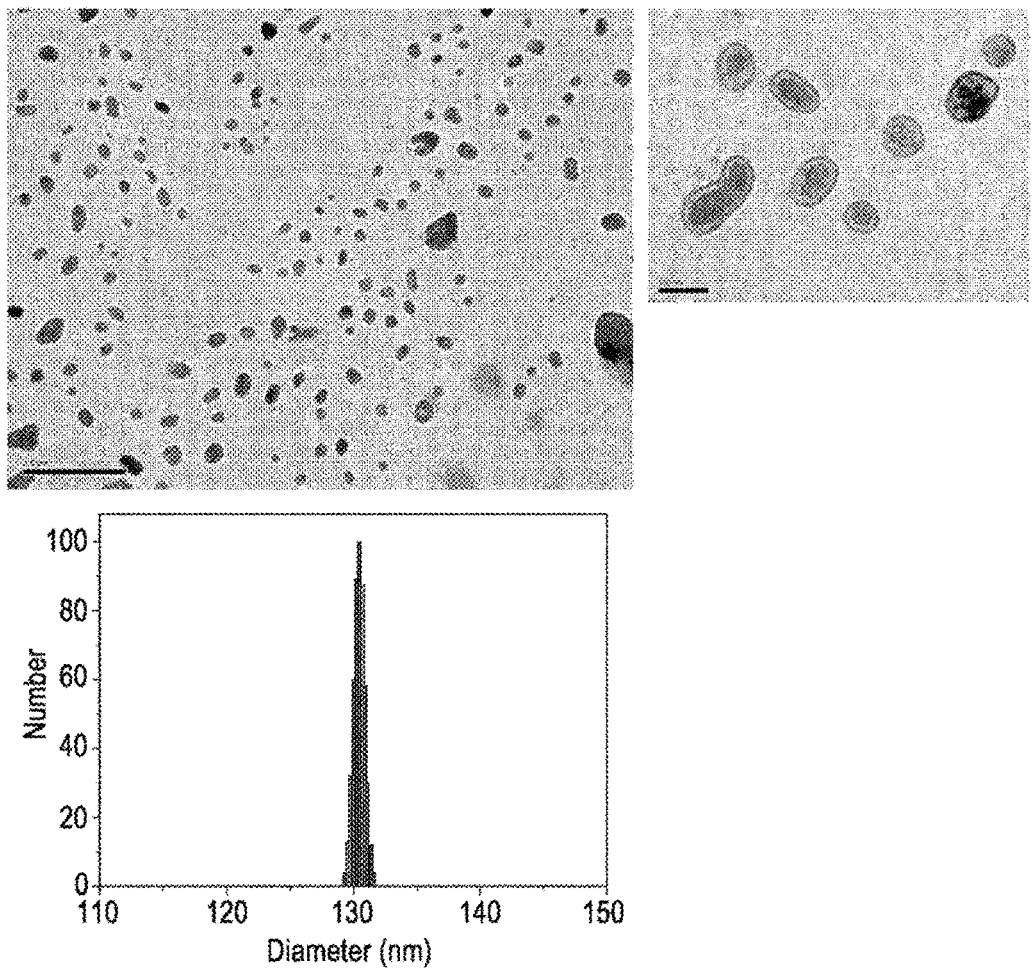
FIG. 5 shows TEM analysis results (top) and DLS data (bottom) of the protein-coated polymer nanoparticles prepared in Example 2.

FIG. 5 shows the TEM analysis results (top) and DLS data (bottom), which confirmed that polystyrene particles bound with Ni-NTA were formed uniformly when polystyrene bound with Ni-NTA at its terminal (0.1 mg, $1.5 \times 10^{-5}$ mmol) and Nile red (0.02 mg, $6.3 \times 10^{-5}$ mmol) dissolved in 0.2 mL of DMF were slowly added dropwise to 5 mL of a PBS buffer solution containing His6-GFP (0.41 mg, $1.4 \times 10^{-5}$ mmol), a protein having a histidine tag. As shown in the TEM photograph, it can be found that polystyrene particles were formed in a uniform size and stabilized as the proteins were bound to these particles. In addition, DLS data showed that there were particles of uniform size.

EXAMPLE 3

Size of the resulting aggregates was determined, which changes according to the amount of the polymer dissolved in an organic solvent, unlike Example 1.

Figure 7:
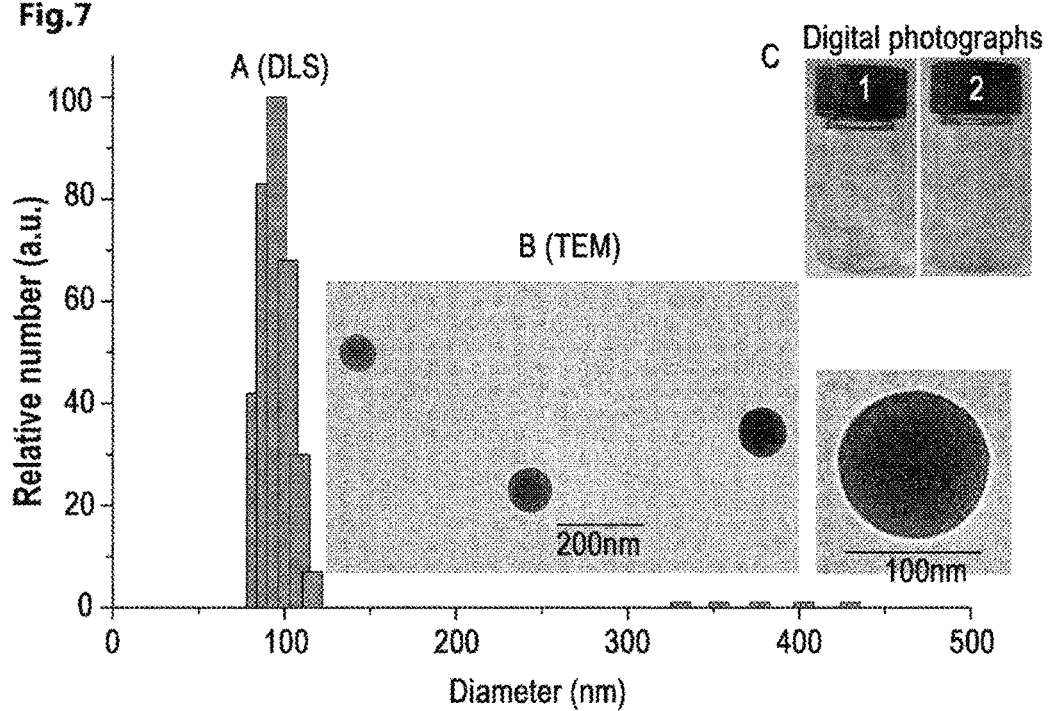
FIG. 7 shows the size and shape of the polymer-protein particles prepared in Example 3.

0.25 mg of Ni-NTA-PS (Mn of approx. 21,800, $1.2 \times 10^{-5}$ mmol) was dissolved in 0.2 mL of DMF, and the above polymer solution was slowly added to 5 mL of deionized water containing His6-GFP (27 kDa, 261 mg, $9.8 \times 10^{-6}$ mmol) at a rate of 0.02 mL/h to prepare the aggregates. The shape and size of the prepared aggregates were measured and presented in FIG. 7. Under the reaction conditions described above, spherical aggregates having a size of 80 nm to 140 nm were formed, and the DLS data and the representative TEM image were shown in FIGS. 7A and 7B.

FIG. 7C is digital photographs showing the aqueous His6-GFP solution (pH 7.4) before the addition of Ni-NTA-PS dissolved in DMF (1) and the colloidal solution of polymer-protein particles prepared by the addition of Ni-NTA-PS dissolved in DMF (2). The polymer-protein hybrid colloidal solution became less transparent compared to the His6-GFP solution due to the formation of aggregates (FIG. 7C).

When the experiment was performed without His6-GFP, although the reaction was carried out under the same experimental condition, Ni-NTA-PS itself formed ill-defined large amorphous aggregates, whereas when the DMF solution of polystyrene modified by the nickel-complexed NTA at its terminal (Ni-NTA-PS) was slowly added to the aqueous solution (pH 7.4) containing His6-GFP using a syringe pump, spherical aggregates were found to be produced due to the specific interactions between the protein and the polymer.

EXAMPLE 4

Preparation of Enzyme-Coated Polymer Nanoparticles

Enzyme-coated polymer nanoparticles were prepared by a method similar to that described in Example 1.

Specifically, polystyrene modified by the nickel-complexed NTA at its terminal (Ni-NTA-PS, Mn of approx. 21,800, 0.0625 mg, $3.0 \times 10^{-6}$ mmol) was prepared by stepwise dilution in 0.05 mL of DMF. In a glass vial under agitation, the polymer solution was slowly added to 1.25 mL of deionized water containing His-tagged enzyme (His6-Lip21H, 37 kDa, 77.5 mg, $2.1 \times 10^{6}$ mmol) at a rate of 0.02 mL/h using a syringe pump at room temperature (22° C.). Several drops of phosphate buffer saline (PBS, 50 mM, pH of approx. 7.4) were added to maintain the pH at 7.4 before the polymer solution was added to a water-soluble enzyme solution. After the addition of the polymer solution was completed, the resulting polymer-enzyme hybrid solution was continuously stirred, and the self-assembled form was analyzed by DLS and TEM. Next, a similar process was performed for the conjugation with His6-Lip83H (27 kDa).

DLS and TEM analysis results for the above prepared enzyme-coated polymer nanoparticles were presented in FIGS. 8. (A) and (B) are the results for the particles prepared utilizing His6-Lip21H (37 kDa) and His6-Lip83H (27 kDa) as the histidine-tagged enzyme, respectively. As shown in FIG. 8, His6-Lip21H (FIG. 2A; 37 kDa)-coated particles exhibited the size distribution in the range of 90 nm to 150 nm, and His6-Lip83H (FIG. 2B; 27 kDa)-coated particles exhibited the size distribution in the range of 70 nm to 120 nm, which was somewhat lower than the former.

EXAMPLE 5

Hydrophobic Dye-Loaded Protein-Coated Polymer Nanoparticles (6)

The product 5 (0.1 mg, $1.5 \times 10^{-5}$ mmol) prepared in Preparation Example 1 and Nile red (0.02 mg, $6.3 \times 10^{-5}$ mmol) were dissolved in 0.2 mL of DMF, and this solution was added to 5 mL of a phosphate buffer solution containing His6-GFP (0.41 mg, $1.4 \times 10^{-5}$ mmol), using a syringe pump at a rate of 0.02 mL/h at room temperature. After addition over 10 h, the reaction mixture was stirred for 1 day, and the Nile red which had not been encapsulated was removed using a 200 nm membrane syringe filter.

FIG. 9 shows the results of emission spectrum measurements, from which it was confirmed that Nile red has the characteristic of its wavelength range being shifted to a short-wavelength region when it is loaded (FIG. 9b). If unloaded Nile red was removed through filtration, the peaks of a long-wavelength region disappeared and GFP appeared to retain its fluorescence during the process (FIG. 9a). Also, Nile red was confirmed by fluorescence microscopy to remain even after the filtration.

In order to investigate whether the particles prepared in Example 5 can enter the inside of the cell, observation by fluorescence microscopy was conducted. As depicted in FIG. 10, the presence of both GFP and Nile red was confirmed, which exhibit intracellular green fluorescence and red fluorescence, respectively.

EXAMPLE 6

Cross-Linking of Protein Coating Shell of Protein-Coated Polymer Nanoparticles (8)

0.1 mL of a 2.5% glutaraldehyde aqueous solution was injected into the solution prepared according to Example 1 using a syringe pump for 30 min at room temperature. After 30 min, the reaction was stopped using sodium borohydride.

FIG. 12 shows the TEM analysis results (top) and DLS data (bottom right) after the addition of a cross-linking agent (glutaraldehyde) to the solution in which the core-shell structured polymer-protein particles had formed. As shown in the TEM photograph, cross-linking of proteins occurred, the particles thereby became more stable, and subsequent purification through a centrifugal filter removed the reactants, buffer ions, etc., giving a clean solution where only particles were present in the water phase.

EXAMPLE 7

Preparation of Protein Nanocage (9) (10)

Figure 13:
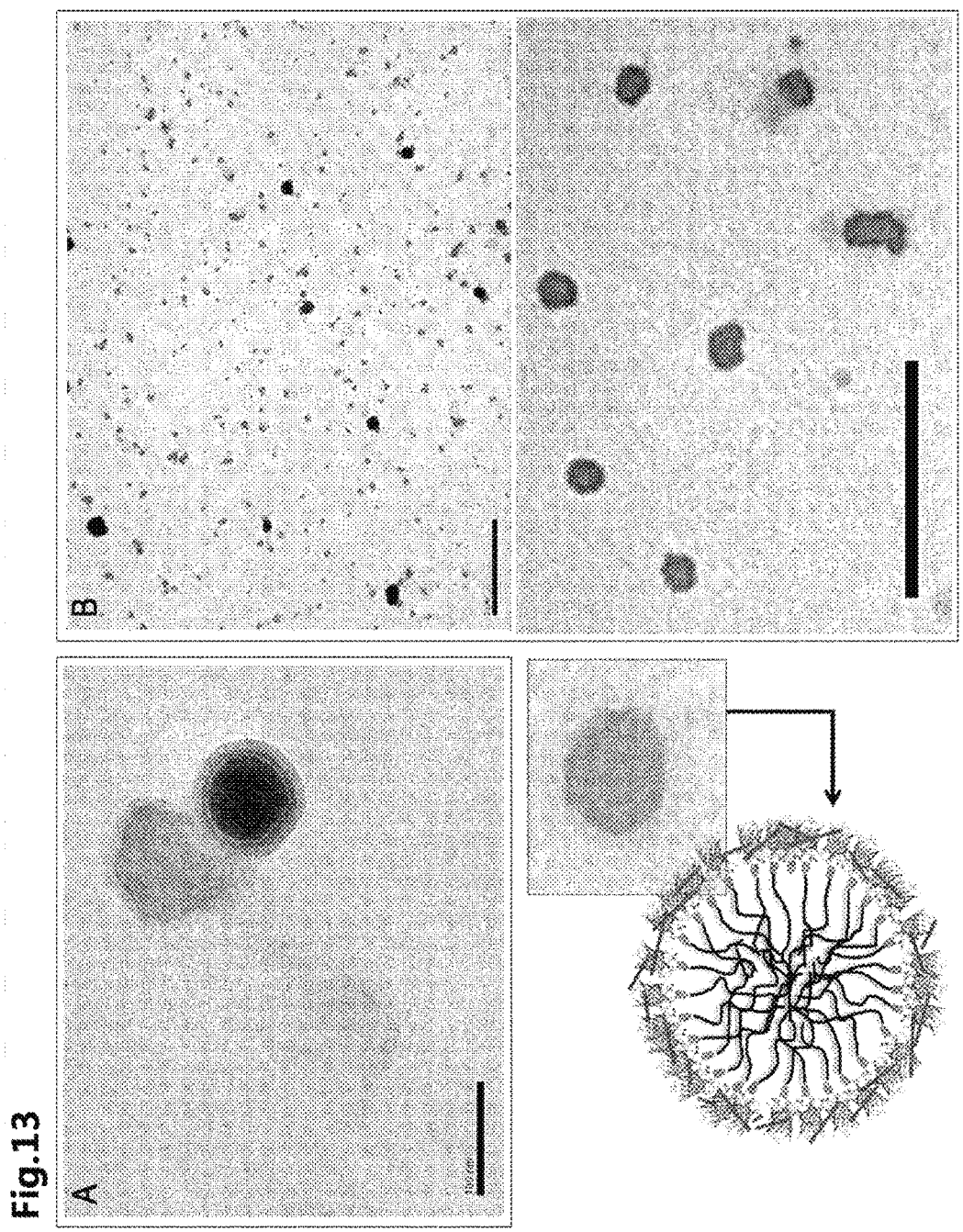
FIG. 13 shows the TEM image and schematic view after the addition of THF to the cross-linked structure as confirmed in FIG. 12.

FIG. 13 shows the TEM photograph and schematic diagram (9) after the addition of THF to the cross-linked structure confirmed in FIG. 12. Here, the polystyrene which had aggregated inside the cross-linked structure was eluted out by the addition of THF, but at this time, the polymer bound to the protein still remained inside the structure.

Excess imidazole was added to the solution prepared according to Example 6 to dissociate the interaction between Ni-NTA and a histidine tag. An equal volume of THF was added and stirred for 1 week to stabilize the hollow protein nanocage (10).

Figure 14:
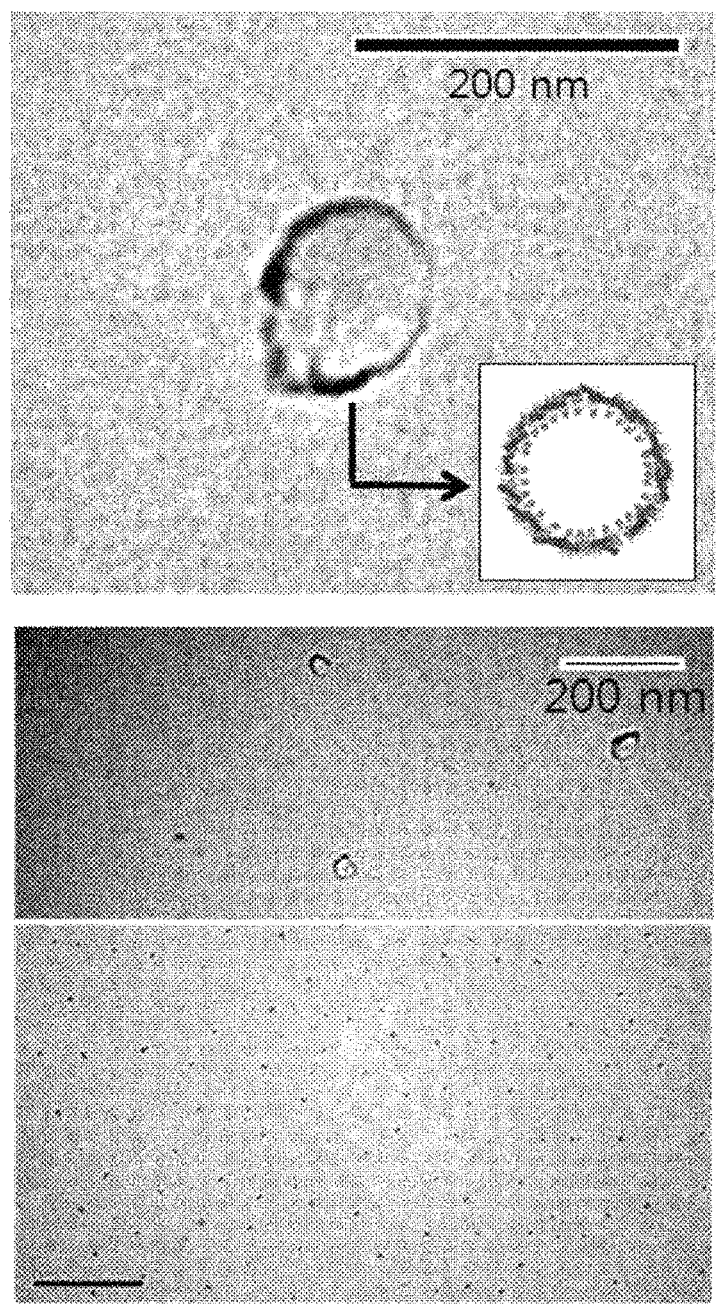
FIG. 14 shows the TEM image and schematic view after an excess of imidazole is added when the inner polymer is melted out, as in FIG. 13, according to Example 7.

FIG. 14 shows the TEM photograph and schematic diagram (10) after the addition of excess imidazole when eluting the inside polymers as in FIG. 13. Here, it was confirmed that the addition of excess imidazole dissociated the binding between the polymer and protein, and thereby all the residual polymers which had been bound to the protein-coated shell were eluted out of the structure.

EXAMPLE 8

Effects of Solvents on Stability of Protein-Coated Polymer Particles and Protein Cage The effects of solvents (DMF and THF) on the self-assembly of the polymer-protein hybrid aggregates were investigated. Upon the addition of Ni-NTA-PS (Mn=21,800) in each solvent to the deionized water (pH 7.4) containing His6-GFP, the water-DMF system formed distinct spherical aggregates, whereas water-THF formed indistinct large aggregates. It was inferred to be due to the low solubility of His6-GFP in THF.

Figure 15:
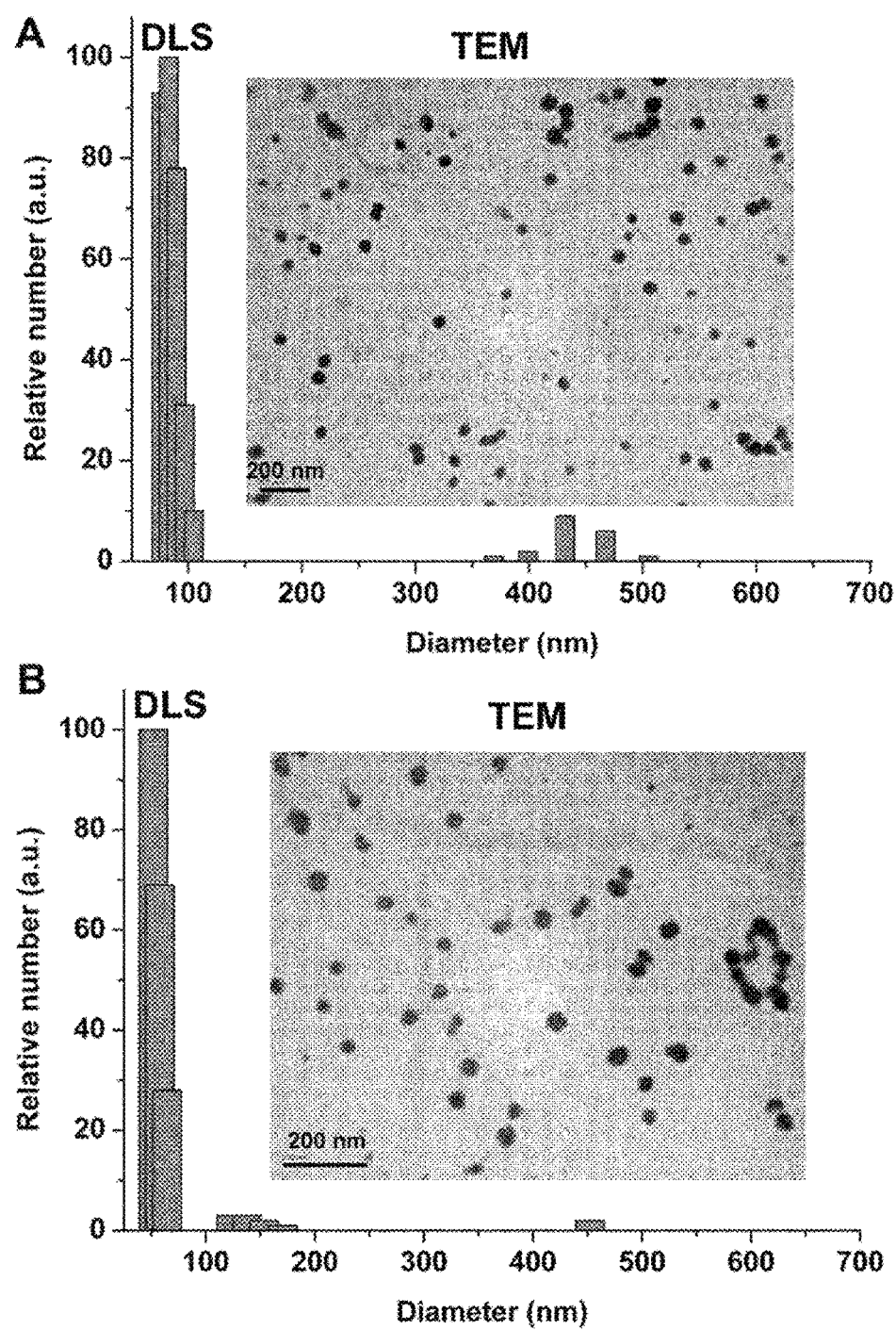
FIG. 15 shows the size and shape of the polymer-protein particles prepared from Ni-NTA-PS and His6-GFP in a water-DMF solution (4% by volume of DMF) according to Example 8. (A) is the DLS and TEM results after removal of DMF by dialysis (24 h) and (B) is the DLS and TEM results after the removal of DMF by dialysis (24 h) and the addition of an excess imidazole solution (250 mM).
Figure 16:
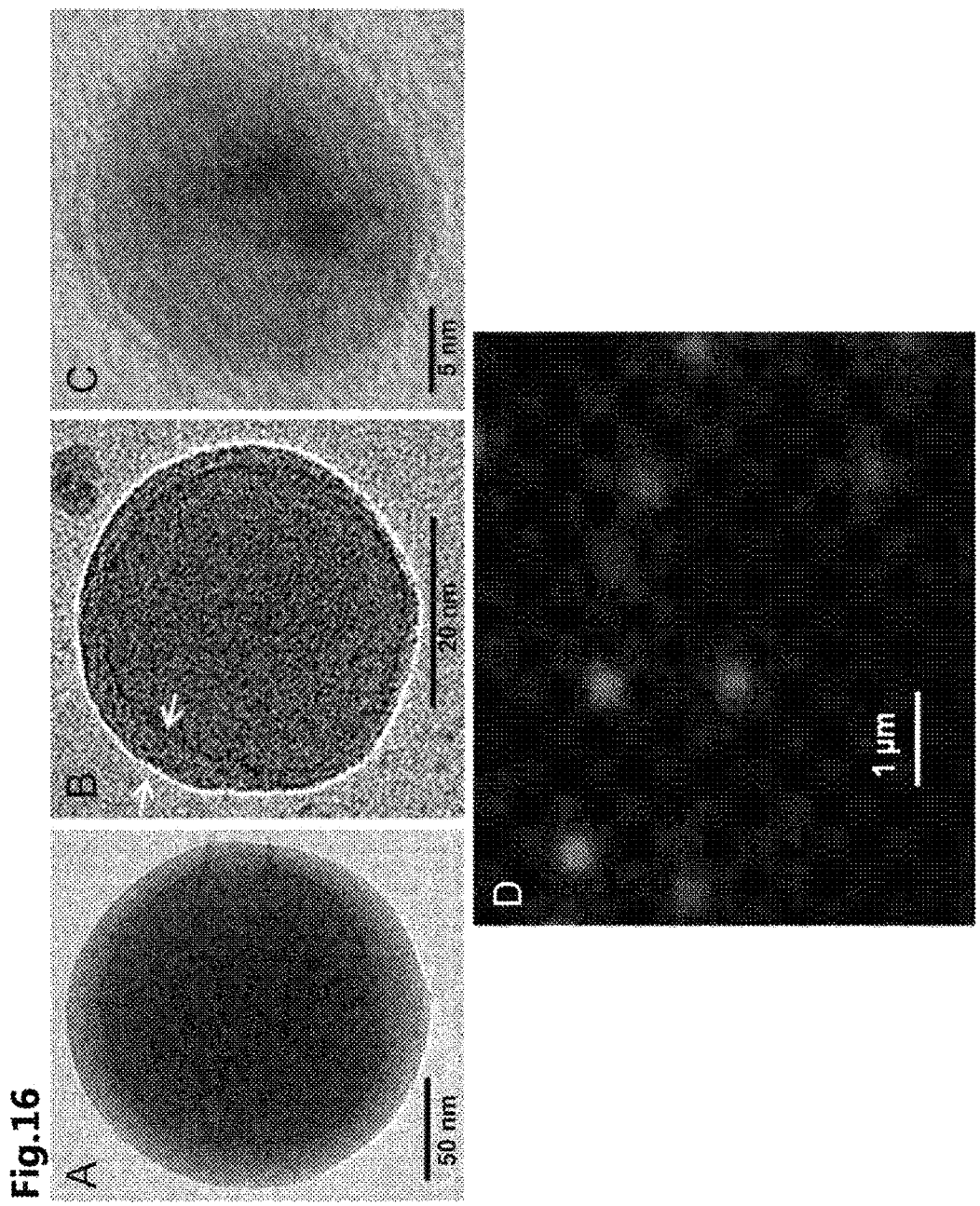
FIG. 16 shows the high resolution TEM images (A to C) and optical fluorescence microscopy image (D) according to Example 8. (A) and (B) are images of the outer layers of polymer-protein particles, and (C) is an image of particles after controlling the inside polymers by the addition of an imidazole solution of 250 mM. In (A), the protein layer outside the particle can be clearly confirmed. The arrow in (B) indicates the outer polymer layer. The images are adapted from different experiments performed under the same experimental conditions.

In order to prepare the polymer-protein hybrid aggregates, during the addition of the polymer into the aqueous solution (pH 7.4) containing the protein, 4 vol. % of DMF was added, which is a suitable solvent for Ni-NTA-PS. The organic solvent DMF can exist in the core of the spherical aggregates, and can also exist outside the aggregates in the above system. The presence of DMF in the core can cause the swelling of polystyrene. Therefore, in order to observe the effect of DMF on the aggregates, dynamically captured aggregates (the glass transition temperature of the polystyrene core is lower than that of these) were formed, and DMF was removed from the system by dialysis after the formation of spherical aggregates. TEM measurements and a DLS study showed that the initial aggregates were maintained even after dialysis (24 h) (FIG. 15A). However, the precipitation of the aggregate occurred over time due to the phase separation. This result indicated that the presence of DMF (4 vol. %) is essential in conserving the polymer-protein hybrid aggregates in the aqueous solution. In addition, in order to confirm the change in the shape of polymer-protein aggregates, an excess of an imidazole aqueous solution (250 mM) was added to the dialysis solution of the polymer-protein aggregates. TEM measurements and a DLS study showed that the size of polymer-protein aggregates was decreased (24 h; FIG. 15B). It was inferred to be due to the substitution of His-tagged GFP by the competitor, a ligand imidazole. After the addition of imidazole, the aggregates were unstable, and grouped together over time to form indistinct and larger amorphous aggregates.

The possible mechanism for the in situ formation of the polymer-protein hybrid aggregates inferred from the results of the experiments was confirmed to be due to the hydrophobic interaction of the internal Ni-NTA-PS and the increased stability by the hybrid through the His-tagged GFP. When Ni-NTA-PS dissolved in DMF was added to the aqueous solution, aggregation began due to the hydrophobicity of polystyrene and thus-produced aggregates comprise a hydrophilic nickel-complexed NTA moiety on the surface thereof, and the polystyrene matrix can thereby constitute the reverse-micelle in the core, which can be stabilized by the hydrophilic His-tagged protein through the NTA-Ni-histidine interaction in the aqueous solution.

EXAMPLE 9

Size Control of Protein-Coated Polymer Particles

In order to investigate the effects of various factors controlling the size of protein-coated polymer particles, the ratio of the amount of polymer to the amount of protein, pH of the reaction solution, the molecular weight of polymer, and the amounts used of the polymer and protein were varied, and the size of the resulting aggregates was measured to confirm the effects of these parameters on the size change of the aggregates.

1. Effect of Polymer Concentration

Protein-coated polymer particles were prepared by a method similar to that described in Example 1, wherein the ratio of the amount of polymer used to the amount of protein used was varied, and the size of the resulting particles was investigated.

Figure 17:
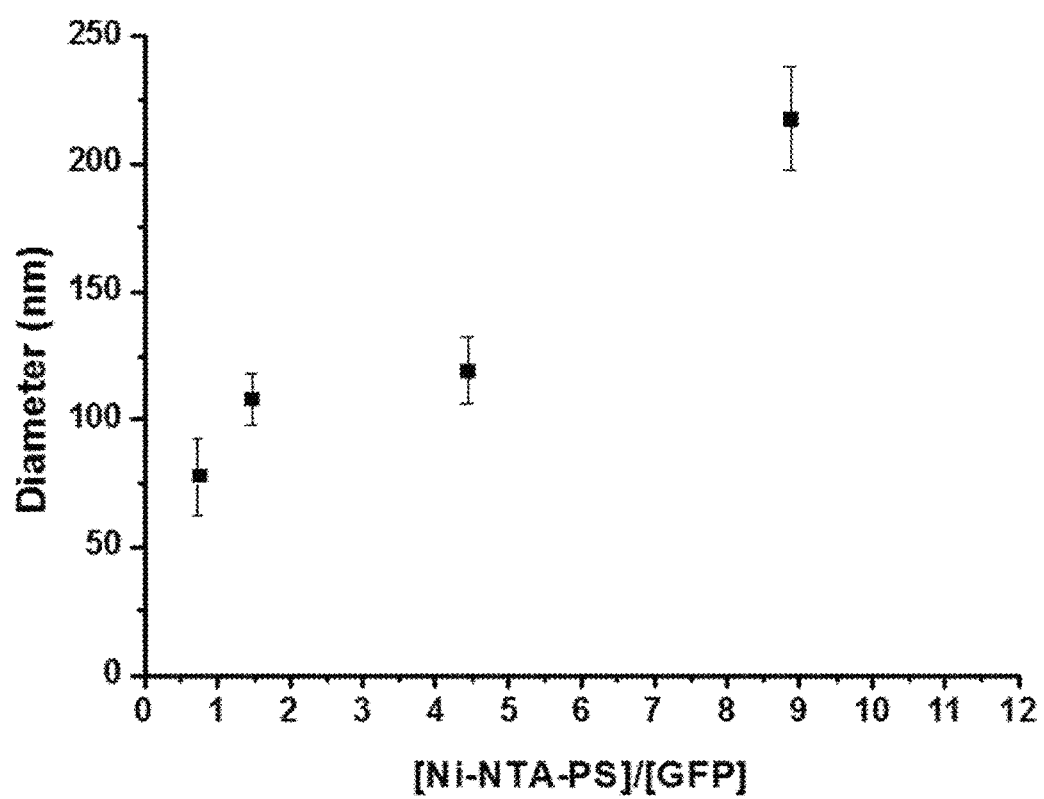
FIG. 17 shows the change in the particle size depending on the polymer concentration used in the preparation method of core-shell structured polymer-protein particles according to the present invention. The experiments were carried out at pH 8.0.

As shown in FIG. 17, the results showed that the size of the resulting aggregates increased as the amount of polymer used to that of protein increased.

2. Effect of pH

Protein-coated polymer particles were prepared by a method similar to that described in Example 1, wherein the pH of the solution was varied within the range of 6.5 to 8.5, and the size of the resulting particles was investigated.

Figure 18:
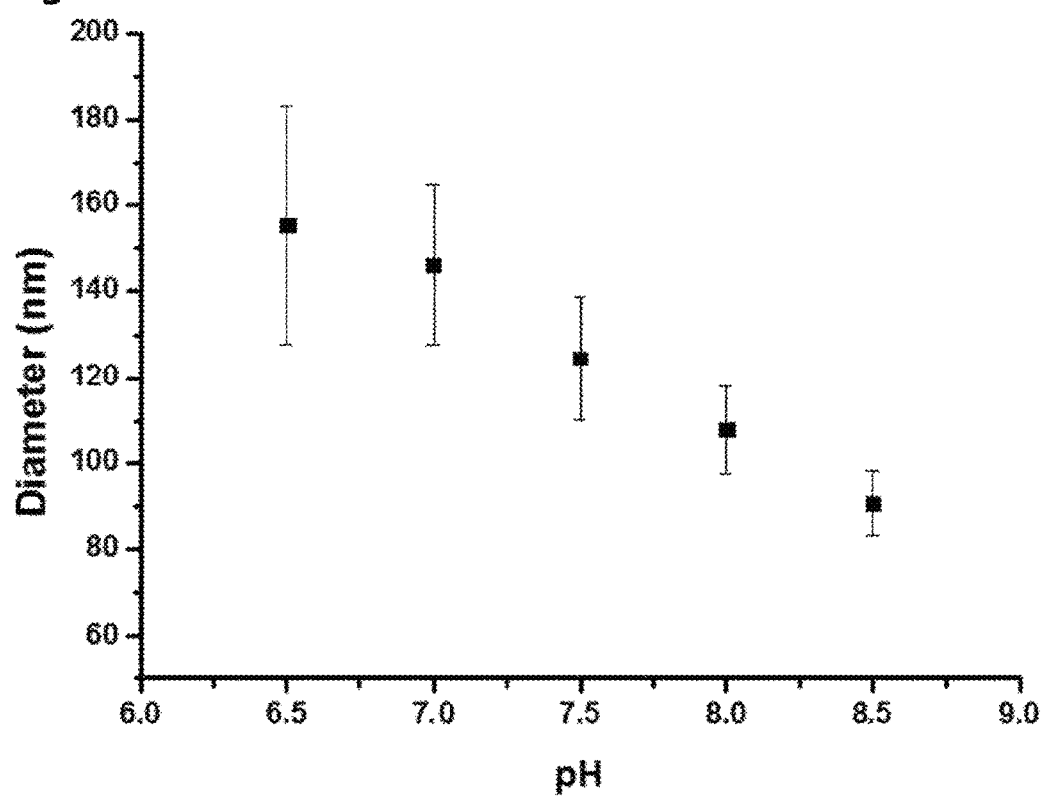
FIG. 18 shows the change in the particle size depending on the pH change in the preparation method of core-shell structured polymer-protein particles according to the present invention.

As shown in FIG. 18, the results showed that the size of the resulting particles decreased as the pH of the reaction solution during the preparation of aggregates increased.

3. Effects of Polymer Molecular Weight and Amounts of Polymer and Protein Used

Figure 19:
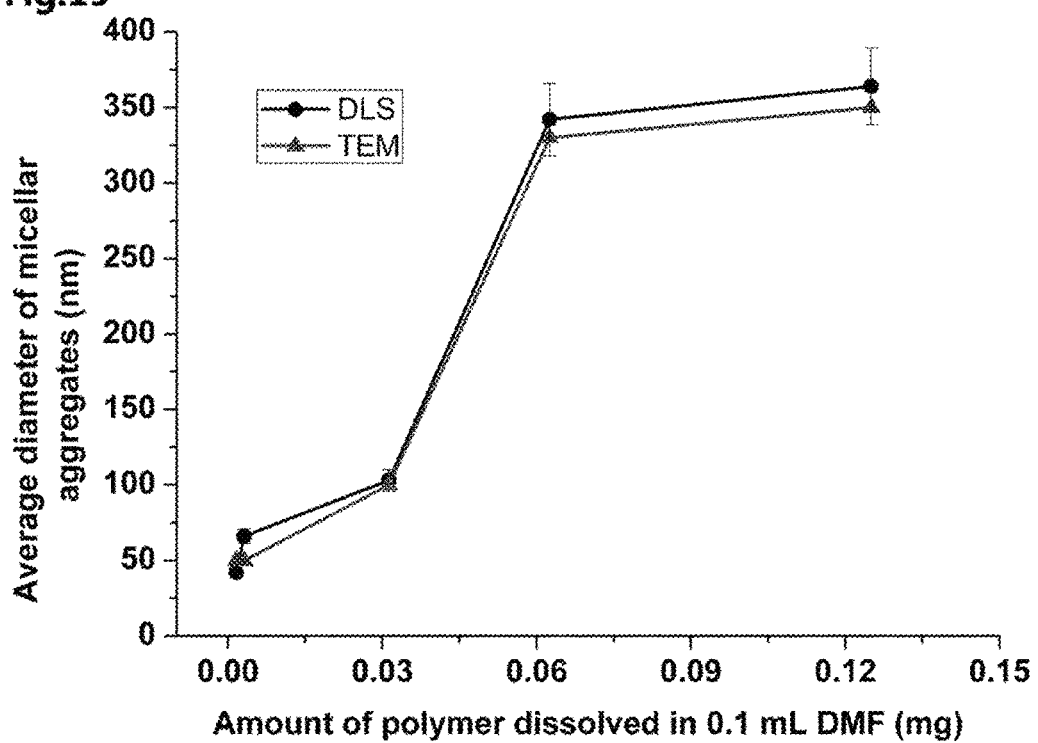
FIG. 19 shows the change of particle diameter versus the amount of Ni-NTA-PS (Mn of approx. 4,900) dissolved in 0.1 mL DMF, measured by DLS and TEM.

The same experiment was performed as in Example 1, except that Ni-NTA-PS with a molecular weight of 4,900 was utilized instead of Ni-NTA-PS with a molecular weight of 21,800 to prepare the aggregate together with His6-GFP, and the shape and size were analyzed by DLS and a TEM image and presented in FIG. 19 and Table 1. In addition, the size of the particles prepared while reducing the amounts of the polymer and the protein used was also disclosed in Table 1.

As shown in FIG. 19 and Table 1, taking into account that the size of the particles prepared using the high molecular weight polymer in the same concentration is approximately 100 nm, when the molecular weight of the polymer used was decreased to 4,900, the size of particles formed was confirmed to be remarkably increased to 280 nm to 350 nm.

In addition, as shown in Table 1, when the aggregates were formed while reducing the concentrations of the polymer and protein in the same ratio, the size of particles formed was confirmed to be decreased as the amounts of polymer and protein used were decreased.

TABLE 1

| Entry | $^a$Amount of polymer in 0.1 mL DMF [mg] | Amount of His6-GFP in 2.5 mL H$_2$O [µg] | Rate of addition of polymeric solution [mL/h] | $^b$Mean diameter of micellar aggregates (DLS) [nm] | $^c$Average size of micellar aggregates (TEM) [nm] |
|---|---|---|---|---|---|
| 1 | 0.125    | 540  | 0.01 | 365 ± 25.48 | ~350 |
| 2 | 0.0625   | 270  | 0.01 | 342 ± 23.94 | ~330 |
| 3 | 0.03125  | 135  | 0.01 | 103 ± 7.21  | ~100 |
| 4 | 0.003125 | 13.5 | 0.01 | 66 ± 4.62   | ~50  |
| 5 | 0.001562 | 6.75 | 0.01 | 42 ± 2.94   | ~50  |

$^a$prepared by stepwise dilution from a higher concentration.
$^b$mean diameter obtained from number distribution DLS measurements.

PREPARATION EXAMPLE 2

Preparation of Polymer Comprising NHS Functional Group

The reaction solution containing styrene (6.51 mL, 56.8 mmol) and anisole (3.5 mL) was deoxygenated by performing three cycles of a freeze-pump-thaw process. Then, CuBr (54.3 mg, 0.379 mmol), bpy (118 mg, 0.757 mmol), and N-hydroxysuccinimidyl 2-bromo-2-methylpropionate (100 mg, 0.379 mmol) were added to the reaction vessel, and pump-N$_2$ substitution was repeated three times. The reaction solution was reacted at 110° C. for 10 h. The reaction solution was diluted with THF, and a neutral alumina column was used to remove the Cu catalyst. The solution deprived of the Cu catalyst was added dropwise to an excess of methanol to precipitate and purify the polystyrene having an NHS functional group (Mn: 12,000, PDI: 1.12).

EXAMPLE 10

Preparation of Protein-Coated Polymer Nanoparticles and Protein Nanocage by Covalent Bond 1. Preparation of GFP-Coated Polymer Nanoparticles Polystyrene having an NHS functional group (0.26 mg, 2.2×10$^5$ mmol) was dissolved in 0.4 mL of DMF, and this solution was added dropwise to a PBS buffer solution (10 mL, 50 mM, pH 8.0) containing His6-GFP (0.16 mg, 1.5× 10$^{-5}$ mmol) at room temperature using a syringe pump at a rate of 0.04 mL/h to prepare a structure. The shape and size of the thus-prepared structure were measured by dynamic light scattering (DLS) and TEM, and the results are presented in FIG. 20.

1.1. Preparation of GFP-Coated Nanocage

The process of removing the polymer core from the polymer nanoparticles coated with GFP via a covalent bond as prepared in Example 10.1 was further practiced to prepare the protein nanocage comprising GFP. Specifically, 1.0 mL of a 2.5% glutaraldehyde aqueous solution was injected into the GFP-coated polymer nanoparticles for 30 min. Next, sodium borohydride was added to stop the reaction. 5 mL of THF was injected into the reaction mixture, which was stirred for 12 h. Next, THF was removed and the polymer which was not bound to the protein was removed by a membrane syringe filter.

2. Preparation of RFP-Coated Polymer Nanoparticles

Polystyrene having an NHS functional group (0.26 mg, 2.2×10$^{-5}$ mmol) was dissolved in 0.4 mL of DMF, and this solution was added dropwise to a PBS buffer solution (10 mL, 50 mM, pH 8.0) containing His6-RFP (0.16 mg, 1.5× 10$^{-5}$ mmol) at room temperature using a syringe pump at a rate of 0.04 mL/h to prepare a structure. The shape and size of the thus-prepared structure were measured by DLS and TEM, and the results are presented in FIG. 21.

3. Preparation of YFP-Coated Polymer Nanoparticles

Polystyrene having an NHS functional group (0.26 mg, 2.2×10$^{-5}$ mmol) was dissolved in 0.4 mL of DMF, and this solution was added dropwise to a PBS buffer solution (10 mL, 50 mM, pH 8.0) containing His6-YFP (0.17 mg, 1.5× 10$^{-5}$ mmol) at room temperature using a syringe pump at a rate of 0.04 mL/h to prepare a structure. The shape and size of the thus-prepared structure were measured by DLS and TEM, and the results are presented in FIG. 22.

4. Preparation of Fibrinogen-Coated Polymer Nanoparticles

Polystyrene having an NHS functional group (0.26 mg, 2.2×10$^{-5}$ mmol) was dissolved in 0.4 mL of DMF, and this solution was added dropwise to a PBS buffer solution (10 mL, 50 mM, pH 8.0) containing fibrinogen (2.0 mg, 1.5× 10$^{-5}$ mmol) at room temperature using a syringe pump at a rate of 0.04 mL/h to prepare a structure. The shape and size of the thus-prepared structure were measured by DLS and TEM, and the results are presented in FIG. 23.

PREPARATION EXAMPLE 3

Preparation of Polymer Comprising Biotin Functional Group

1. Synthesis of Biotinylated RAFT Reagent

Biotin (0.5 g, 2.0 mmol) and carbonyldiimidazole (0.64 g, 4.0 mmol) were dissolved in DMF (20 mL), and reacted for 6 h at room temperature. 2-(2-Aminoethoxy)ethanol (0.63 mL, 6.0 mmol) was further added to the reaction solution and stirred for 18 h. After removal of the solvent, biotinyl alcohol was purified by column chromatography (stationary phase: silica, mobile phase: 1-butanol/acetic acid/water=80/ 10/10). Purified biotinyl alcohol (0.35 g, 1.0 mmol) was dissolved in DMF and reacted with S-1-dodecyl-S'-(α,α'-dimethyl-α"-acetic acid) trithiocarbonate (0.37 g, 1.0 mmol), DCC (0.205 g, 1.0 mmol), and DMAP (0.015 g, 0.12 mmol) for 48 h at room temperature. After solid precipitate filtration and solvent removal, the biotinylated RAFT reagent was purified by column chromatography (stationary phase:silica, mobile phase:chloroform/methanol=70/30).

2. Preparation of Polystyrene Functionalized by Biotin

Styrene (2 mL, 17.4 mmol), AIBN (1.43 mg, 0.01 mmol), and biotinylated RAFT reagent (59.1 mg, 0.08 mmol) were added to anisole (0.8 mL) deprived of oxygen, and reacted at 65° C. for 131 h. After polymerization, the reaction mixture solution was added to excess methanol and precipitated to obtain the polystyrene having a biotin functional group (Mn: 9,200, Mw: 11,100, PDI: 1.18).

EXAMPLE 11

Preparation of Protein-Coated Polymer Nanoparticles and Protein Nanocage by Ligand-Receptor Binding Polystyrene having a biotin functional group (0.2 mg, $2.2 \times 10^{-5}$ mmol) prepared according to Preparation Example 3 was dissolved in 0.4 mL of DMF, and this solution was added dropwise to a PBS buffer solution (10 mL, 50 mM, pH 8.0) containing streptavidin (0.79 mg, $1.5 \times 10^{-5}$ mmol) at room temperature using a syringe pump at a rate of 0.04 mL/h to prepare a structure.

EXAMPLE 12

Preparation of Protein-Coated Polymer Nanoparticles Comprising Two or More Different Types of Proteins Ni-NTA-PS (0.1 mg, $1.5 \times 10^{-5}$ mmol) prepared according to Preparation Example 1 was dissolved in 0.2 mL of DMF, and this solution was added dropwise to a PBS buffer solution (5 mL, 50 mM, pH 7.4) containing His6-GFP (0.2 mg, $0.7 \times 10^{-5}$ mmol) and His6-lipase (0.3 mg, $0.7 \times 10^{-5}$ mmol) at room temperature using a syringe pump at a rate of 0.02 mL/h. After addition over 10 h, the reaction mixture was stirred for one day.

PREPARATION EXAMPLE 4

Preparation of Polymer Bound Tri-NI-NTA at its Terminal

Figure 24A:
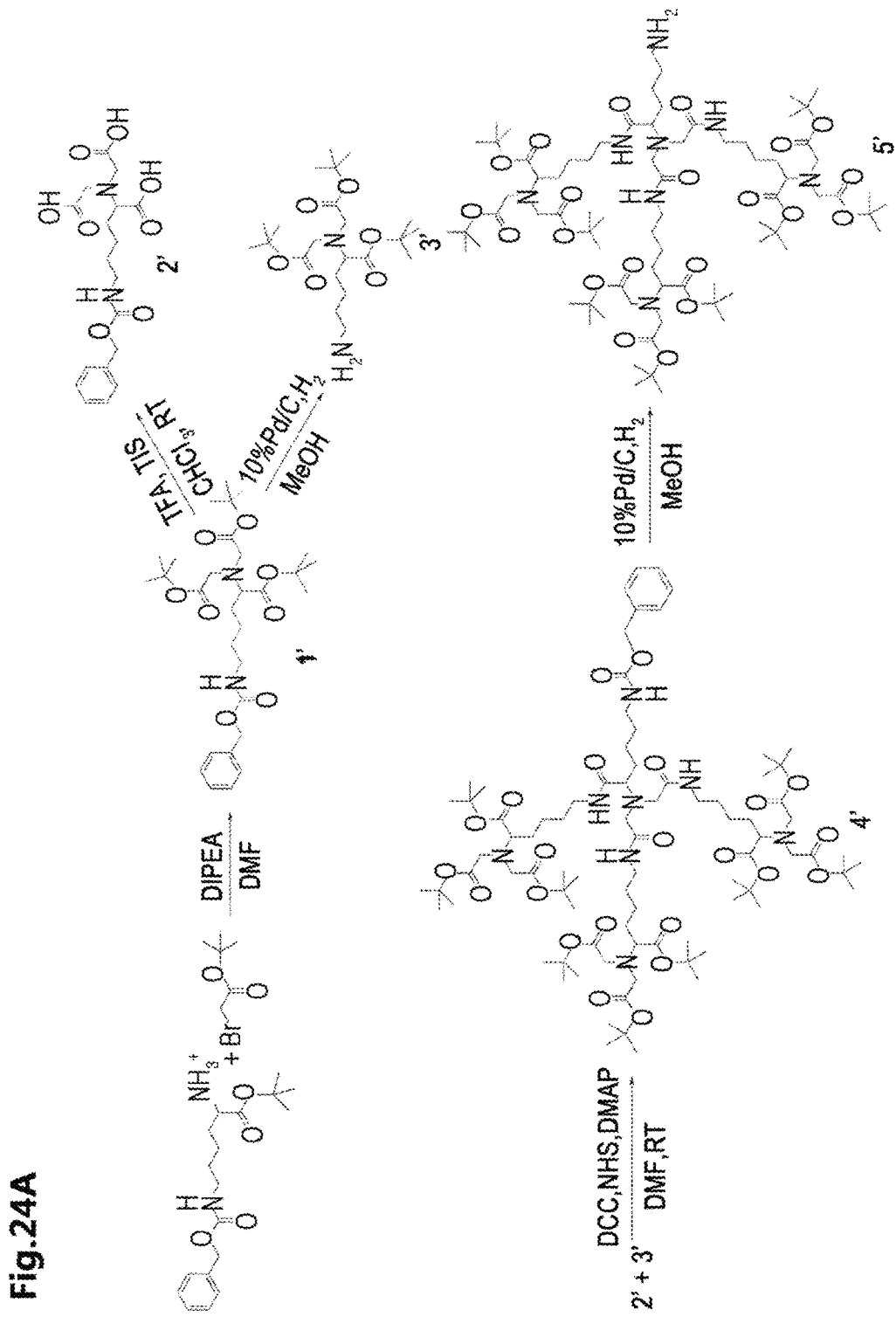
FIG. 24 is a reaction scheme for the synthesis of polystyrene (tri-NTA-PS, 8') wherein tri-NTA is bound to the terminal by ATRP (atom transfer radical polymerization).
Figure 24B:
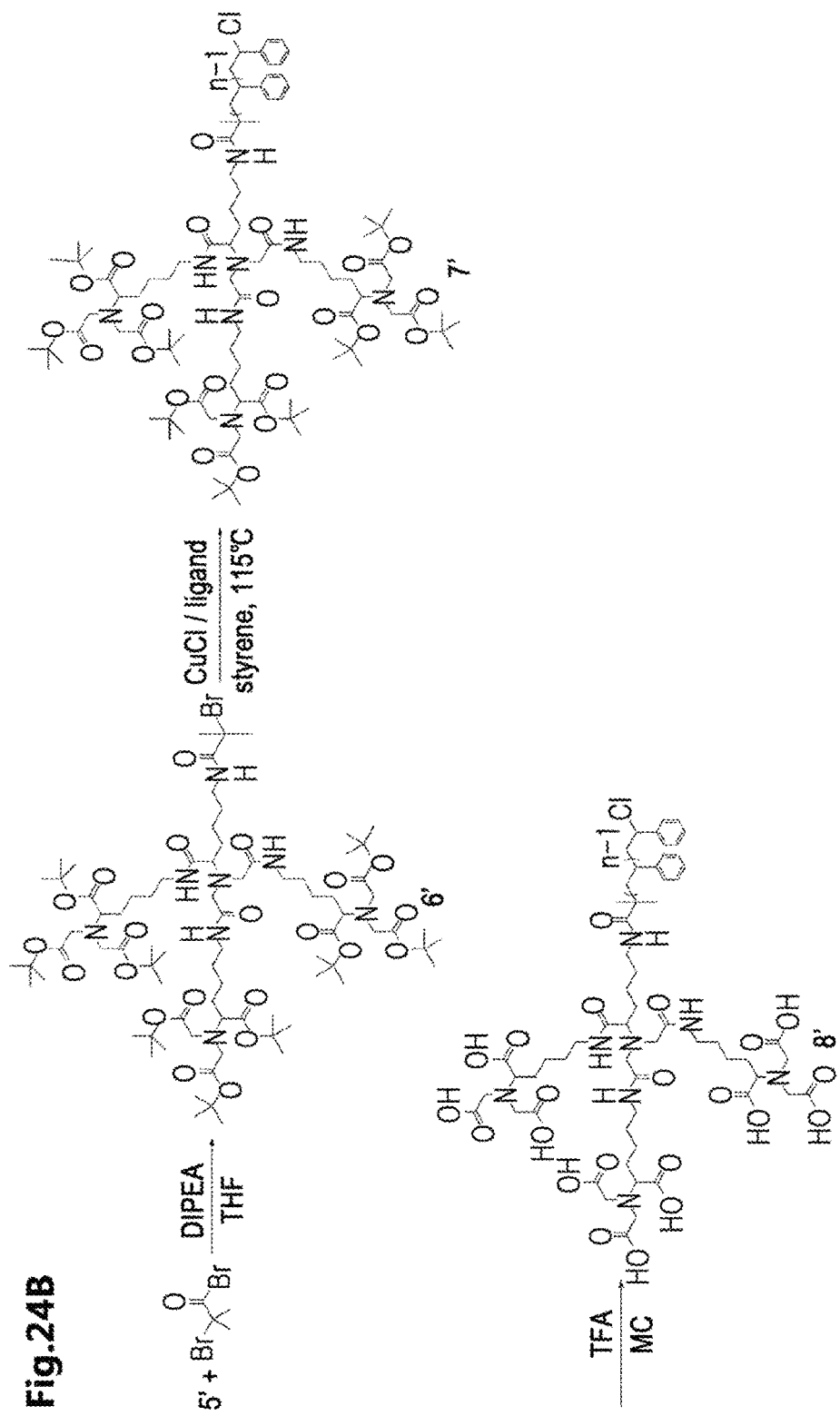

As an example for the preparation of a polymer comprising three functional groups, which can bind to a protein, per one molecule of polymer, a polystyrene polymer which has three nickel-complexed NTA bound to its terminal was prepared. The method of preparing the polymer is shown in FIG. 24.

1. Synthesis of Protected Tri-NTA Initiator (6')

Synthesis of Compound 1'
tert-Butyl bromoacetate (7.84 mL, 50.361 mmol) and N,N-diisopropylethylamine (DIPEA) (4.6 mL, 26.412 mmol) were added to the suspension in which H-Lys(Z)-OtBu.HCl (2 g, 5.360 mmol) was dissolved in 50 mL of DMF under a nitrogen atmosphere. The reaction mixture was stirred overnight at 55° C. Volatiles were evaporated at 65° C. under vacuum. A slurry residue was extracted with cyclohexane:ethyl acetate (3:1). The extract was concentrated and analyzed by chromatography on silica gel using hexane:ethyl acetate (4:1) as a mobile phase.

Yield: 2.8 g (92.5% on the basis of H-Lys(Z)-OtBu.HCl).
TLC: $R_f$=0.38 (hexane:ethyl acetate=4:1).
$^1$H NMR (300 MHz, CDCl$_3$), δ (TMS, ppm): 1.42 (s, 18H), 1.45 (s, 9H), 1.53 (m, 4H), 1.62 (m, 2H), 3.20 (m, 2H), 3.31 (t, J=7.2, 1H), 3.44 (dd, J=16, 8.4, 4H), 5.08 (s, 2H), 7.34 (m, 5H).

Synthesis of Compound 2'
10% Pd/C (150 mg) was added to the methanol solution of 1' (1.7 g/50 mL, 3.013 mmol) under a nitrogen atmosphere. The reaction mixture was stirred vigorously under a hydrogen atmosphere at room temperature for 9 h. Pd/C was filtered on celite, and the filtrate was evaporated under reduced pressure.

Yield: 1.15 g (88.7% on the basis of 1').
TLC: $R_f$=0.5 (chloroform:methanol=6:1).
$^1$H NMR (300 MHz, CDCl$_3$), δ (TMS, ppm): 1.44 (s, 18H), 1.45 (s, 9H), 1.63 (m, 6H), 2.87 (t, J=7.2, 2H), 3.29 (t, J=7.6, 1H), 3.44 (dd, J=17.2, 9.2, 4H).

Synthesis of Compound 3'
5.46 mL of trifluoroacetic acid (TFA) and 0.3 mL of triisopropylsilane (TIS) were added to the chloroform solution of 1' (2 g/30 mL, 3.542 mmol). The reaction mixture was stirred at room temperature and analyzed by TLC. After 3 h, 7 mL of methanol and 4 mL of water were added to the reaction mixture. Volatiles were evaporated under reduced pressure. The residue was dried azeotropically with toluene and precipitated from anhydrous ethyl ether. The white precipitate was recovered and dried under high vacuum.

Yield: 1.3 g (92.6% on the basis of 1').
TLC: $R_f$=0.06 (chloroform:methanol:water=65:25:4).
$^1$H NMR (300 MHz, CDCl$_3$), δ (TMS, ppm): 1.48-1.53 (m, 4H), 1.66 (m, 1H), 1.78 (m, 1H), 3.15 (m, 2H), 3.45 (t, J=12.8, 1H), 3.63 (dd, J=18, 9.6, 4H), 5.08 (s, 2H), 7.36 (m, 5H).

Synthesis of Compound 4'
NHS (400 mg, 3.484 mmol), DMAP (58 mg, 0.468 mmol), and DCC (985 mg, 4.772 mmol) were added to the solution in which 3' (400 mg, 0.952 mmol) was dissolved in 20 mL of anhydrous DMF. The reaction mixture was stirred at room temperature for 2 h, and to this mixture was added the solution in which 2 (1.49 g, 3.479 mmol) and N,N-diisopropylethylamine (DIPEA, 0.63 mL, 3.479 mmol) were dissolved in 10 mL of chloroform. After reacting overnight, volatiles were evaporated at 65° C. under vacuum. The residue was dissolved in hexane:ethyl acetate (1:1), and the solution was filtered to remove a urea slurry. Volatiles were extracted with water three times. Combined extracts were concentrated and analyzed by chromatography on silica gel using chloroform:methanol (30:1) as a mobile phase.

Yield: 1.23 g (74.6% on the basis of 3').
TLC: $R_f$=0.34 (chloroform:methanol=30:1).
$^1$H NMR (300 MHz, CDCl$_3$), δ (TMS, ppm): 1.44 (s, 54H), 1.46 (s, 27H), 1.53 (m, 16H), 1.63 (m, 8H), 3.20-3.31 (m, 12H), 3.44 (m, 16H), 5.08 (s, 2H), 7.34 (m, 5H).

Synthesis of Compound 5'
10% Pd/C (130 mg) was added to the methanol solution of 4' (1.0 g/40 mL, 0.612 mmol) under a nitrogen atmosphere. The reaction mixture was stirred vigorously under a hydrogen atmosphere at room temperature for 9 h. Pd/C was filtered on celite, and the filtrate was evaporated under reduced pressure.

Yield: 0.8 g (87.1% on the basis of 4').
TLC: $R_f$=0.48 (chloroform:methanol=9:1).

$^1$H NMR (300 MHz, CDCl$_3$), δ (TMS, ppm): 1.44 (s, 54H), 1.46 (s, 27H), 1.53 (m, 16H), 1.63 (m, 8H), 3.20-3.31 (m, 12H), 3.44 (m, 16H).

Synthesis of Compound 6'

After the syntheses of Compounds 1', 2', 3', 4', and 5' by the aforementioned methods, 2-bromo isobutyryl bromide (0.078 mL, 0.636 mmol) and DIPEA (0.28 mL, 1.592 mmol) were slowly added to the dry THF solution of 5 (0.8 g/15 mL, 0.533 mmol) under a nitrogen atmosphere at 0° C. The reaction mixture was stirred overnight at room temperature. Volatiles were evaporated at 50° C. under vacuum. The residue slurry was dissolved in dichloromethane and extracted with water three times. Combined extracts were concentrated and purified by flash column chromatography on silica gel using chloroform:methanol (30:1) as a mobile phase.

Yield: 0.63 g (71.7% on the basis of 5').

TLC: R$_f$=0.26 (chloroform:methanol=30:1).

$^1$H NMR (300 MHz, CDCl$_3$), δ (TMS, ppm): 1.44 (s, 54H), 1.46 (s, 27H), 1.53 (m, 16H), 1.63 (m, 8H), 1.88 (s, 6H), 3.20-3.31 (m, 12H), 3.44 (m, 16H).

$^{13}$C NMR (300 MHz, CDCl$_3$) δ (TMS, ppm): 23.30, 28.35, 28.43, 30.13, 32.63, 34.40, 39.50, 48.77, 53.97, 65.20, 77.23, 170.08, 172.50.

As described above, in order to synthesize the polymer modified by multivalent NTA at its terminal by atom transfer radical polymerization (ATRP), properly protected tri-NTA initiator (6') was first prepared. First, at least two tert-butyl acetate groups were introduced to the α-nitrogen atom to convert H-Lys(Z)-OtBu.HCl to 1'. The selective removal of the protecting group from 1' provided the 1$^{st}$ generation NTA dendron comprising one amino group (2') or three carboxy groups (3'). Completely protected Compound 4' was obtained by the coupling of 2' and 3', and dendrimer 5', which was modified at the amine group and protected by tert-butyl, was obtained therefrom by catalytic hydrogenation.

Figure 26:
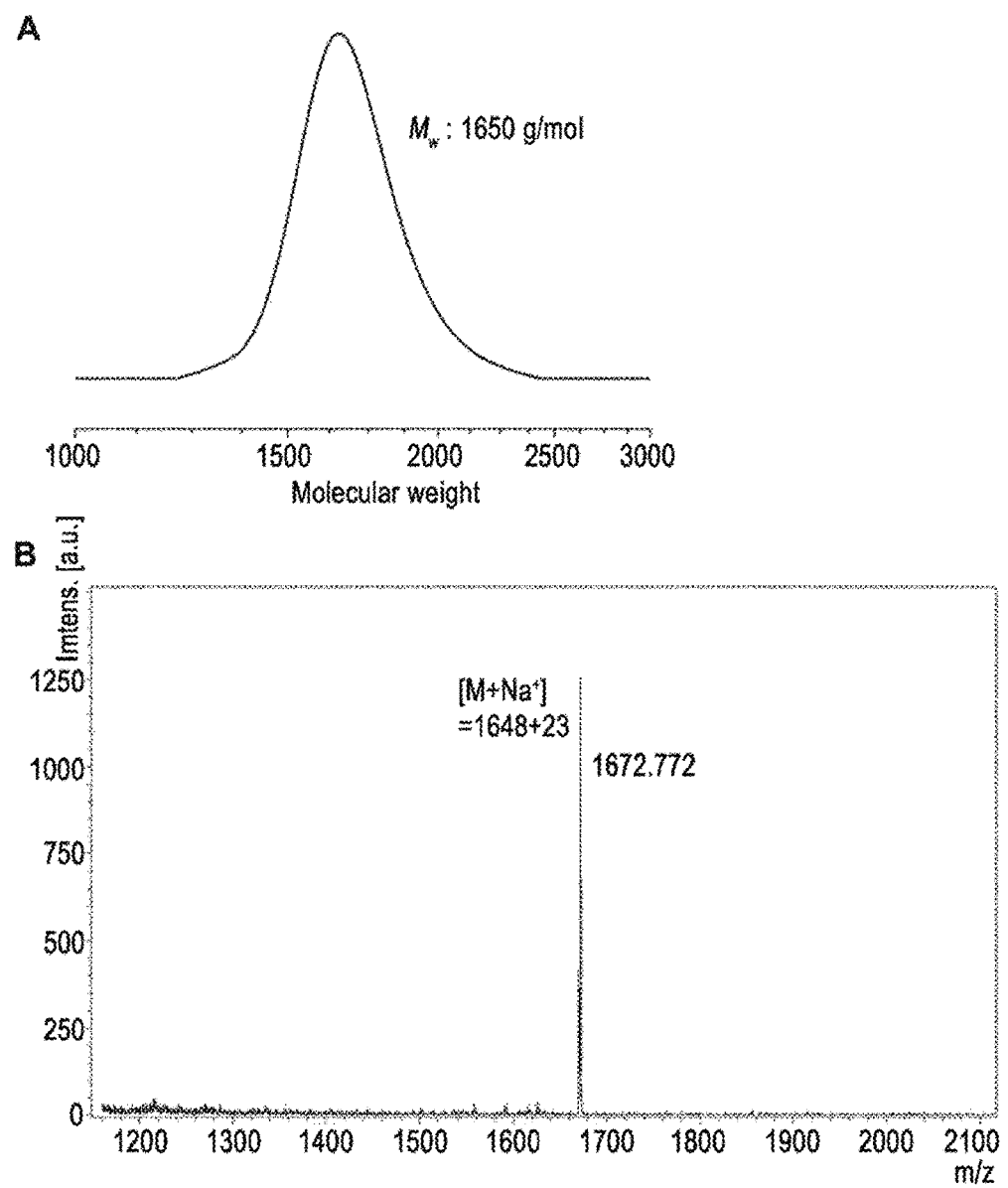
FIG. 26 shows the analysis results by gel permeation chromatography (A) and MALDI-TOF mass spectrometry (B) of a p-tri-NTA initiator (6').

Thus-obtained 5' was reacted with 2-bromoisobutyryl bromide to form an amide bond therebetween, thereby preparing ATRP initiator 6' comprising an activated alkyl bromide and an NTA moiety protected by tert-butyl at its terminal. In order to enhance solubility and block side reactions (e.g., proton addition reaction of ATRP ligand), a tert-butyl-protected NTA-based amide initiator was designed. The structure of the synthesized initiator (6') was confirmed by $^1$H NMR and $^{13}$C NMR (FIG. 25). The peak at approximately 1.4 ppm in $^1$H NMR and the peak at approximately 28 ppm in $^{13}$C NMR can be assigned as the tert-butyl proton. The molecular weight of 6' was determined by gel permeation chromatography (GPC) and MALDI-TOF (matrix assisted laser desorption ionization-time of flight) mass spectrometry (FIG. 26). The molecular weight of 6' by GPC was 1,650 g/mol, and the m/z of the sodium adduct of the p-tri-NTA initiator by MALDI-TOF analysis was 1,672.772.

2. Preparation of Polystyrene Functionalized by Tri-NTA (8')

Introduction of Tri-NTA into Polymer (7')

Styrene (1.0 mL) and anisole (1.0 mL) were added to a Schlenk flask filled with nitrogen, three cycles of a freeze-pump-thaw process were repeated, and then CuCl (17.5 mg) and dNbpy (71.27 mg) were added to the flask and two cycles of the freeze-pump-thaw process were further performed. The flask was set up in an oil bath at 115° C., and then p-tri-NTA initiator 6' (140 mg, 85.2×10$^{-3}$ mmol) was added and stirred for 10 h. 0.1 mL aliquots were taken from the reaction mixture at time intervals and diluted with THF for the GPC analysis. Precipitation from methanol was performed to isolate the protected tri-NTA-bound polymer.

Removal of Protecting Group of 7' (8')

In a flask, the above-obtained protected tri-NTA-polystyrene (p-tri-NTA-PS) 7' (100 mg, 15.63×10$^{-3}$ mmol) was dissolved in 6.0 mL of CH$_2$Cl$_2$. Trifluoroacetic acid (TFA, 0.96 mL, 14.06 mmol) was added to the above flask. After completion of the addition of TFA, the reaction mixture was stirred at room temperature for 24 h. Finally, precipitation from methanol was performed to acquire the deprotected tri-NTA-polystyrene (tri-NTA-PS, 8').

Using the p-tri-NTA ATRP initiator (6') prepared according to Preparation Example 4.1, the polymerization of styrene was performed at 115° C. in solution phase (FIG. 24). Since amide-based initiators generally exhibit the initiation behavior in ATRP, halogen exchange technique was utilized to perform the polymerization reaction. In the halogen exchange reaction, a CuCl/dNbpy catalyst was used together with the initiator. Accordingly, 6' and the CuCl/dNbpy catalyst were used to synthesize p-tri-NTA polystyrene (p-tri-NTA-PS, 7') by ATRP.

Figure 27:
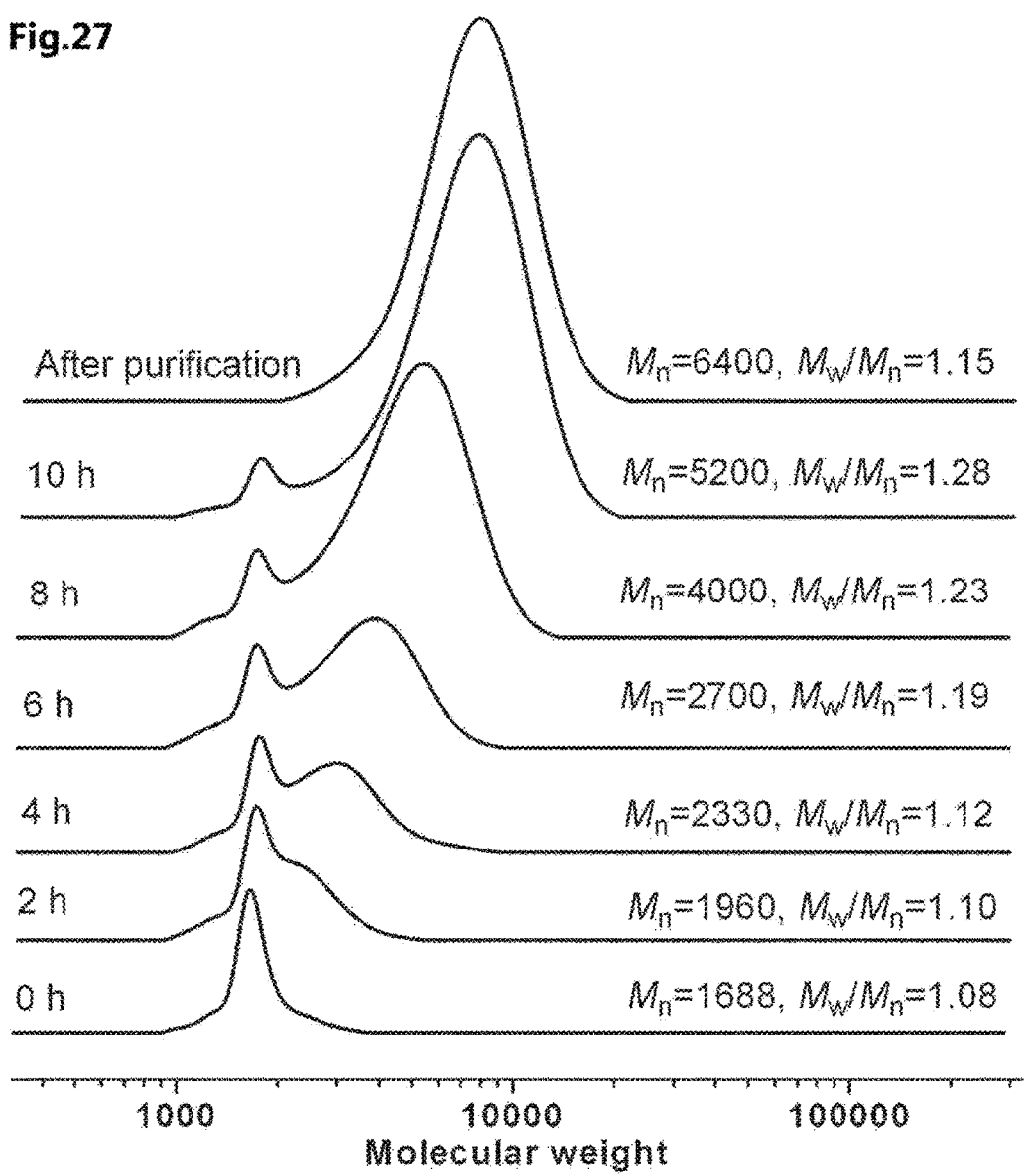
FIG. 27 shows the ATRP results of styrene using a p-tri-NTA initiator (6'). Molecular weight (Mn) and dispersity (Đ) over time are shown together with the gel permeation chromatography of tri-NTA-PS (7'). The concentration ratio of the initial reactants was $[Styrene]_0:[initiator]_0:[CuCl]_0:[dNbpy]_0 = 100:1:10:20$, and anisole in 50% by volume was used as the solvent at 115° C.

Gel permeation chromatography results showed that the molecular weight of the synthesized polymer increased over time, and there appeared double peaks due to the presence of excess initiator despite the use of a halogen exchange technique (FIG. 27). However, after the polymer purification by methanol precipitation, one symmetric elution peak was observed with narrow dispersion (Mn=6400 and Đ=1.15) (FIG. 27).

Figure 29:
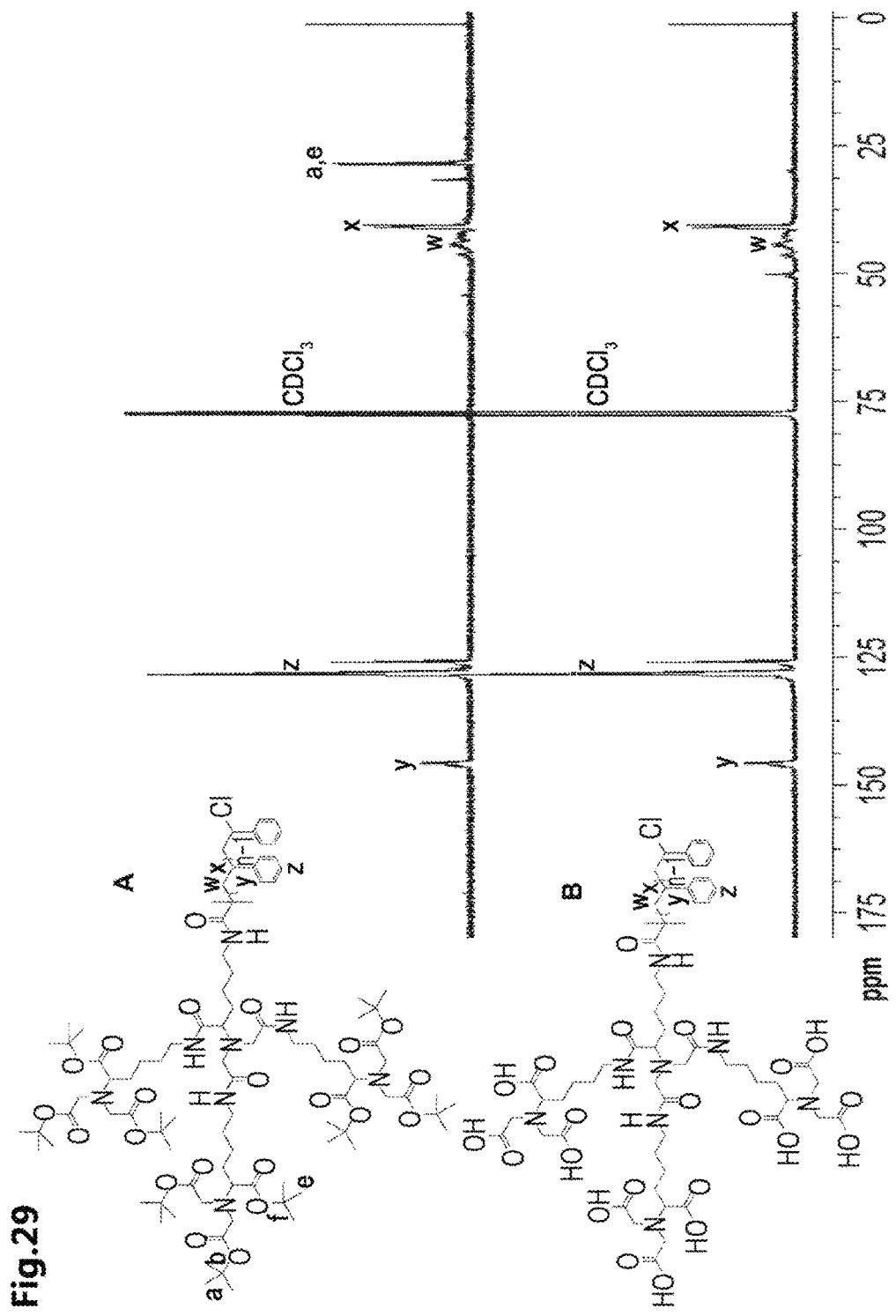
FIG. 29 shows $^{13}$C NMR (300 MHz) spectra of (A) p-tri-NTA-PS (Mn, GPC=6,400 g/mol, Đ=1.15; 7') and (B) tri-NTA-PS (Mn, GPC=5,400 g/mol, Đ=1.17; 8').

In the above-synthesized tri-NTA-bound polystyrene (7'), the presence of an NTA moiety was confirmed by $^1$H NMR (FIG. 28A) and $^{13}$C NMR (FIG. 29A). In FIG. 28, the peaks at 1.45 (a, (CH$_3$)$_3$—) and 1.46 ppm (b, (CH$_3$)$_3$—) were assigned as the tert-butyl proton, and the peaks at 2.8 (h, —CH$_2$—), 3.2 (d, —CH—), 3.45 (c, —CH$_2$—), and 4.43 (m, —CH—Cl) ppm were assigned as the NTA moiety. From these results, 6' was found to be successfully used as the ATRP initiator. Polystyrene bound with tri-NTA at its terminal (tri-NTA-PS, 8') was prepared by removing the tert-butyl group of 7' with TFA in CH$_2$Cl$_2$. The structure of 8' was also confirmed by $^1$H NMR (FIG. 28B) and $^{13}$C NMR (FIG. 29B).

As described above, in the present invention, three NTA moieties were introduced at the α-chain terminal of polystyrene to obtain the amphiphilic linear-dendritic block copolymer (8'). Thus, the present inventors have studied the self-assembly behavior of tri-NTA-PS (8') in aqueous solutions. When water was slowly added to the THF solution of tri-NTA-PS (8') in a glass vial under vigorous stirring at room temperature, self-assembled particles were formed. TEM and DLS measurements confirmed that these particles were spherical and uniform and had the diameter of approximately 40 nm to 60 nm (FIG. 30). These particles can provide the surface with a hydrophilic NTA moiety, and can thereby be applied in various fields.

3. Preparation of Polymer Particles by Self-Assembly of Tri-NTA-PS

In a glass vial, tri-NTA-PS (8, 2 mg, Mn (GPC) of approx. 5,400) was dissolved in 1 mL of dry THF. Next, 2 mL of water was slowly added under vigorous stirring at room temperature. After completion of the addition of water, the shape was investigated by TEM and DLS measurements while continuously stirring the reaction solution.

EXAMPLE 13

Preparation of Polymer-Protein Hybrid Nanoparticles by Binding of his-Tagged Protein and Tri-NTA-PS Polystyrene modified by nickel-complexed tri-NTA at its terminal (Ni-tri-NTA-PS, Mn of approx. 24,500, 0.25 mg, $1.02 \times 10^5$ mmol) was dissolved in 0.2 mL of DMF. In a glass vial, this polymer solution was slowly added to 5 mL of deionized water comprising His6-GFP (27 kDa, 207 g, $7.7 \times 10^6$ mmol), using a syringe pump at a rate of 0.02 ml/h under stirring at room temperature (18° C.). Several drops of PBS (50 mM, pH of approx. 7.4) were added to maintain the pH at 7.4 before the polymer solution was added to a water-soluble protein solution. After completing the addition of the polymer solution (10 h), the resulting polymer-protein hybrid solution was continuously stirred, during which the self-assembled form thereof was analyzed by DLS and TEM.

According to the aforementioned method for the preparation of protein-coated polymer nanoparticles, the self-assembled form of tri-NTA-PS (8'), which was conjugated with His6-GFP through the interaction of NTA-Ni/His in water/DMF (DMF 4 vol. %) after being complexed with nickel, was studied. When deionized water (5 mL, pH 7.4) comprising His6-GFP (27 kDa, 207 μg, $7.7 \times 10^{-6}$ mmol) was added into the polymer solution prepared by dissolving 0.25 mg of nickel-complexed tri-NTA-PS (Mn of approx. 24,500, 0.25 mg, $1.02 \times 10^{-5}$ mmol) in DMF (0.2 mL), spherical core-shell hybrid particles having the size of approximately 90 nm to 115 nm were obtained, as expected. DLS data and representative TEM images were presented in FIG. 31, demonstrating the shape and size of the above particles. From the TEM image (right) of FIG. 31, the outer layer of a particle could be confirmed, which was considered as a protein layer. DLS data and TEM measurements showed that these hybrid particles of nickel-complexed tri-NTA-PS and His6-GFP were stable in water/DMF up to fifteen days, and they exhibited very high similarity to that prepared from Ni-NTA-PS.

As a result, the present invention confirmed the synthesis of tri-NTA-PS by ATRP and its binding to His6-GFP in water/DMF as well as the self-assembly of the polymer itself in water/THF. First, a tert-butyl-protected NTA-based amide initiator was prepared and characterized with $^1$H NMR, $^{13}$C NMR, GPC, and MALDI-TOF mass spectrometry. The tert-butyl group was removed from the α-chain terminal of polystyrene to prepare polystyrene which had deprotected tri-NTA bound to its terminal (tri-NTA-PS). While tri-NTA-PS, due to its amphiphilicity, self-assembled to form spherical particles having a diameter of approximately 40 nm to 60 nm in water/THF, nickel-complexed tri-NTA-PS and His6-GFP formed spherical core-shell hybrid particles having a diameter of approximately 90 nm to 115 nm in water/DMF through the interaction of NTA-Ni/His.

Since tri-NTA-PS comprises three NTA moieties, it is dendritic and more amphiphilic. It suggests that the polymer-protein hybrid particles or protein cage according to the present invention can be useful in similar applications, and can particularly be applied in the production of various self-assembled forms of the polymer itself, enclosure of hydrophobic additives such as nanoparticles, dyes, etc., targeted drug delivery, and protein purification.

The invention claimed is:

1. A method for preparing a protein cage which comprises:
    a $1^{st}$ step of preparing an amphiphilic polymer comprising a $1^{st}$ hydrophobic polymer and a $1^{st}$ hydrophilic functional group;
    a $2^{nd}$ step of preparing a hydrophilic protein comprising a $2^{nd}$ functional group binding to the $1^{st}$ functional group;
    a $3^{rd}$ step of forming an amphiphilic polymer-protein hybrid by the binding of the $1^{st}$ functional group and the $2^{nd}$ functional group, and forming core-shell structured particles comprising a protein shell and an amphiphilic polymer core by the self-assembly of the amphiphilic polymer in a hydrophilic solvent; and
    a $4^{th}$ step of removing some or all of the hydrophobic polymer of the core part from the core-shell structured particles.

2. The method of claim 1, wherein the protein retains its activity by maintaining its tertiary structure.

3. The method of claim 1, wherein the protein cage comprises one or at least two types of proteins.

4. The method of claim 1, wherein the method further comprises a step of forming bindings between the shell-forming proteins by adding a cross-linking agent to the core-shell structured particles which are formed in the $3^{rd}$ step.

5. The method of claim 1, wherein a $2^{nd}$ hydrophobic polymer not having the $1^{st}$ functional group is further added during the $3^{rd}$ step.

6. The method of claim 1, wherein an additive is loaded in the protein cage.

7. The method of claim 1, wherein the additive is added in the $3^{rd}$ step to be included in the core part during the self-assembly or is injected into the protein cage formed in the fourth step.

8. The method of claim 1, wherein removal of some or all of the hydrophobic polymer of the core part from the core-shell structured particles in the fourth step is performed by the introduction of (i) a competitor compound for the binding between the $1^{st}$ and the $2^{nd}$ functional groups, or (ii) a compound that hydrolyzes the polymer moiety in the amphiphilic polymer-protein hybrid.

* * * * *